United States Patent
Choung et al.

(10) Patent No.: US 11,998,179 B2
(45) Date of Patent: *Jun. 4, 2024

(54) TISSUE SAMPLE HOLDER WITH ENHANCED FEATURES

(71) Applicant: Devicor Medical Products, Inc., Cincinnati, OH (US)

(72) Inventors: Rachel Yoon Choung, Studio City, CA (US); Robert M. Householder, Loveland, OH (US); Andrew P. Nock, Dayton, OH (US); Andrew Robinson, Cincinnati, OH (US); Jordan Smith, Loveland, OH (US); Kevin Talbot, North Bend, OH (US); Emmanuel V. Tanghal, Mason, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 776 days.

This patent is subject to a terminal disclaimer.

(21) Appl. No.: 17/140,322

(22) Filed: Jan. 4, 2021

(65) Prior Publication Data

US 2021/0121163 A1 Apr. 29, 2021

Related U.S. Application Data

(63) Continuation of application No. 15/500,000, filed on Apr. 28, 2017, now Pat. No. 10,905,404.

(Continued)

(51) Int. Cl.
*A61B 10/02* (2006.01)
*A61B 10/00* (2006.01)

(52) U.S. Cl.
CPC ...... *A61B 10/0266* (2013.01); *A61B 10/0096* (2013.01); *A61B 10/0275* (2013.01);
(Continued)

(58) Field of Classification Search
CPC ............ A61B 10/0266; A61B 10/0096; A61B 10/0275; A61B 10/0283; A61B 2010/0208; A61B 2010/0225
See application file for complete search history.

(56) References Cited

U.S. PATENT DOCUMENTS

| | | |
|---|---|---|
| 5,526,822 A | 6/1996 | Burbank et al. |
| 5,928,164 A | 7/1999 | Burbank et al. |

(Continued)

FOREIGN PATENT DOCUMENTS

| | | |
|---|---|---|
| CN | 102846342 | 1/2013 |
| EP | 1952774 A1 | 8/2008 |

(Continued)

OTHER PUBLICATIONS

Hahn, Markus et al., *Vacuum-Assisted Breast Biopsy with Mammotome*, book, 2013, Springer Medizin Verlag; Germany.

(Continued)

*Primary Examiner* — Andrey Shostak
(74) *Attorney, Agent, or Firm* — Frost Brown Todd LLP

(57) ABSTRACT

A biopsy device includes a body, a needle, a cutter, an analysis area, a valve, and a tissue sample holder. The cutter is movable relative to the needle and in communication with the needle for transporting tissue samples. The analysis area is disposed proximally of the cutter and in communication with the needle to receive a tissue sample cut by the cutter for analysis by a user. The valve is disposed proximally of the analysis area and configured to alternate between an open configuration and a closed configuration. The tissue sample holder is disposed proximally of the valve and fixedly attached to the body. The valve is configured to permit analysis of the sample disposed in the analysis area when the valve is in the closed configuration and to permit (Continued)

the tissue sample to be passed into the tissue sample holder when the valve is in the open configuration.

19 Claims, 46 Drawing Sheets

Related U.S. Application Data

(60) Provisional application No. 62/329,346, filed on Apr. 29, 2016.

(52) U.S. Cl.
CPC .. *A61B 10/0283* (2013.01); *A61B 2010/0208* (2013.01); *A61B 2010/0225* (2013.01)

(56) References Cited

U.S. PATENT DOCUMENTS

| | | | |
|---|---|---|---|
| 6,017,316 A | 1/2000 | Ritchart et al. | |
| 6,086,544 A | 7/2000 | Hibner et al. | |
| 6,162,187 A | 12/2000 | Buzzard et al. | |
| 6,432,065 B1 | 8/2002 | Burdorff et al. | |
| 6,626,849 B2 | 9/2003 | Huitema et al. | |
| 6,752,768 B2 | 6/2004 | Burdorff et al. | |
| 7,442,171 B2 | 10/2008 | Stephens et al. | |
| 7,648,466 B2 | 1/2010 | Stephens et al. | |
| 7,837,632 B2 | 11/2010 | Stephens et al. | |
| 7,854,706 B2 | 12/2010 | Hibner | |
| 7,914,464 B2 | 3/2011 | Burdorff et al. | |
| 7,938,786 B2 | 5/2011 | Ritchie et al. | |
| 7,985,239 B2 | 7/2011 | Suzuki | |
| 8,083,687 B2 | 12/2011 | Parihar | |
| 8,105,243 B2 | 1/2012 | Vetter | |
| 8,118,755 B2 | 2/2012 | Hibner et al. | |
| 8,206,316 B2 | 6/2012 | Hibner et al. | |
| 8,241,226 B2 | 8/2012 | Hibner et al. | |
| 8,251,916 B2 | 8/2012 | Speeg et al. | |
| 8,337,415 B2 | 12/2012 | Trezza, II et al. | |
| 8,454,531 B2 | 6/2013 | Speeg et al. | |
| 8,532,747 B2 | 9/2013 | Nock et al. | |
| 8,672,860 B2 | 3/2014 | Moore et al. | |
| 8,702,623 B2 | 4/2014 | Parihar et al. | |
| 8,764,680 B2 | 6/2014 | Rhad et al. | |
| 8,801,742 B2 | 8/2014 | Rhad et al. | |
| 8,858,465 B2 | 10/2014 | Fiebig | |
| 8,938,285 B2 | 1/2015 | Fiebig et al. | |
| 8,986,222 B2 | 3/2015 | Miller et al. | |
| 9,095,326 B2 | 8/2015 | Ritchie et al. | |
| 9,326,755 B2 | 5/2016 | Fiebig et al. | |
| 9,345,457 B2 | 5/2016 | Speeg et al. | |
| 9,486,186 B2 | 11/2016 | Fiebig et al. | |
| 2005/0113716 A1* | 5/2005 | Mueller, Jr. | A61B 10/0041 600/568 |
| 2006/0074345 A1 | 4/2006 | Hibner | |
| 2009/0131821 A1 | 5/2009 | Speeg et al. | |
| 2010/0152610 A1 | 6/2010 | Parihar et al. | |
| 2010/0160819 A1 | 6/2010 | Parihar et al. | |
| 2010/0280409 A1 | 11/2010 | Mark | |
| 2011/0046455 A1 | 2/2011 | Hengerer et al. | |
| 2012/0283563 A1 | 11/2012 | Moore et al. | |
| 2013/0225943 A1* | 8/2013 | Holsing | A61B 8/0841 600/409 |
| 2013/0226027 A1 | 8/2013 | Hibner | |
| 2013/0324882 A1 | 12/2013 | Mescher | |
| 2014/0039343 A1* | 2/2014 | Mescher | A61B 90/98 600/562 |
| 2014/0257135 A1* | 9/2014 | DeFreitas | G01N 35/04 600/566 |
| 2014/0330163 A1* | 11/2014 | Ritchart | A61B 6/12 600/566 |
| 2016/0081585 A1 | 3/2016 | Halter | |

FOREIGN PATENT DOCUMENTS

| | | |
|---|---|---|
| EP | 2254126 A1 | 2/2013 |
| WO | WO 2007/112751 | 10/2007 |

OTHER PUBLICATIONS

Australian Office Action dated Feb. 15, 2021 for Application No. 2017258484, 8 pages.
Chinese Office Action dated Jan. 7, 2021 for Application No. 201780025090.1, 9 pages.
Chinese Office Action dated Jul. 23, 2021 for Application No. 201780025090.1, 10 pages.
Extended European Search Report dated Oct. 24, 2016 for Application No. 16168509.4, 7 pages.
European Communication dated Jul. 22, 2020 for Application No. 17733170.9, 6 pages.
Indian First Examination Report dated May 31, 2021 for Application No. 201817039388, 6 pages.
Korean Office Action dated Jul. 19, 2021 for Application No. 10-2018-7030845, 12 pages.
International Search Report and Written Opinion dated Sep. 8, 2017 for Application No. PCT/US2017/030076, 11 pgs.
United Kingdom Search report dated Nov. 9, 2016 for Application No. 1607881.8, 3 pages.
U.S. Appl. No. 62/329,346, filed Apr. 29, 2016.

* cited by examiner

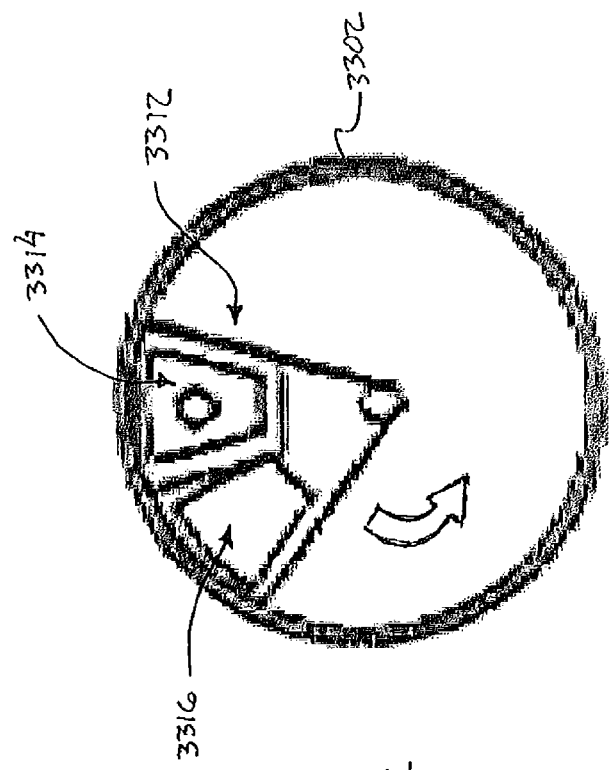
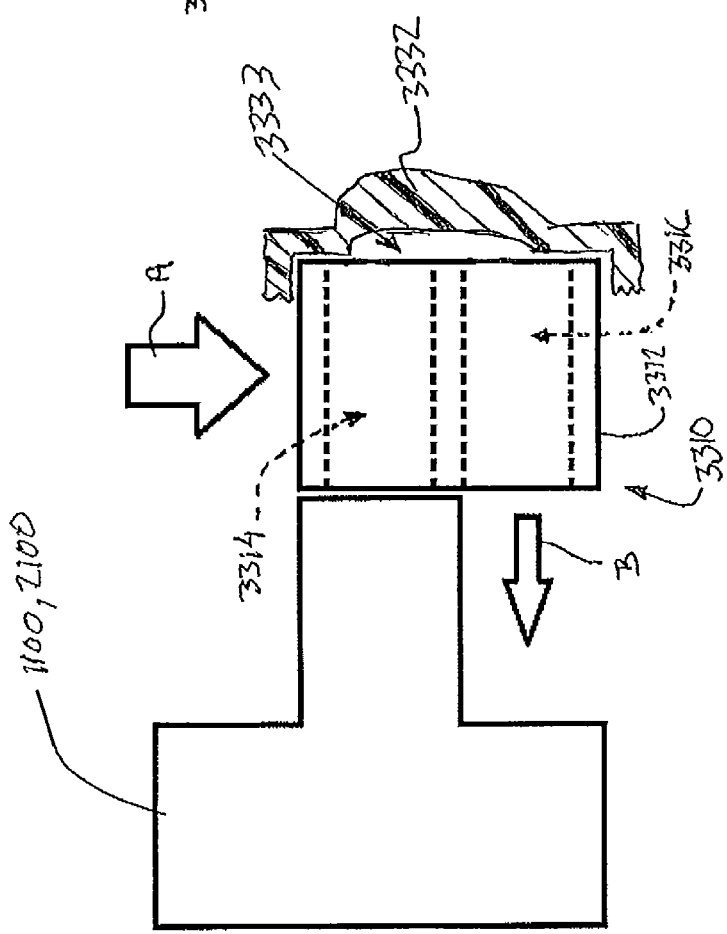
Fig. 27
Fig. 26

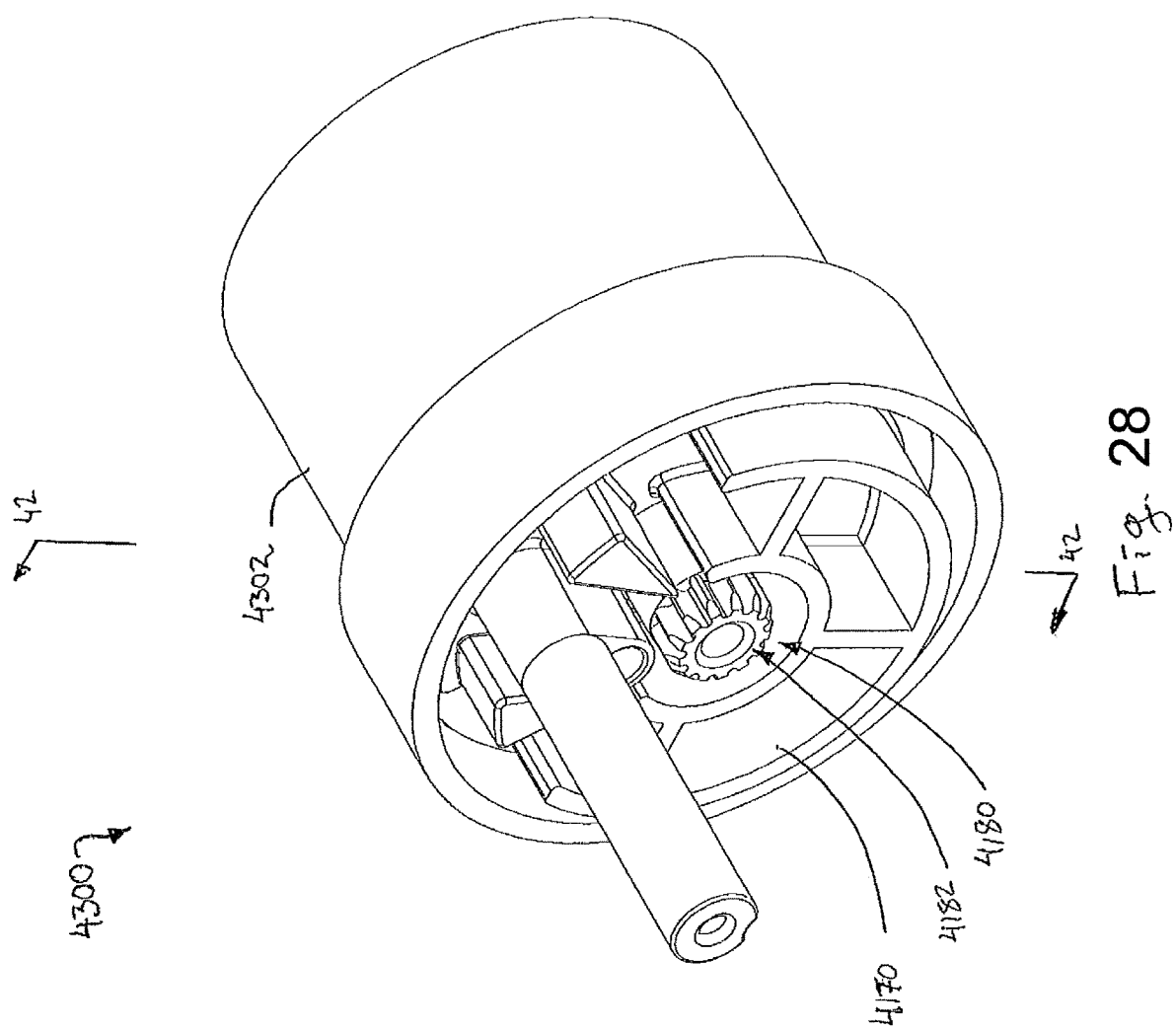

TISSUE SAMPLE HOLDER WITH ENHANCED FEATURES

PRIORITY

The present application is a continuation of U.S. Ser. No. 15/500,000, entitled "Tissue Sample Holder with Enhanced Features," filed Apr. 28, 2017, which claims priority to U.S. Provisional Patent Application No. 62/329,346, entitled "Tissue Sample Holder with Enhanced Features," filed on Apr. 29, 2016, the disclosures of which are hereby incorporated by reference in their entirety.

BACKGROUND

Biopsy samples have been obtained in a variety of ways in various medical procedures including open and percutaneous methods using a variety of devices. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device. Biopsy devices may be used under stereotactic guidance, ultrasound guidance, MRI guidance, Positron Emission Mammography ("PEM" guidance), Breast-Specific Gamma Imaging ("BSGI") guidance or otherwise.

The state of the art technology for conducting a breast biopsy is to use a vacuum-assisted breast biopsy device. A current textbook in this area is "Vacuum-Assisted Breast Biopsy with Mammotome®", available Nov. 11, 2012, copyright 2013 by Devicor Medical Germany GmBh, published in Germany by Springer Medizin Verlag, Authors: Markus Hahn, Anne Tardivon and Jan Casselman, ISBN 978-3-642-34270-7.

Merely exemplary biopsy devices and biopsy system components are disclosed in U.S. Pat. No. 5,526,822, entitled "Method and Apparatus for Automated Biopsy and Collection of Soft Tissue," issued Jun. 18, 1996; U.S. Pat. No. 5,928,164, entitled "Apparatus for Automated Biopsy and Collection of Soft Tissue," issued Jul. 27, 1999; U.S. Pat. No. 6,017,316, entitled "Vacuum Control System and Method for Automated Biopsy Device," issued Jan. 25, 2000; U.S. Pat. No. 6,086,544, entitled "Control Apparatus for an Automated Surgical Biopsy Device," issued Jul. 11, 2000; U.S. Pat. No. 6,162,187, entitled "Fluid Collection Apparatus for a Surgical Device," issued Dec. 19, 2000; U.S. Pat. No. 6,432,065, entitled "Method for Using a Surgical Biopsy System with Remote Control for Selecting an Operational Mode," issued Aug. 13, 2002; U.S. Pat. No. 6,626,849, entitled "MRI Compatible Surgical Biopsy Device," issued Sep. 11, 2003; U.S. Pat. No. 6,752,768, entitled "Surgical Biopsy System with Remote Control for Selecting an Operational Mode," issued Jun. 22, 2004; U.S. Pat. No. 7,442,171, entitled "Remote Thumbwheel for a Surgical Biopsy Device," issued Oct. 8, 2008; U.S. Pat. No. 7,648,466, entitled "Manually Rotatable Piercer," issued Jan. 19, 2010; U.S. Pat. No. 7,837,632, entitled "Biopsy Device Tissue Port Adjustment," issued Nov. 23, 2010; U.S. Pat. No. 7,854,706, entitled "Clutch and Valving System for Tetherless Biopsy Device," issued Dec. 1, 2010; U.S. Pat. No. 7,914,464, entitled "Surgical Biopsy System with Remote Control for Selecting an Operational Mode," issued Mar. 29, 2011; U.S. Pat. No. 7,938,786, entitled "Vacuum Timing Algorithm for Biopsy Device," issued May 10, 2011; U.S. Pat. No. 8,083,687, entitled "Tissue Biopsy Device with Rotatably Linked Thumbwheel and Tissue Sample Holder," issued Dec. 21, 2011; U.S. Pat. No. 8,118,755, entitled "Biopsy Sample Storage," issued Feb. 1, 2012; U.S. Pat. No. 8,206,316, entitled "Tetherless Biopsy Device with Reusable Portion," issued on Jun. 26, 2012; U.S. Pat. No. 8,241,226, entitled "Biopsy Device with Rotatable Tissue Sample Holder," issued on Aug. 14, 2012; U.S. Pat. No. 8,251,916, entitled "Revolving Tissue Sample Holder for Biopsy Device," issued Aug. 28, 2012; U.S. Pat. No. 8,454,531, entitled "Icon-Based User Interface on Biopsy System Control Module," published May 21, 2009, issued on Jun. 4, 2013; U.S. Pat. No. 8,532,747, entitled "Biopsy Marker Delivery Device," issued Sep. 10, 2013; U.S. Pat. No. 8,702,623, entitled "Biopsy Device with Discrete Tissue Chambers," issued on Apr. 22, 2014; U.S. Pat. No. 8,764,680, entitled "Handheld Biopsy Device with Needle Firing," issued on Jun. 11, 2014; U.S. Pat. No. 8,801,742, entitled "Needle Assembly and Blade Assembly for Biopsy Device," issued Aug. 12, 2014; U.S. Pat. No. 8,858,465, entitled "Biopsy Device with Motorized Needle Firing," issued Oct. 14, 2014; U.S. Pat. No. 8,938,285, entitled "Access Chamber and Markers for Biopsy Device," issued Jan. 20, 2015; U.S. Pat. No. 9,095,326, entitled "Biopsy System with Vacuum Control Module," issued Aug. 4, 2015 and U.S. Pat. No. 9,095,326, entitled "Biopsy System with Vacuum Control Module," issued Aug. 4, 2015. The disclosure of each of the above-cited U.S. patents is incorporated by reference herein.

Additional exemplary biopsy devices and biopsy system components are disclosed in U.S. Pat. Pub. No. 2006/0074345, entitled "Biopsy Apparatus and Method," published Apr. 6, 2006 and now abandoned; U.S. Pat. Pub. No. 2008/0214955, entitled "Presentation of Biopsy Sample by Biopsy Device," published Sep. 4, 2008; U.S. Pat. Pub. No. 2009/0131821, entitled "Graphical User Interface For Biopsy System Control Module," published May 21, 2009, now abandoned; U.S. Pat. Pub. No. 2010/0152610, entitled "Hand Actuated Tetherless Biopsy Device with Pistol Grip," published Jun. 17, 2010, now abandoned; U.S. Pat. Pub. No. 2010/0160819, entitled "Biopsy Device with Central Thumbwheel," published Jun. 24, 2010, now abandoned; U.S. Pat. Pub. No. 2013/0053724, entitled "Biopsy Device Tissue Sample Holder with Bulk Chamber and Pathology Chamber," published Feb. 28, 2013, will issue on May 3, 2016 as U.S. Pat. No. 9,326,755; U.S. Pat. Pub. No. 2013/0144188, entitled "Biopsy Device With Slide-In Probe," published Jun. 6, 2013; and U.S. Pat. Pub. No. 2013/0324882, entitled "Control for Biopsy Device," published Dec. 5, 2013. The disclosure of each of the above-cited U.S. patent application Publications, U.S. Non-Provisional patent Applications, and U.S. Provisional patent applications is incorporated by reference herein.

While several systems and methods have been made and used for obtaining a biopsy sample, it is believed that no one prior to the inventor has made or used the invention described in the appended claims.

BRIEF DESCRIPTION OF THE DRAWINGS

While the specification concludes with claims which particularly point out and distinctly claim this technology, it is believed this technology will be better understood from the following description of certain aspects taken in conjunction with the accompanying drawings, in which like reference numerals identify the same elements and in which:

FIG. 26 depicts another partial cut-away side view of the tissue sample holder of FIG. 21, with the sample management assembly in a second sample receiving configuration;

FIG. 27 depicts another front elevational view of the tissue sample holder of FIG. 21, with the sample basket removed and the sample management assembly in the second sample receiving configuration:

FIG. 28 depicts a perspective view of an exemplary alternative tissue sample holder for use with any one of the probes.

Figure 1:
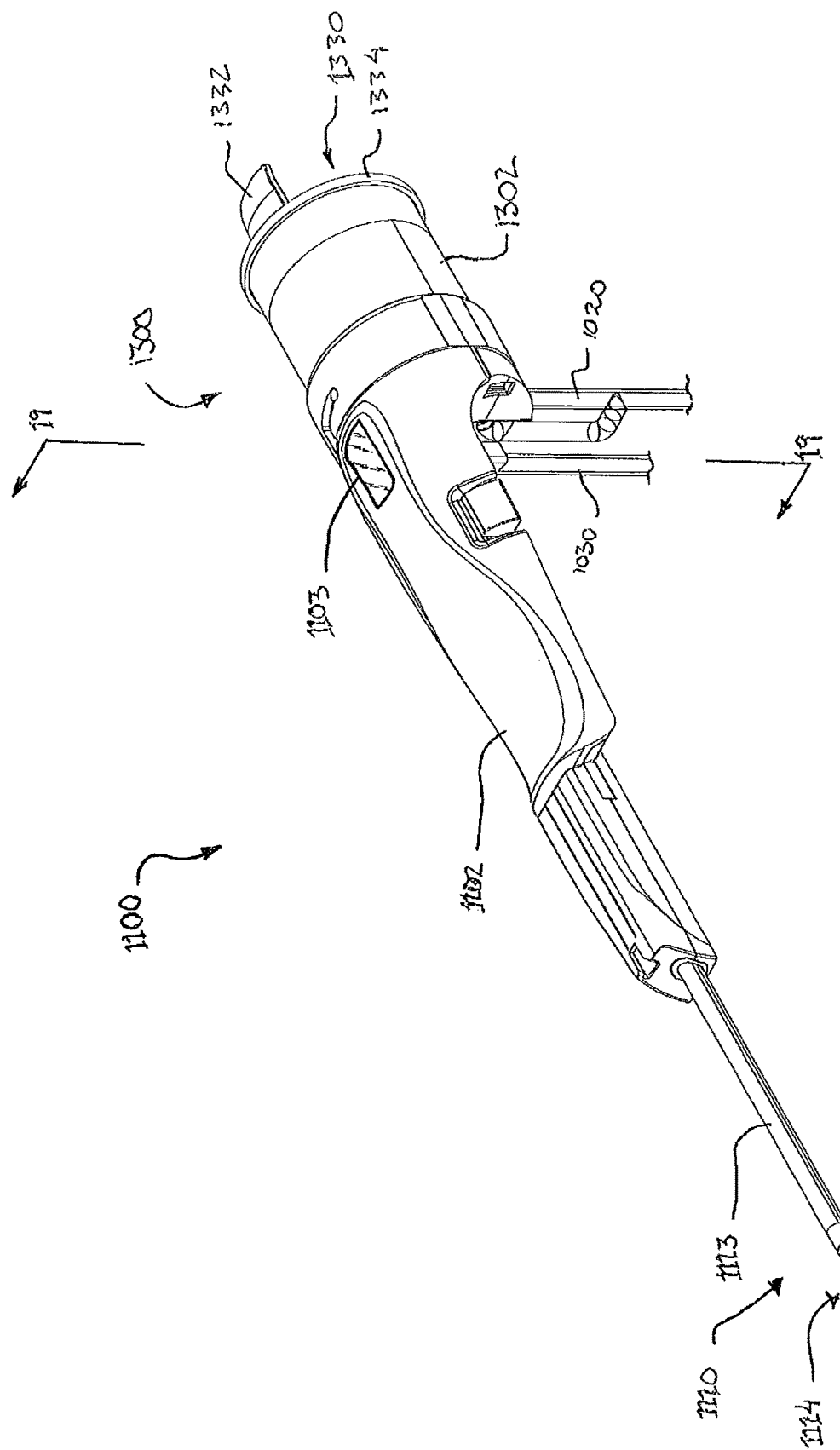
FIG. 1 depicts a perspective view of a probe for use with the biopsy device described and shown in FIGS. 1-12 of U.S. Pub. No. 2014/0039343, "Biopsy System", published on 6 Feb. 2014. The published US patent application is incorporated by reference in its entirety.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain aspects of the technology should not be used to limit its scope. Other aspects, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

FIGS. 1-12 of U.S. Pub. No. 2014/0039343, "Biopsy System", published on 6 Feb. 2014, describe an exemplary biopsy system. As previously stated, the published US patent application is incorporated by reference in its entirety.

FIG. 1 shows an exemplary alternative probe (1100) that can be readily incorporated into the biopsy device described in U.S. Pub. No. 2014/0039343. It should be understood that except as otherwise noted herein, probe (1100) is substantially the same as the probe described in U.S. Pub. No. 2014/0039343. Unlike the probe in U.S. Pub. No. 2014/0039343, probe (1100) of the present aspect is generally configured to permit individual analysis of a tissue sample using a tissue analysis feature that will be described in greater detail below. Probe (1100) is further configured to store tissue samples in a bulk configuration. As will be described in greater detail below, probe (1100) generally includes features to permit temporary isolation of a single tissue sample followed by deposit in a single bulk tissue chamber (1346).

Probe (1100) of the present aspect includes a needle (1110) extending distally from probe (1100) that is inserted into a patient's tissue to obtain tissue samples. These tissue samples are deposited in a tissue sample holder (1300) at the proximal end of probe (1100). As with respect to the probe described in U.S. Pub. No. 2014/0039343, a vacuum control module can be coupled with probe (1100) via a valve assembly and tubes (1020, 1030), which is operable to selectively provide vacuum, saline, atmospheric air, and venting to probe (1100). Probe (1100) also includes a top housing (1102) or body that generally defines an exterior surface of probe (1100) for gripping by an operator to manipulate needle (1110). Although not shown, it should be understood that probe (1100) includes gears or other feature similar to gears described in U.S. Pub. No. 2014/0039343. As with respect to the probe described in U.S. Pub. No. 2014/0039343, such gears and/or other features are operable to drive a cutter actuation mechanism in probe (1100) to rotate and translate a cutter (not shown) disposed within needle (1110).

Needle (1110) is substantially the same as the needle described in U.S. Pub. No. 2014/0039343. For instance, needle (1110) of the present aspect comprises a cannula (1113) having a piercing tip (1112), a lateral aperture (1114) located proximal to tip (1112). Although not shown, it should be understood that in some aspects needle (1110) also includes a hub member (not shown) similar to the hub member described in U.S. Pub. No. 2014/0039343. As similarly described in U.S. Pub. No. 2014/0039343 with respect to tip, tip (1112) of the needle (1110) is configured to pierce and penetrate tissue, without requiring a high amount of force, and without requiring an opening to be pre-formed in tissue prior to insertion of tip (1112).

Lateral aperture (1114) is also substantially similar to lateral aperture described in U.S. Pub. No. 2014/0039343. For instance, lateral aperture (1114) is sized to receive prolapsed tissue during operation of the biopsy device described in U.S. Pub. No. 2014/0039343. Although not shown, it should be understood that a hollow tubular cutter (not shown) is disposed within needle. The cutter in the present aspect is substantially similar to the cutter described in U.S. Pub. No. 2014/0039343 such that the cutter is operable to rotate and translate relative to needle (1110) and past lateral aperture (1114) to sever a tissue sample from tissue protruding through lateral aperture (1114). Needle (1110) of the present aspect is similar to the needle described in U.S. Pub. No. 2014/0039343 with respect to being rotated about the longitudinal axis of needle (1110) to orient lateral aperture (1114) at any desired axial position.

As described above, probe (1100) includes housing (1102), which supports the internal components of probe (1100). Needle (1110) protrudes distally from housing (1102) and is supported by housing (1102) such that an operator can manipulate needle (1110) by grasping housing (1102). Unlike the housing described in U.S. Pub. No. 2014/0039343, housing (1102) of the present aspect includes tissue window (1103). As will be described in greater detail below, tissue window (1103) provides a tissue analysis feature by providing a transparent window through which an individual tissues sample may be viewed by an operator.

Figure 2:
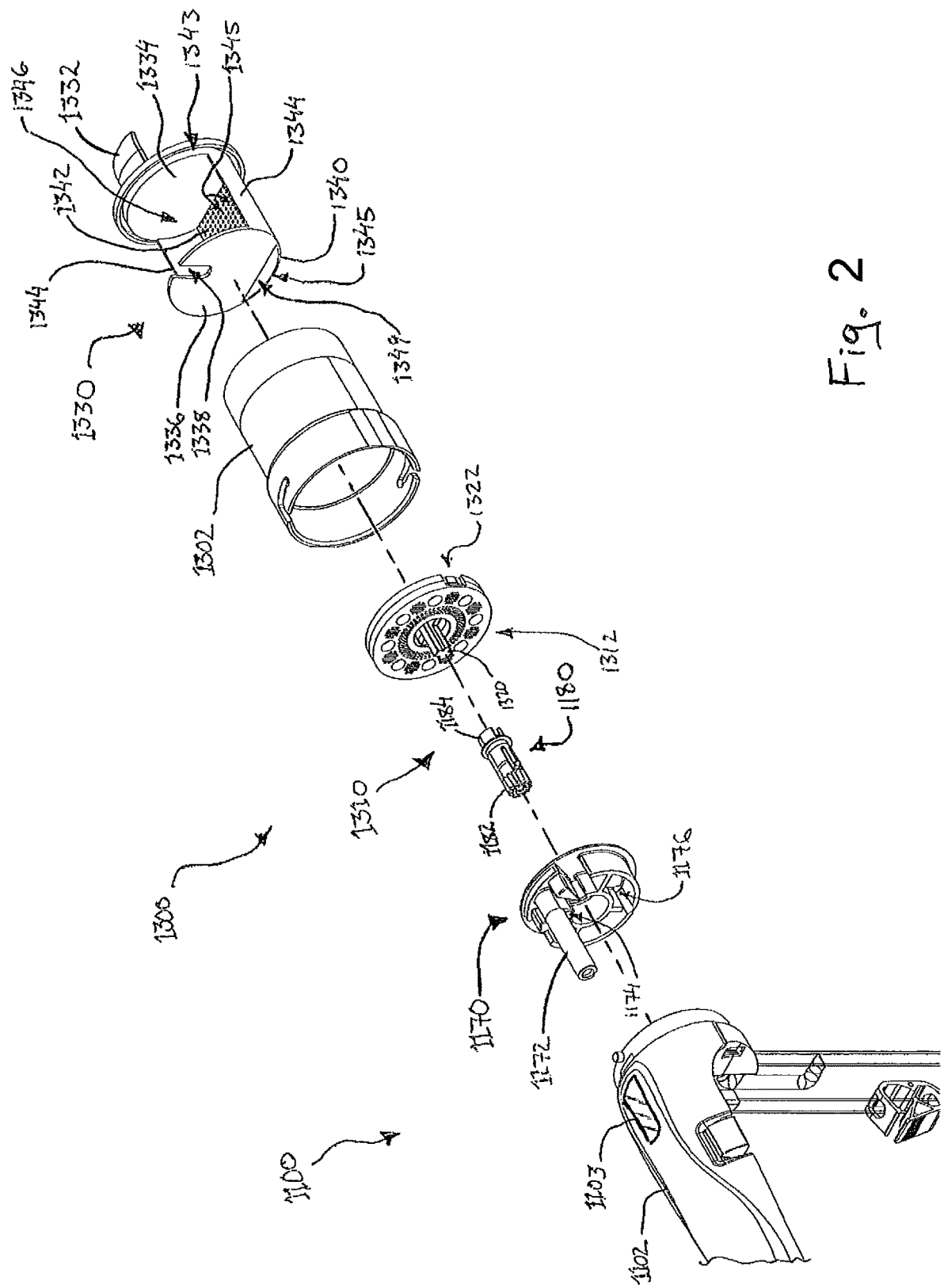
FIG. 2; depicts an exploded perspective view of a tissue sample holder of the probe of FIG. 1.

The proximal end of housing (1102) supports a tissue sample holder (1300) that is similar to the tissue sample holder described in U.S. Pub. No. 2014/0039343. However, unlike the tissue sample holder described in U.S. Pub. No. 2014/0039343, tissue sample holder (1300) of the present aspect is configured to store tissue samples in a single bulk tissue sample chamber (1346). As is best seen in FIG. 2, tissue sample holder (1300) comprises a sealing member (1170), a sample basket (1330), a sample management assembly (1310), and an outer cover (1302). Sealing member (1170) of the present aspect is substantially the same as the sealing member described in U.S. Pub. No. 2014/0039343.

Sealing member (1170) of the present aspect includes a longitudinally extending cutter seal (1172), which receives the cutter disposed in needle (1110) and seals against the exterior of the cutter. The proximal end of the cutter remains within cutter seal through the full range of travel of the cutter such that cutter seal (1172) maintains a fluid tight seal as the cutter is actuated for tissue sampling. Also like the sealing member described in U.S. Pub. No. 2014/0039343 with respect to the needle, an opening (not shown) is positioned at the proximal end of the cutter seal (1172). As will be described in greater detail below, this opening is configured to align with a particular portion of sample management assembly (1310) to transmit tissue samples to sample basket (1330).

Sealing member (1170) further includes a first vacuum opening (1174) and a second vacuum opening (1176). First vacuum opening (1174) is positioned below cutter seal (1172). First vacuum opening (1174) is substantially similar to the opening of sealing member described in U.S. Pub. No. 2014/0039343. However, unlike the sealing member described in U.S. Pub. No. 2014/0039343, sealing member (1170) of the present aspect additionally includes second vacuum opening (1176) disposed near the bottom of sealing member (1170). As will be described in greater detail below, first vacuum opening (1174) and second vacuum opening (1176) are both in communication with axial tube (1020) to supply vacuum to basket (1330) and the cutter of needle (1110).

Unlike the sealing member described in U.S. Pub. No. 2014/0039343, sealing member (1170) of the present aspect is comprised of a substantially transparent material. It should be understood that in the present aspect sealing member (1170) is substantially transparent to permit an operator to see a tissue sample disposed within sealing member (1170). As will be described in greater detail below, this feature is usable in conjunction with a tissue analysis feature that will be described in greater detail below. The term "substantially transparent" used herein should be understood to generally include a clear or see-through sealing member (1170). However, it should be understood that the term "substantially transparent" should not necessarily be limited to just being clear. For instance, in some aspects sealing member (1170) may include certain optical coatings that may have an impact on the transparency of sealing member (1170) by limiting certain wavelengths of light that penetrate sealing member (1170) to thereby enhance visualization or analysis of a tissue sample.

Figure 3:
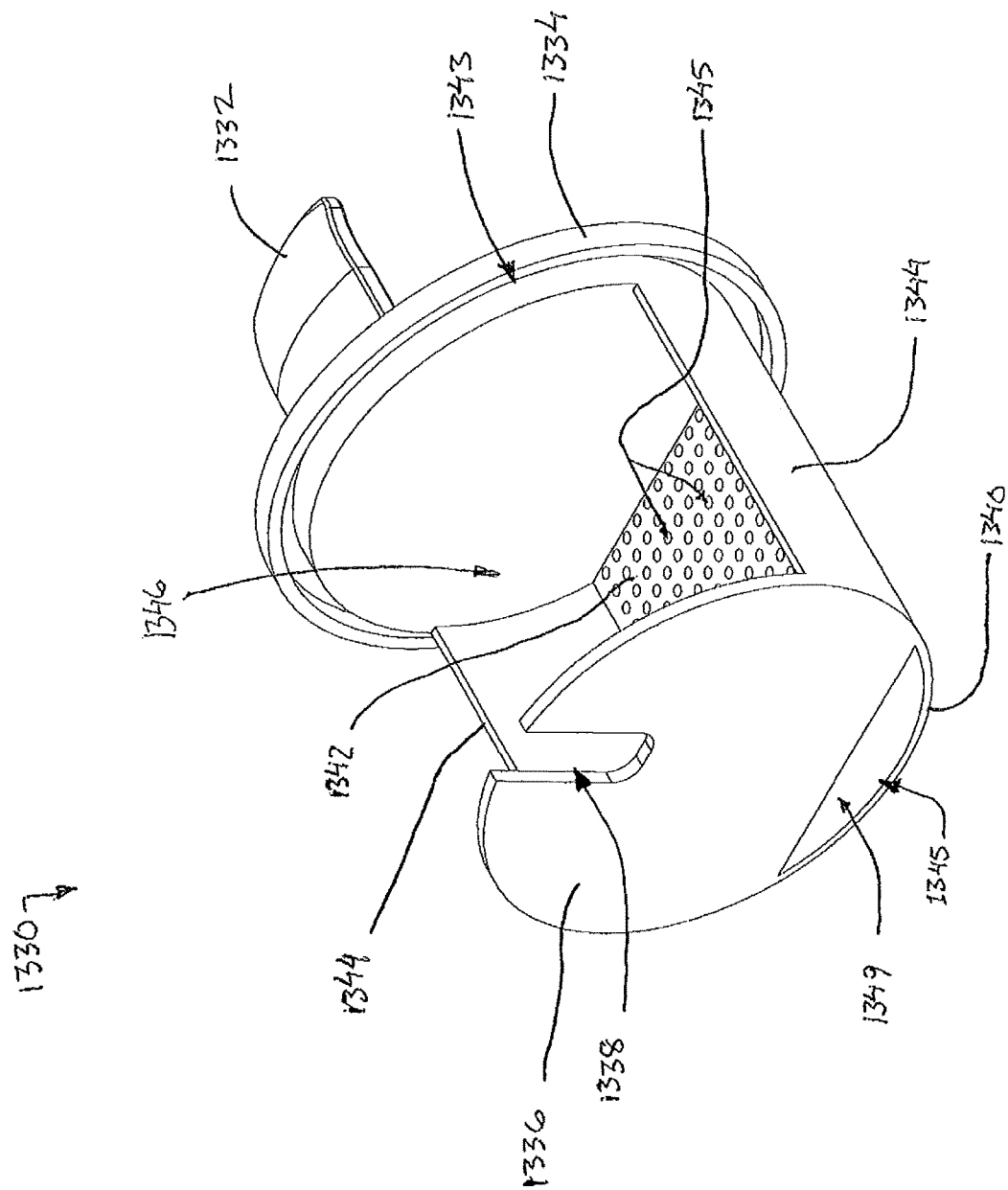
FIG. 3 depicts a perspective view of a sample basket of the tissue sample holder of FIG. 2.

Sample basket (1330) is best seen in FIG. 3. Basket (1330) is generally configured to hold a plurality of tissue samples in a single tissue sample chamber (1346). As can be seen, basket (1330) comprises a grip (1332), a proximal wall (1334). Grip (1332) extends proximally from proximal wall (1334) and is configured to be grasped by an operator to manipulate basket (1330). Proximal wall (1334) defines a channel (1343) along the outer edge of the distal side of proximal wall (1334). Channel (1343) is configured to receive at least a portion of outer cover (1302) to fluidly seal the proximal end of tissue sample holder (1300) when basket (1330) is disposed in outer cover (1302). Although not shown, it should be understood that channel (1343) can be equipped with gaskets or other sealing elements to further promote sealing between basket (1330) and outer cover (1302).

A pair of sidewalls (1344) and a lower floor (1340) extend distally from proximal wall (1334). In the present aspect, sidewalls (1344) and lower floor (1340) are defined by a single semi-circular shaped member. However, it should be understood that in other aspects sidewalls (1344) and lower floor (1340) are more discretely defined by a square or rectangular cross-section. Regardless, an intermediate floor (1342) is disposed above lower floor (1340). Lower floor (1340) and intermediate floor (1342) are parallel relative to each other and are spaced laterally from each other to define a vacuum passage (1349) therebetween. As will be described in greater detail below, vacuum passage (1349) is configured to communicate vacuum through a plurality of openings (1345) in intermediate floor (1342) to collect tissue samples.

A distal wall (1336) extends upwardly from the distal end of intermediate floor (1342). Distal wall (1336) further extends laterally from sidewalls (1344). Distal wall (1336) of the present aspect defines a semi-circular shape that is configured to abut sample management assembly (1310), as will be described in greater detail below. Distal wall (1336), proximal wall (1334), sidewalls (1344), and intermediate floor (1342) together define a tissue sample chamber (1346). Tissue sample chamber (1346) is generally configured to receive a plurality of tissue samples therein. In the present aspect, tissue sample chamber (1346) is configured to receive anywhere between about 20 to about 50 tissue samples. Of course, in other aspects tissue sample chamber (1346) may be configured to receive any other suitable number of tissue samples.

An upper portion of distal wall (1336) includes a tissue opening (1338) therein. Furthermore, because distal wall (1336) terminates below intermediate floor (1342), a vacuum opening (1347) is defined in the distal end of basket (1330) between intermediate floor (1342) and lower floor (1340). As will be described in greater detail below, tissue opening (1338) is generally configured to be selectively placed into communication with cutter and axial tube (1020) via sample management assembly (1310). Similarly, vacuum opening (1347) is generally configured to be selectively placed into communication with axial tube (1020) via sample management assembly (1310). The selective communication between tissue opening (1338) and vacuum opening (1347) generally permits tissue sample chamber (1346) to receive tissue samples therein when such tissue samples are acquired via needle (1110) and transported axially through the cutter.

Figure 4:
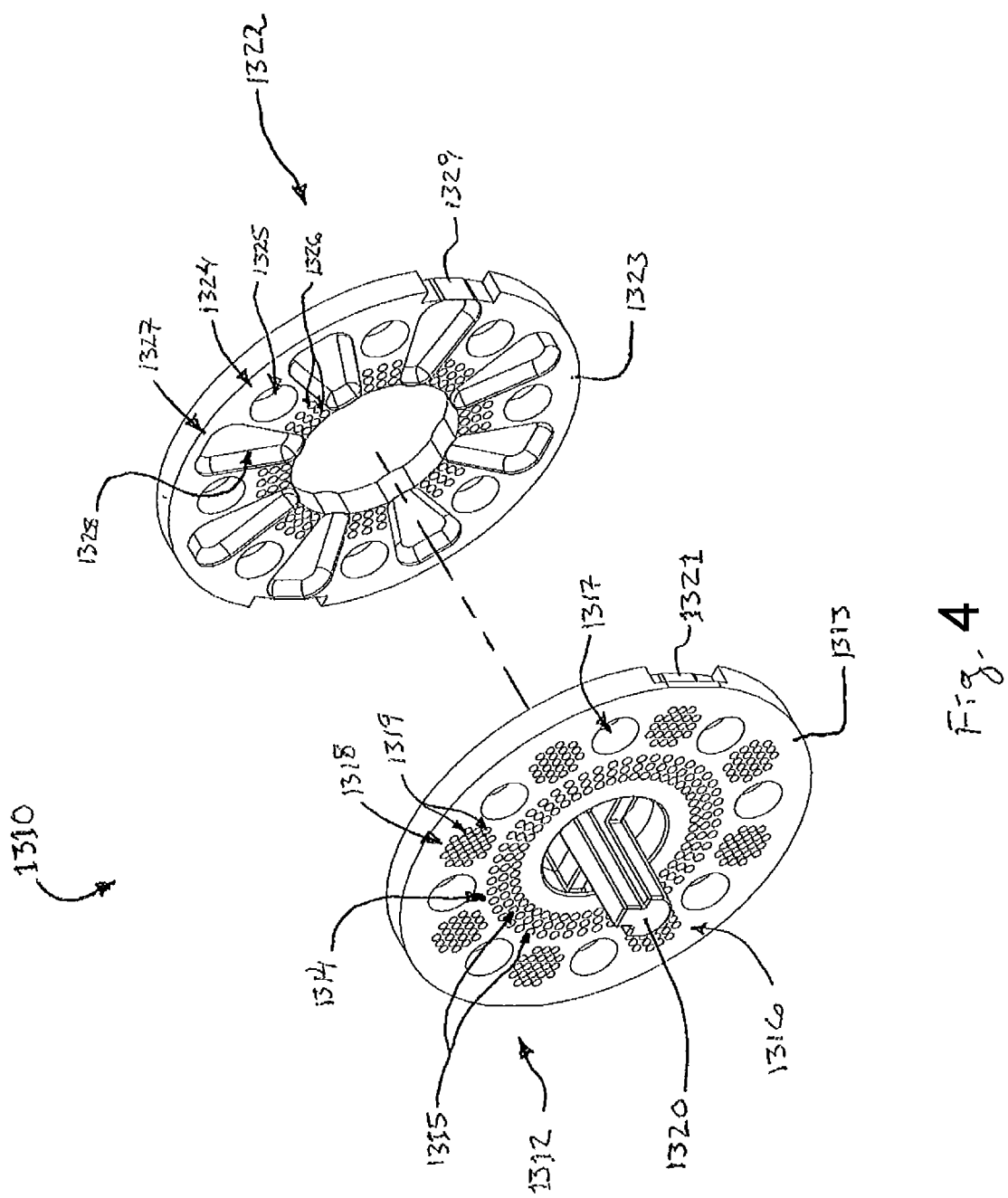
FIG. 4 depicts a perspective exploded view of a sample management assembly of the probe of FIG. 1.

Sample management assembly (1310) is shown in FIG. 4. As can be seen, sample management assembly (1310) comprises a first rotatable member (1312) and a second rotatable member (1322). First rotatable member (1312) comprises a generally coin shaped front screen body (1313). Front screen body (1313) defines an inner vacuum ring (1314) and an outer tissue manipulation ring (1316). Inner vacuum ring (1314) comprises a plurality of vacuum openings (1315) extending through front screen body (1313) and 360° around the inside of front screen body (1313). As will be described in greater detail below, vacuum openings (1315) are generally configured to communicate vacuum continuously from axial tube (1020) to the interior of the cutter disposed in needle (1110).

Outer tissue manipulation ring (1316) comprises an alternating array of filter portions (1318) and tissue openings (1317). In particular, each filter portion (1318) comprises an array of openings (1319) extending through front screen body (1313) arranged in a pattern generally corresponding to the outer diameter of the cutter disposed within needle (1110). As will be described in greater detail below, each filter portion (1318) is generally configured to prevent movement of a tissue sample through first rotatable member (1312), but permit the flow of vacuum and/or fluid. By contrast, tissue opening (1317) comprises a single opening extending through front screen body (1313) that is generally sized corresponding to the outer diameter of the cutter disposed within needle (1110). Thus tissue opening (1317) is generally configured to permit fluid, vacuum, and tissue samples to pass through front screen body (1313).

As described above, filter portions (1318) and tissue openings (1317) are arranged in an alternating ring shaped array about front screen body (1313). Each filter portion (1318) and tissue opening (1317) is positioned equidistantly about front screen body (1313) near the outer edge of front screen body (1313). It should be understood that each filter portion (1318) and tissue opening (1317) extends through front screen body (1313) in a direction that is parallel to an axis of rotation of front screen body (1313). Accordingly, as will be described in greater detail below, rotation of front screen body (1313) is generally configured to result in a particular filter portion (1318) or tissue opening (1317) being indexed with tissue opening (1338) of tissue sample holder (1300). As will also be described in greater detail below, this alternating relationship of filter portions (1318) and tissues openings (1317) is generally configured to permit sample management assembly (1310) to selectively block tissue samples from entering tissue sample holder (1300).

First rotatable member (1312) further comprises a central shaft (1320) and a pair of attachment features (1321). Central shaft (1320) is substantially similar to the central shaft as described in U.S. Pub. No. 2014/0039343 with respect to manifold. In particular, central shaft (1320) is configured to couple with a grasping feature (1184) of a rotation member (1180) (FIG. 2) to provide rotation of first rotatable member (1312) upon rotation of gear (1182). Of course, in other aspects any other suitable features for rotating first rotatable member (1312) may be used as will be apparent to those of ordinary skill in the art in view of the teachings herein.

Attachment features (1321) of the present aspect comprise an indentation of opposing sides of first rotatable member (1312). Attachment features (1321) permit fastening of first rotatable member (1312) to second rotatable member (1322). Thus, it should be understood that first rotatable member (1312) and second rotatable member (1322) are configured to rotate together in response to rotation of central shaft (1320). Although not shown, it should be understood that attachment features (1321) may include other additional features such as clips, retainers, fasteners, and/or etc. to promote attachment between first rotatable member (1312) and second rotatable member (1322).

Second rotatable member (1322), like first rotatable member (1312), comprises a generally coin shaped rear screen body (1323). Rear screen body (1323) includes an array of alternating tissue receiving portions (1324) and fluid portions (1327). Tissue receiving portions (1324) are generally configured to direct fluid and tissue through rear screen body (1323). In particular, each tissue receiving portion (1324) comprises a tissue opening (1325) and a plurality of vacuum openings (1326). Each tissue opening (1325) extends through rear screen body (1323) and corresponds in size to each tissue opening (1317) described above. As similarly described above with respect to tissue openings (1317), tissue openings (1325) of second rotatable member (1322) are generally sized to correspond to the outer diameter of the cutter disposed in needle (1110) such each tissue opening (1317) is configured to receive a tissue sample therethrough. As will be described in greater detail below, this permits a tissue sample to pass through first rotatable member (1312), then through second rotatable member (1322), before finally being deposited in tissue sample holder (1300).

Vacuum openings (1326) of each tissue receiving portion (1324) are configured to permit the flow of vacuum through rear screen body (1323) of second rotatable member (1322). As will be described in greater detail below, this permits vacuum and/or fluid to pass through second rotatable member (1322) and into tissue sample holder (1300). Vacuum in tissue sample holder (1300) is then transferred to the cutter disposed within needle (1110) via a respective tissue opening (1325).

Figure 5:
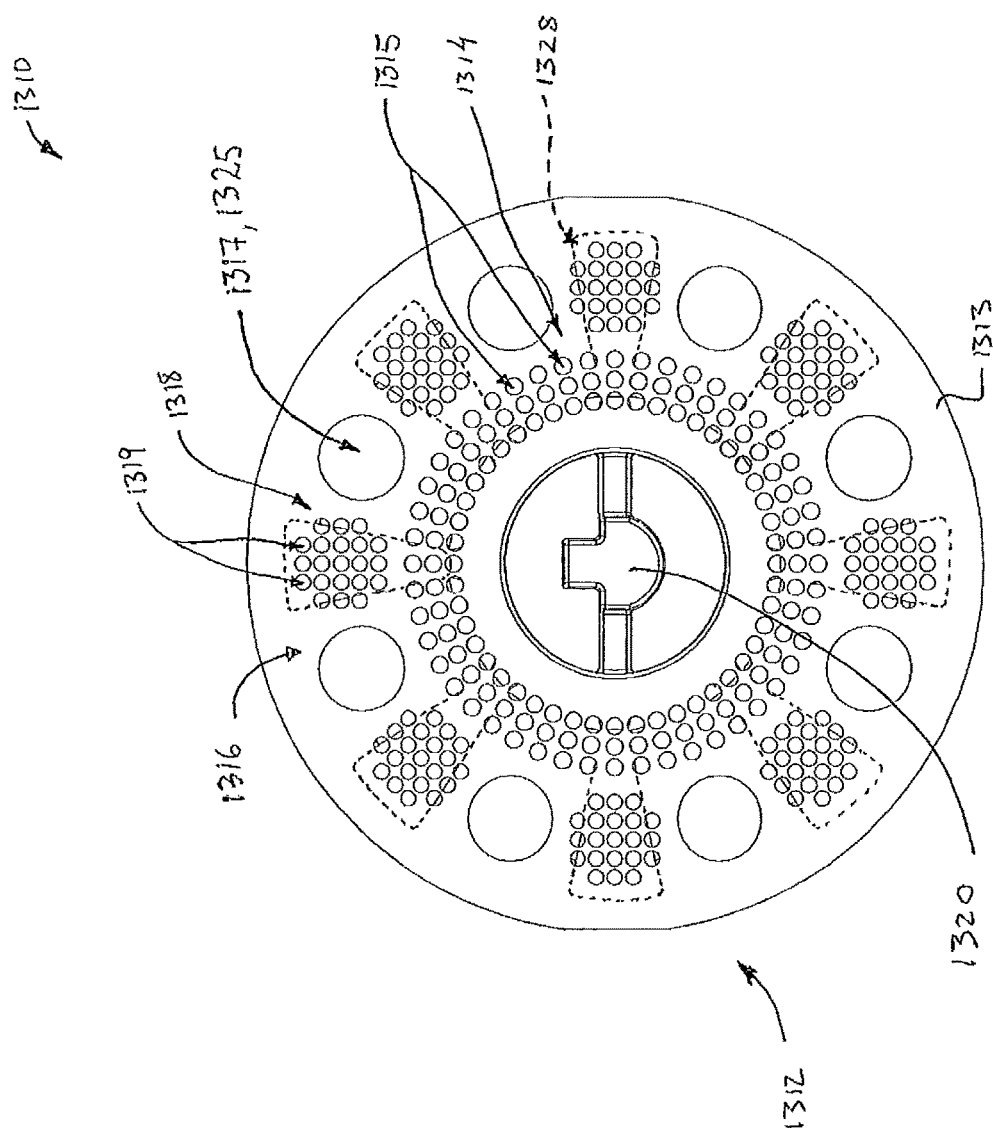
FIG. 5 depicts a front elevational view of the sample management assembly of FIG. 4.

Each fluid portion (1327) is generally configured to redirect fluid flow relative to second rotatable member (1322), thereby blocking flow of vacuum and/or fluid from entering tissue sample holder (1300). In particular, each fluid portion (1327) comprises a generally trapezoidally or tear drop-shaped recess (1328). The internal edges of each recess (1328) are rounded to promote fluid flow within each recess (1328). Of course, in other aspects the internal edges of each recess (1328) may be straight or include some other structural shape. Each angled leg of the trapezoidal shape of each recess (1328) is angled radially with the circular cross-sectional shape of rear screen body (1323). As best seen in FIG. 5, the inner and narrower portion of each recess (1328) is configured to communicate with vacuum openings (1315) of first rotatable member (1312). The outer and wider portion of each recess (1328) is configured to communicate with openings (1319) of a corresponding filter portion (1318) in first rotatable member (1312). Thus, as will be described in greater detail below, each recess (1328) is configured to redirect vacuum and/or fluid from vacuum openings (1315) of first rotatable member (1312) to openings (1319) of a corresponding filter portion (1318) in first rotatable member (1312).

Like with first rotatable member (1312) described above, second rotatable member (1322) likewise includes attachment features (1329) on opposing sides of rear screen body (1323). Like with attachment features (1321) described above, attachment features (1329) of the present aspect comprise an indentation in rear screen body (1323). Each attachment feature (1329) is configured to engage with a corresponding attachment feature (1321) of first rotatable member (1312) to secure second rotatable member (1322) to first rotatable member (1312). Thus, it should be understood that first rotatable member (1312) and second rotatable member (1322) are generally fixed together such that both first rotatable member (1312) and second rotatable member (1322) rotate together upon rotation of central shaft (1320).

Figure 6:
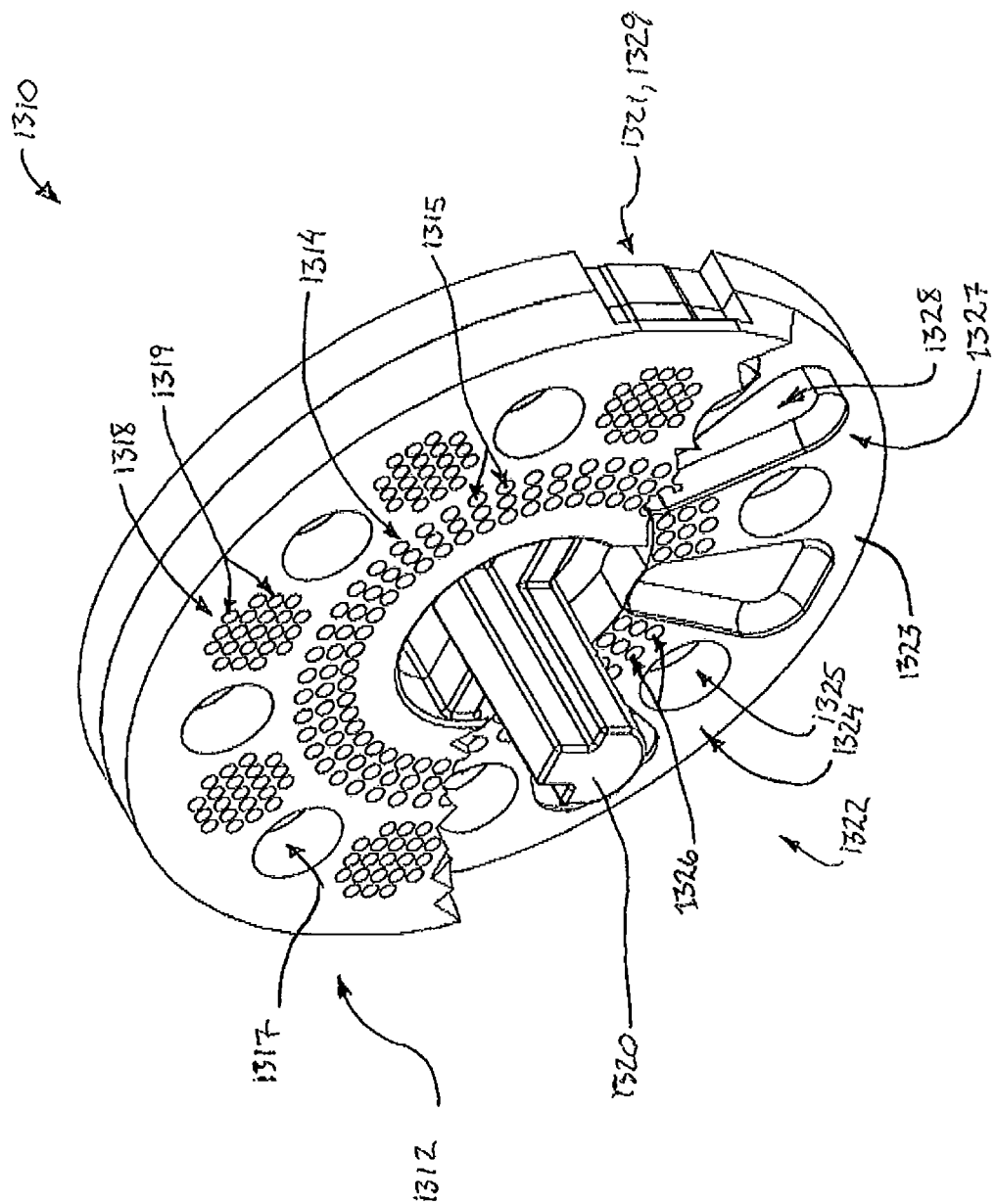
FIG. 6 depicts a perspective partial cut-away view of the sample management assembly of FIG. 4.

As can best be seen in FIG. 6, first rotatable member (1312) and second rotatable member (1322) are generally configured to fasten together. When fastened together, vacuum ring (1314) of first rotatable member (1312) is in communication with recesses (1328) and vacuum openings (1326) of second rotatable member (1322). Accordingly, when vacuum is communicated through a particular portion of vacuum ring (1314) vacuum will be communicated through vacuum openings (1315) of vacuum ring (1314) to either at a corresponding recess (1328) or array of vacuum openings (1326) of second rotatable member (1322).

As can also be seen in FIG. 6, each tissue opening (1317) of first rotatable member (1312) is in communication with a corresponding tissue opening (1325) of second rotatable member (1322). Likewise, each filter portion (1318) of first rotatable member (1312) is in communication with a corresponding recess (1328) of second rotatable member (1322). Thus, as first rotatable member (1312) alternates between filter portion (1318) and tissue opening (1317), there is a corresponding alternation between communication with a corresponding recess (1328) and tissue opening (1325) of second rotatable member (1322). As will be described in greater detail below, this alternating relationship permits sample management assembly (1310) to selectively enable and disable communication of tissue sample holder (1300) with the cutter disposed within needle (1110).

Figure 7:
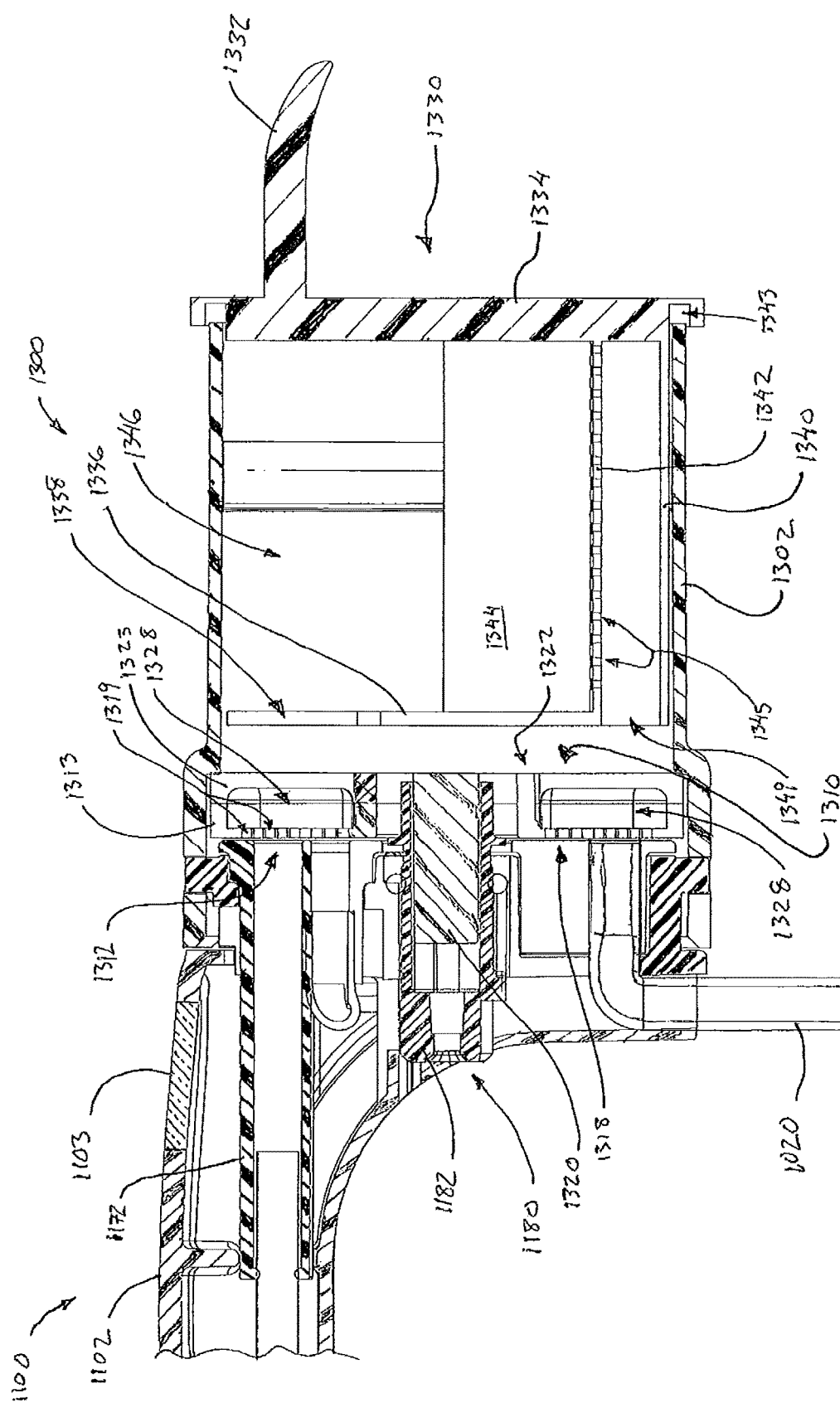
FIG. 7 depicts a depicts a side cross-sectional view of the probe of FIG. 1, with the cross-section taken along line 19-19 of FIG. 1 and the sample management assembly in a tissue blocking configuration.
Figure 8:
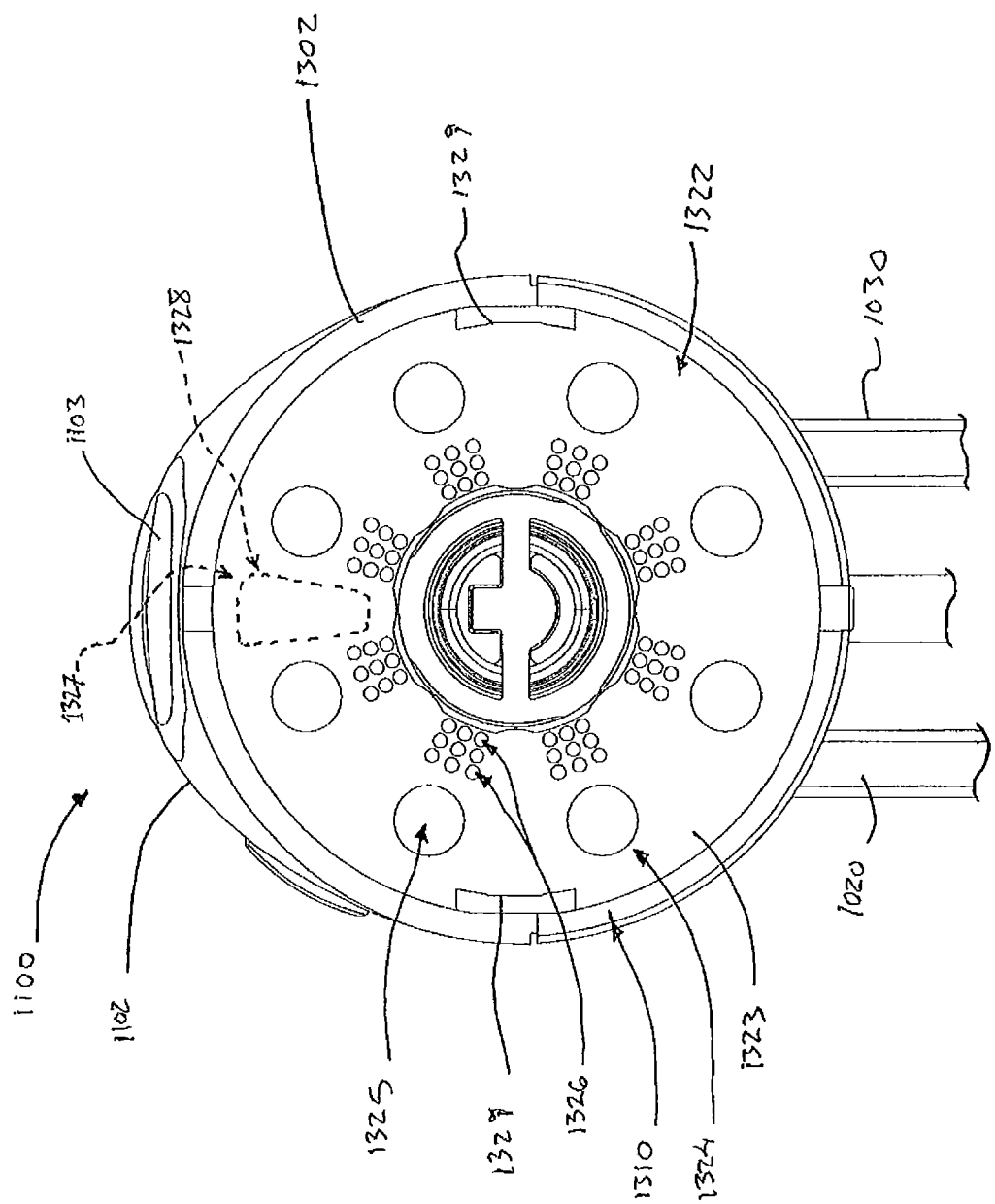
FIG. 8 depicts a rear elevational view of the probe of FIG. 1, with the sample basket of FIG. 3 removed and the sample management assembly in a tissue blocking configuration.

FIGS. 7-10 show an exemplary operation of sample management assembly (1310) to collect tissue samples in tissue sample holder (1300). In particular, as can be seen in FIGS. 7 and 8, sample management assembly (1310) initially begins in a sample blocking state. In the sample blocking state, sample management assembly (1310) is rotated to align filter portion (1318) of first rotatable member (1312) with cutter seal (1172) of sealing member (1170).

Because filter portion (1318) comprises an array of vacuum openings (1319), tissue samples are generally blocked from entering tissue sample holder (1300) by filter portion (1318). In addition, while in the blocking state, vacuum ring (1314) of first rotatable member (1312) is aligned with vacuum opening (1174) of sealing member (1170), thereby permitting vacuum from axial tube (1020) to pass through vacuum opening (1174) of sealing member (1170) and vacuum openings (1315) in vacuum ring (1314) of first rotatable member (1312).

Also in the blocking state, second rotatable member (1322) is rotated such that a recess (1328) corresponding to the given filter portion (1318) is aligned with cutter seal (1172) and vacuum opening (1174) of sealing member (1170). Because vacuum opening (1174) is in communication with axial tube (1020), vacuum will be communicated through axial tube (1020), through vacuum openings (1315) of vacuum ring (1314), and into recess (1328). Vacuum is then directed through recess (1328) to openings (1319) in filter portion (1318) of first rotatable member (1312) and into cutter seal (1172) of sealing member (1170) before finally being communicated to the cutter disposed in needle (1110). Thus, it should be understood that when sample management assembly (1310) is in the tissue blocking state, vacuum is directed through sample management assembly (1310) to the cutter without passing through tissue sample holder (1300).

When the cutter is used to collect a tissue sample while sample management assembly (1310) is in the blocking state, the tissue sample is transported through cutter to cutter seal (1172) of sealing member (1170) using vacuum that is redirected through recess (1328) of second rotatable member (1322). Filter portion (1318) blocks further movement of the tissue sample, thereby maintaining the tissue sample within cutter seal (1172) of sealing member (1170). Because sealing member (1170) of the present aspect is generally transparent, the tissue sample can be viewed and at least partially analyzed through tissue window (1103) in housing (1102) of probe (1100).

Figure 9:
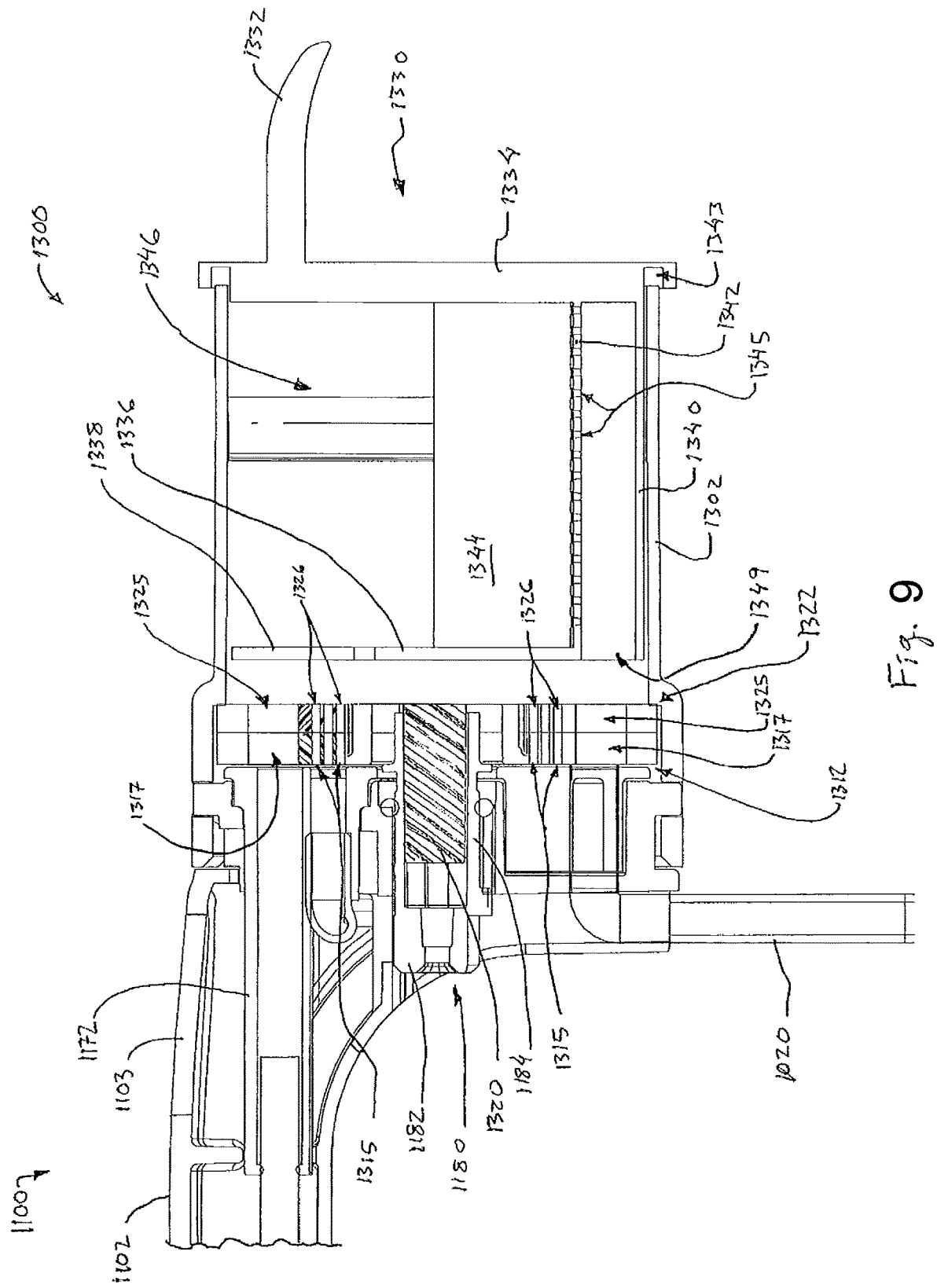
FIG. 9 depicts another cross-sectional view of the probe of FIG. 1, with the sample management assembly in a tissue transport configuration.
Figure 10:
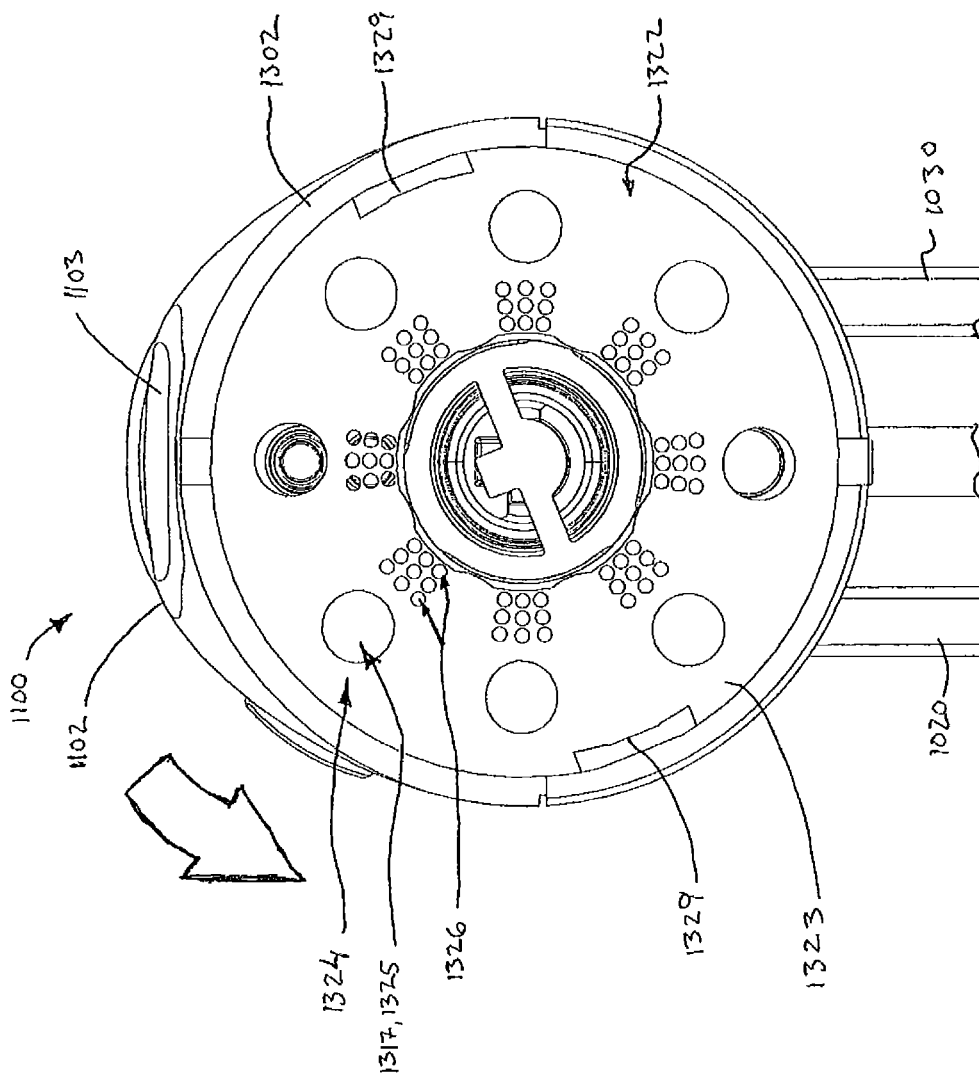
FIG. 10 depicts another rear elevational view of the probe of FIG. 1, with the sample basket of FIG. 3 removed and the sample management assembly in a tissue transport configuration.

To communicate tissue samples to tissue sample holder (1300), sample management assembly (1310) is rotated to a tissue transport position as shown in FIGS. 9 and 10. To transition sample management assembly (1310) to the tissue transport position, first rotatable member (1312) and second rotatable member (1322) are indexed to align the next adjacent tissue opening (1317, 1325) with the cutter disposed with needle (1110). In particular, as can be seen in FIG. 9, first rotatable member (1312) is rotated to align a given tissue opening (1317) with cutter seal (1172) of sealing member (1170). Vacuum ring (1314) remains aligned with first vacuum opening (1174) of sealing member (1170), but new openings (1315) are exposed due to rotation of first rotatable member (1312). Another tissue opening (1317) on the opposite side of first rotatable member (1312) is also aligned with second vacuum opening (1176) of cutter seal (1172).

As first rotatable member (1312) is rotated, second rotatable member (1322) is also rotated to index the next adjacent tissue opening (1325) with the cutter disposed in needle (1110) via sealing member (1170). Because tissue openings (1317, 1325) of first rotatable member (1312) and second rotatable member (1322) are indexed with the cutter disposed within needle (1110) via sealing member (1170) tissue samples severed by the cutter can travel through tissue openings (1317, 1325) and into tissue sample chamber (1346) of tissue sample holder (1300). In particular, to communicate a tissue sample into tissue sample holder (1300), vacuum passes from axial tube (1020) into first and second vacuum opening (1174, 1176) of sealing member (1170). Vacuum traveling through first vacuum opening (1174) of sealing member (1170) then is communicated through the vacuum openings (1315) in vacuum ring (1314) of first rotatable member (1312) and vacuum openings (1326) in second rotatable member (1322). From vacuum openings (1326) in second rotatable member (1322), vacuum travels into tissue sample holder (1300) where negative pressure builds to induce vacuum through the tissue openings (1317, 1325) of first and second rotatable members (1312, 1322) that are in communication with cutter seal (1172) of sealing member (1170).

In addition to the vacuum path described above, vacuum traveling through second vacuum opening (1176) of sealing member (1170) is communicated through the tissue openings (1317, 1325) of first and second rotatable members (1312, 1322) that are in communication with second vacuum opening (1176). This vacuum is then directed through vacuum opening (1347) of basket (1330) and through vacuum passage (1349). Vacuum can then travel upwardly through openings (1345) in intermediate floor (1342) of basket (1330). Such communication of vacuum through intermediate floor (1342) may in some aspects direct tissue samples downwardly into the bottom of basket (1330). In addition, excess fluids collected during a biopsy procedure may be evacuated from tissue sample holder (1300) through intermediate floor (1342).

Once a tissue sample has been collected in tissue sample holder (1300), sample management assembly (1310) may be rotated again to transition back to the tissue blocking position described above. Because the various features of first rotatable member (1312) and second rotatable member (1322) are disposed in an alternating configuration, it should be understood that sample management assembly (1310) may be rotated in any direction to transition between the tissue blocking position and the tissue transport position. In some aspects, first rotatable member (1312) and second rotatable member (1322) are successively rotated in a single direction to transition sample management assembly (1310) between the tissue blocking position and the tissue transport position. Of course, such a mode of operation is merely optional and in other aspects first rotatable member (1312) and second rotatable member (1322) may be rotated through any suitable sequence in any suitable direction.

In some circumstances it may be desirable to include within a biopsy device other forms of tissue sample analysis in addition to or in lieu of the visual analysis described in U.S. Pub. No. 2014/0039343 with respect to probe (1100). For instance, in some aspects bioimpedance sensors can be used to identify certain physical characteristics of a tissue sample. For purposes of this patent application "bioimpedance sensors" are defined as "sensors that measure how mammalian tissue opposes a tiny applied alternating current". In such aspects, sensors can be positioned within a biopsy device to obtain impedance measurements of a given tissue sample. These impedance measurements can then be compared to known impedance values of healthy and anomalous tissue to identify whether the given tissue sample might include any anomalies (e.g., calcifications, etc.).

Exemplary probes utilizing bioimpedance for tissue sample analysis are described below. It should be understood that the various alternative probes described below may be readily incorporated into the biopsy device as described in U.S. Pub. No. 2014/0039343. It should also be understood that the various components and probe described above and/or in U.S. Pub. No. 2014/0039343 may be readily incorporated into the alternative probes described below. Various suitable ways in which the above and below teachings may be combined will be apparent to those of ordinary skill in the art in view of the teachings herein. It should also be understood that the following teachings may be readily combined with the various teachings of the references that are cited herein.

Figure 11:
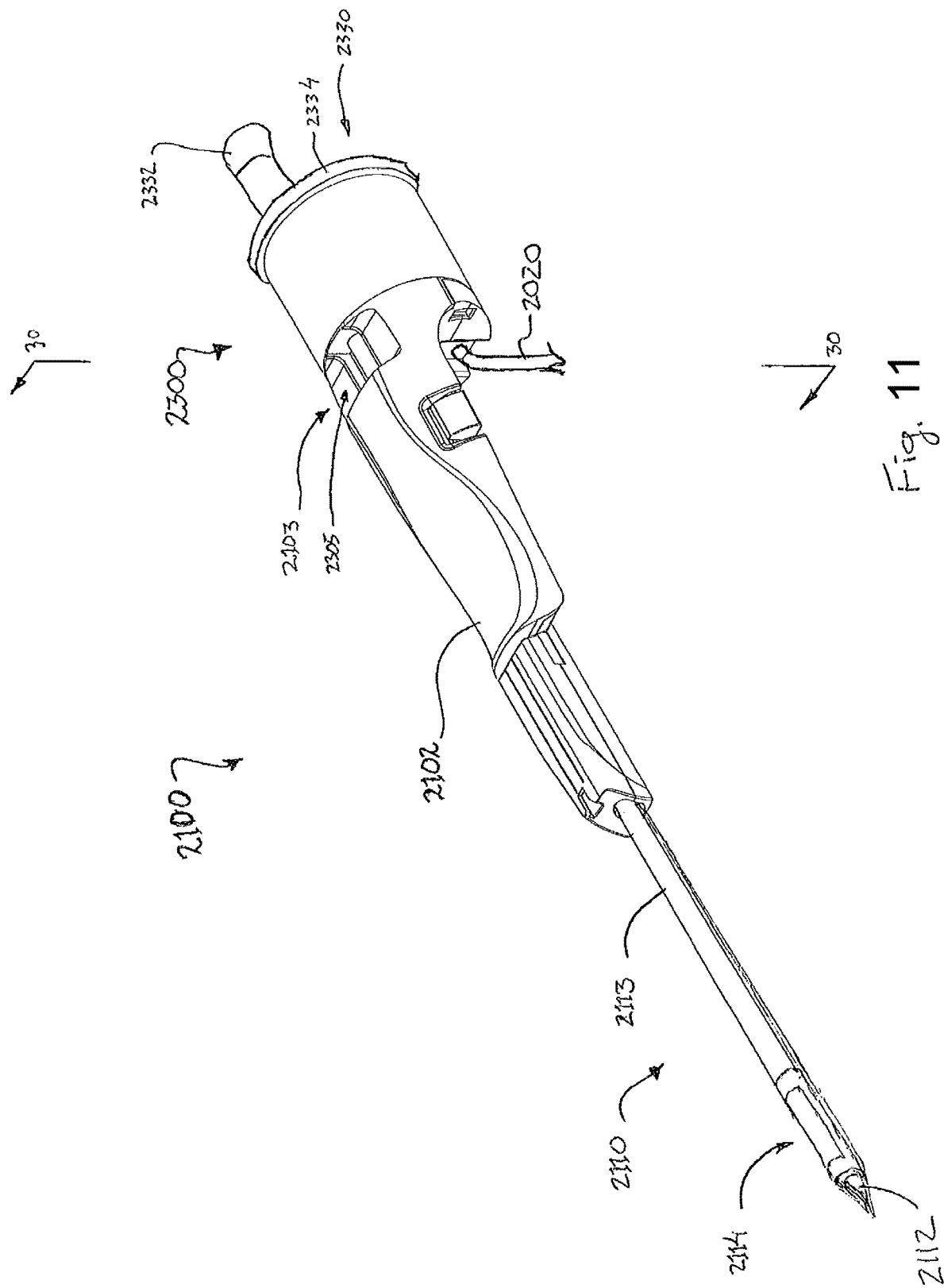
FIG. 11 depicts a perspective view of an alternative probe for use with the biopsy device of FIG. 2.

FIG. 11 shows an exemplary alternative probe (2100) that can be readily incorporated into the biopsy device as described in U.S. Pub. No. 2014/0039343. It should be understood that except as otherwise noted herein, probe (2100) is substantially the same as probe described in U.S. Pub. No. 2014/0039343. Unlike the probe in U.S. Pub. No. 2014/0039343, probe (2100) of the present aspect is generally configured to permit individual analysis of a tissue sample using another tissue analysis feature that will be described in greater detail below. Probe (2100) is further configured to store tissue samples in a bulk configuration. As will be described in greater detail below, probe (2100) generally includes features to permit temporary isolation of a single tissue sample followed by deposit in a single bulk tissue chamber (2346).

Probe (2100) of the present aspect includes a needle (2110) extending distally from probe (2100) that is inserted into a patient's tissue to obtain tissue samples. These tissue samples are deposited in a tissue sample holder (2300) at the proximal end of probe (2100). As similarly described in U.S. Pub. No. 2014/0039343 with respect to the probe, the vacuum control module can be coupled with probe (2100) via a valve assembly and one or more tubes (2020), which is operable to selectively provide vacuum, saline, atmospheric air, and venting to probe (2100). Probe (2100) also includes a top housing (2102) or body that generally defines an exterior surface of probe (2100) for gripping by an operator to manipulate needle (2110). Although not shown, it should be understood that probe (2100) includes gears or other feature similar to the gears described in U.S. Pub. No. 2014/0039343. As similarly described in U.S. Pub. No. 2014/0039343 with respect to the probe, such gears and/or other features are operable to drive a cutter actuation mechanism in probe (2100) to rotate and translate a cutter (not shown) disposed within needle (2110). Additionally, such gears and/or other features are operable to drive tissue sample holder (2300) as will be described in greater detail below.

Needle (2110) is substantially the same as the needle described above and/or in U.S. Pub. No. 2014/0039343. For instance, needle (2110) of the present aspect comprises a cannula (2113) having a piercing tip (2112), a lateral aperture (2114) located proximal to tip (2112). Although not shown, it should be understood that in some aspects needle (2110) also includes a hub member (not shown) similar to the hub member described in U.S. Pub. No. 2014/0039343. As similarly described as the tip in U.S. Pub. No. 2014/0039343, tip (2112) of the present aspect is configured to pierce and penetrate tissue, without requiring a high amount of force, and without requiring an opening to be pre-formed in tissue prior to insertion of tip (2112).

Lateral aperture (2114) is also substantially similar to the lateral aperture described in U.S. Pub. No. 2014/0039343. For instance, lateral aperture (2114) is sized to receive prolapsed tissue during operation of biopsy device. Although not shown, it should be understood that a hollow tubular cutter (not shown) is disposed within needle. The cutter in the present aspect is substantially similar to the cutter described in U.S. Pub. No. 2014/0039343 such that the cutter is operable to rotate and translate relative to needle (2110) and past lateral aperture (2114) to sever a tissue sample from tissue protruding through lateral aperture (2114). Also as similarly described as the needle in U.S. Pub. No. 2014/0039343, needle (2110) of the present aspect is configured to be rotated about the longitudinal axis of needle (2110) to orient lateral aperture (2114) at any desired axial position.

As described above, probe (2100) includes housing (2102), which supports the internal components of probe (2100). Needle (2110) protrudes distally from housing (2102) and is supported by housing (2102) such that an operator can manipulate needle (2110) by grasping housing (2102). Unlike the housing described in U.S. Pub. No. 2014/0039343, housing (2102) of the present aspect includes a tissue analysis portion (2103). As will be described in greater detail below, tissue analysis portion (2103) provides a tissue analysis feature that utilizes bioimpedance to analyze tissue samples. Additionally, in some aspects at least a portion of tissue analysis portion (2103) may be transparent to provide a means for individual tissues samples to be analyzed by visual inspection in addition to bioimpedance.

Figure 12:
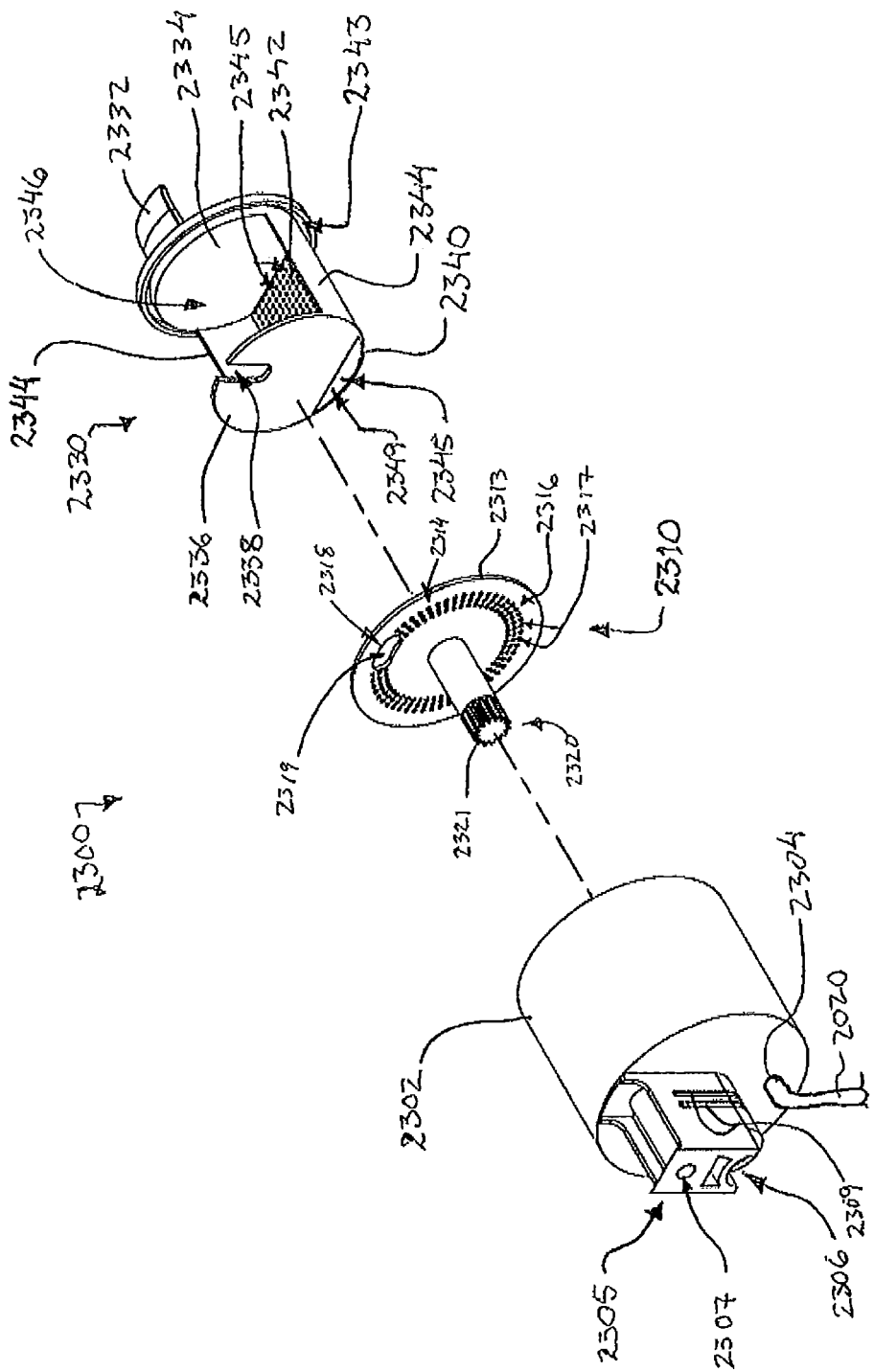
FIG. 12 depicts an exploded perspective view of a tissue sample holder for use with the probe of FIG. 11.

The proximal end of housing (2102) supports a tissue sample holder (2300) that is similar to the tissue sample holder described in U.S. Pub. No. 2014/0039343. However, unlike the tissue sample holder described in U.S. Pub. No. 2014/0039343, tissue sample holder (2300) of the present aspect is configured to store tissue samples in a single bulk tissue sample chamber (2346). As is best seen in FIG. 12, tissue sample holder (2300) comprises a sample basket (2330), a sample management assembly (2310), and an outer cover (2302). Sample basket (2330) is substantially similar to the sample basket described in U.S. Pub. No. 2014/0039343. For instance, basket (2330) is generally configured to hold a plurality of tissue samples in a single tissue sample chamber (2346). As can be seen, basket (2330) comprises a grip (2332) and a proximal wall (2334). Grip (2332) extends proximally from proximal wall (2334) and is configured to be grasped by an operator to manipulate basket (2330). Proximal wall (2334) defines a channel (2343) along the outer edge of the distal side of proximal wall (2334). Channel (2343) is configured to receive at least a portion of outer cover (2302) to fluidly seal the proximal end of tissue sample holder (2300) when basket (2330) is disposed in outer cover (2302). Although not shown, it should be understood that channel (2343) can be equipped with gaskets or other sealing elements to further promote sealing between basket (2330) and outer cover (2302).

A pair of sidewalls (2344) and a lower floor (2340) extend distally from proximal wall (2334). In the present aspect, sidewalls (2344) and lower floor (2340) are defined by a single semi-circular shaped member. However, it should be understood that in other aspects sidewalls (2334) and lower floor (2340) are more discretely defined by a square or rectangular cross-section. Regardless, an intermediate floor (2342) is disposed above lower floor (2340). Lower floor (2340) and intermediate floor (2342) are parallel relative to each other and are spaced laterally from each other to define a vacuum passage (2349) therebetween. As will be described in greater detail below, vacuum passage (2349) is configured to communicate vacuum through a plurality of openings (2345) in intermediate floor (2342) to collect tissue samples.

A distal wall (2336) extends upwardly from the distal end of intermediate floor (2342). Distal wall (2336) further extends laterally from sidewalls (2344). Distal wall (2336) of the present aspect defines a semi-circular shape that is configured to abut sample management assembly (2310), as will be described in greater detail below. Distal wall (2336), proximal wall (2334), sidewalls (2344), and intermediate floor (2342) together define a tissue sample chamber (2346). Tissue sample chamber (2346) is generally configured to receive a plurality of tissue samples therein. In the present aspect, tissue sample chamber (2346) is configured to receive anywhere between about 20 to about 50 tissue samples. Of course, in other aspects tissue sample chamber (2346) may be configured to receive any other suitable number of tissue samples.

An upper portion of distal wall (2336) includes a tissue opening (2338) therein. Furthermore, because distal wall (2336) terminates below intermediate floor (2342), a vacuum opening (2347) is defined in the distal end of basket (2330) between intermediate floor (2342) and lower floor (2340). As will be described in greater detail below, tissue opening (2338) is generally configured to be selectively placed into communication with cutter via sample management assembly (2310). Similarly, vacuum opening (2347) is generally configured to be selectively placed into communication with and tube (2020) via sample management assembly (2310). The selective communication between tissue opening (2338) and vacuum opening (2347) generally permits tissue sample chamber (2346) to receive tissue samples therein when such tissue samples are acquired via needle (2110) and transported axially through the cutter.

Figure 13:
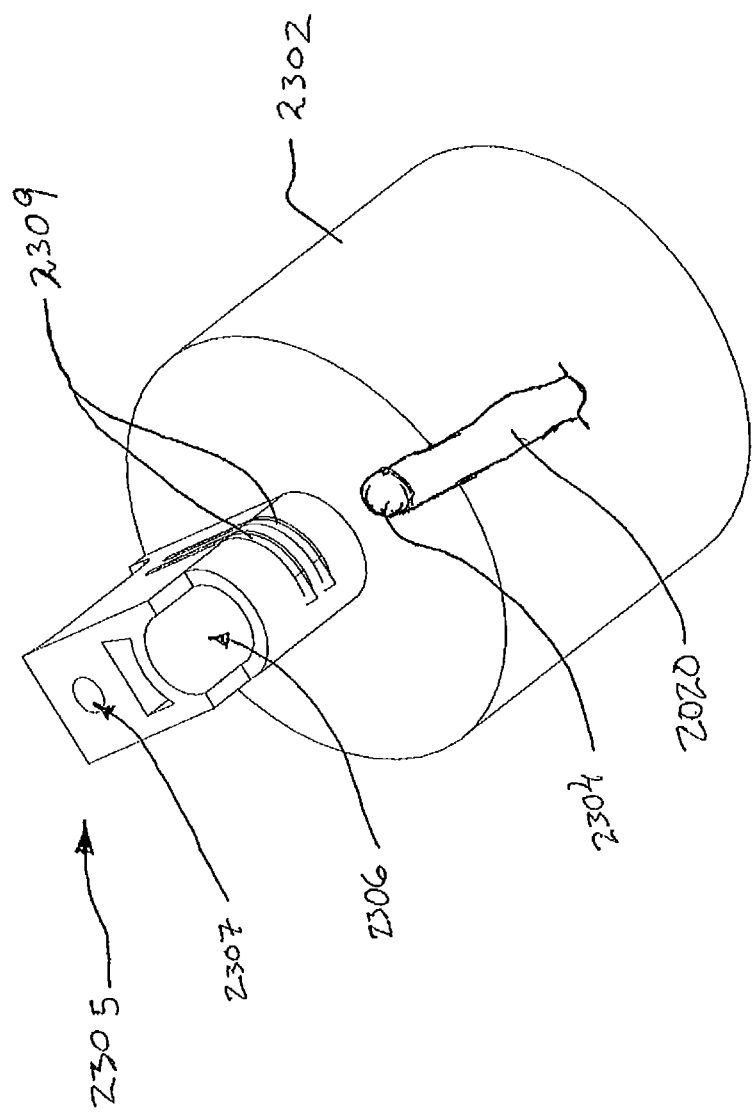
FIG. 13 depicts a perspective view of an outer cover of the tissue sample holder of FIG. 12.
Figure 14:
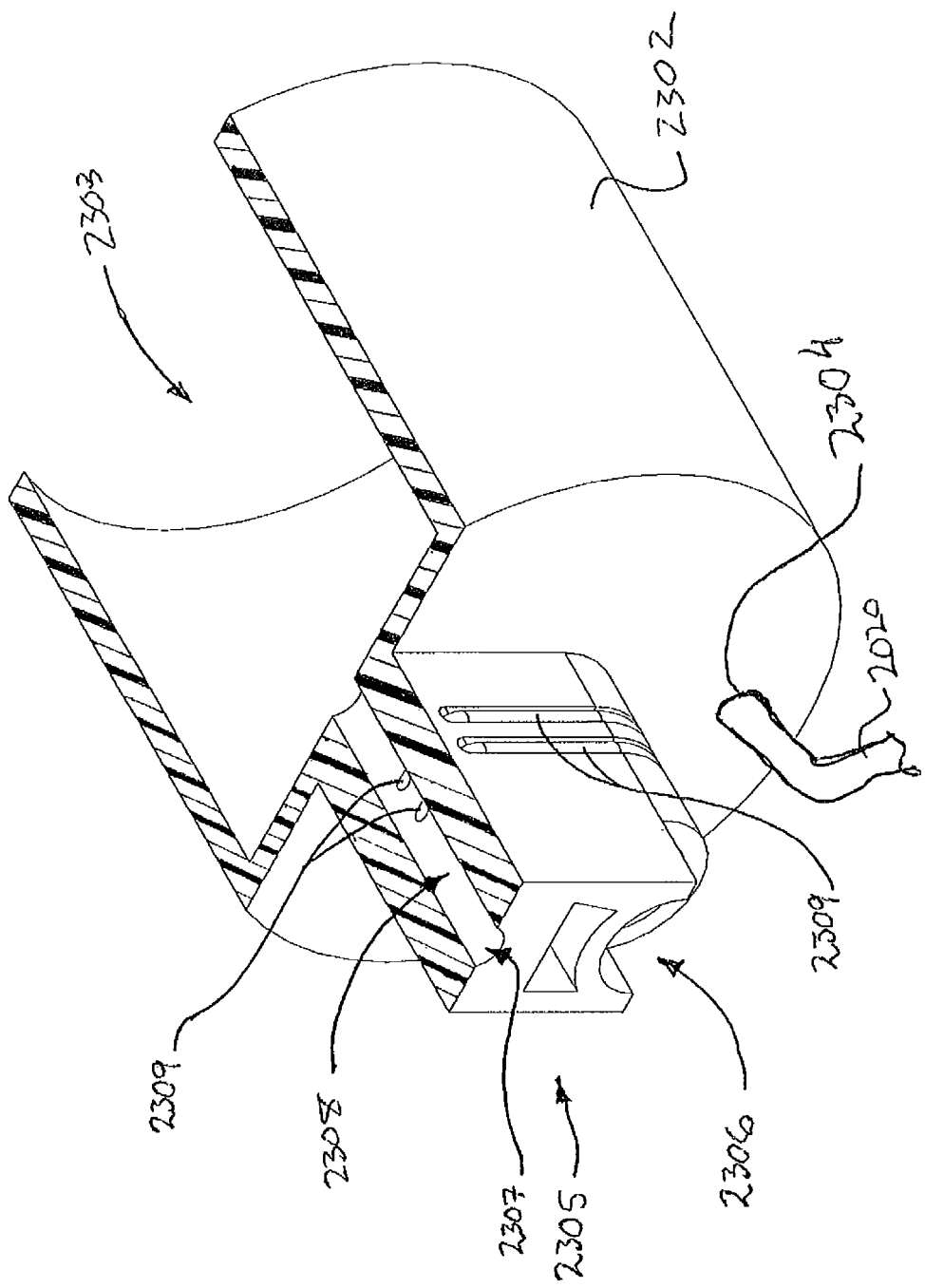
FIG. 14 depicts a perspective cross-sectional view of the outer cover of FIG. 13, the cross-section taken along line 26-26 of FIG. 13.

Outer cover (2302) is best seen in FIGS. 12-14. As can be seen, outer cover (2302) is generally cylindrically shaped and is configured to receive basket (2330) and sample management assembly (2310) through an open proximal end (2303). On the distal end of outer cover (2302), a vacuum port (2304) extends through outer cover (2302) to permit communication of vacuum into outer cover (2302) via tube (2020), as will be described in greater detail below.

A sample analysis assembly (2305) extends distally from outer cover (2302). Sample analysis assembly (2305) is generally configured to analyze individual tissue samples as they are collected by needle (2110) and the cutter disposed within needle (2110). Sample analysis assembly (2305) comprises a gear opening (2306), a cutter opening (2307) and two bioimpedance electrodes (2309). As will be described in greater detail below, gear opening (2306) extends through sample analysis assembly (2305) such that at least a portion of sample management assembly (2310) can extend out of outer cover (2302) and mechanically communicate with biopsy device.

Cutter opening (2307) is in communication with a cutter passage (2308), which extends through sample analysis assembly (2305). Cutter passage (2308) is similar to the cutter seals described above and/or in U.S. Pub. No. 2014/0039343 with respect to sealing members described above and in U.S. Pub. No. 2014/0039343. For instance, cutter passage (2308) is configured to receive the cutter disposed within needle (2110) through the entire range of motion of the cutter such that there is a sealed path between lateral aperture (2114) and the proximal end of the cutter. Additionally, in some instances, sample analysis assembly (2305) is constructed of a transparent material such that the interior of cutter passage (2308) is visible to an operator for visual analysis of individual tissue samples.

The interior of cutter passage (2308) is best seen in FIG. 14. As can be seen, electrodes (2309) extend from the exterior of sample analysis assembly (2305) though sample analysis assembly (2305) such that at least a portion of each electrode (2309) extends into the interior of cutter passage (2308). In the present aspect, each electrode (2309) is positioned inside cutter passage (2308) to make substantial physical contact with tissue samples as they pass through, or are present within, cutter passage (2308). As will be described in greater detail below, electrodes (2309) are generally configured to couple with a biopsy device as described in U.S. Pub. No. 2014/0039343 via any suitable electrical coupling such that the impedance of a given tissue sample may be measured. The measured impedance of a given tissue sample may then be analyzed via biopsy device and/or control module to identify various properties of the given tissue sample (e.g., to detect calcifications and/or other anomalies).

In the present aspect, electrodes (2309) extend from cutter passage (2308) along the outer surface of tissue analysis assembly (2305) and around the underside of gear opening (2306). Additionally, electrodes (2309) of the present aspect are partially inlaid into the outer surface of tissue analysis assembly (2305). In other aspects, electrodes (2309) may simply be secured to the outer surface of tissue analysis assembly (2305) without being inlaid into the surface at all. In still other aspects, electrodes (2309) may be entirely embedded in the structure of tissue analysis assembly (2305).

Electrodes (2309) of the present aspect are exposed to the exterior of tissue analysis assembly (2305) to promote electrical connectivity with the biopsy device. For instance, in some circumstances certain features of biopsy device include electrical contacts that correspond to electrodes (2309) such that electrical contacts of electrodes (2309) may communicate with biopsy device when probe (2100) is connected to biopsy device. To further promote electrical contact, it should be understood that in some aspects biopsy device or tissue analysis assembly (2305) may include various electrical connectivity features such as brushes, slip rings, and/or etc.

Regardless of particularly how electrodes (2309) achieve electrical continuity with biopsy device, it should be understood that ultimately impedance information from collected tissue samples is communicated from electrodes (2309) to the biopsy device and/or control module. This information can then be used to provide real time analysis of collected tissue samples. In merely one aspect, impedance information is used to detect the presence of cancerous cells in biopsy samples. Of course, any other suitable use of impedance information can be used as will be apparent to those of ordinary skill in the art in view of the teachings herein.

Figure 15:
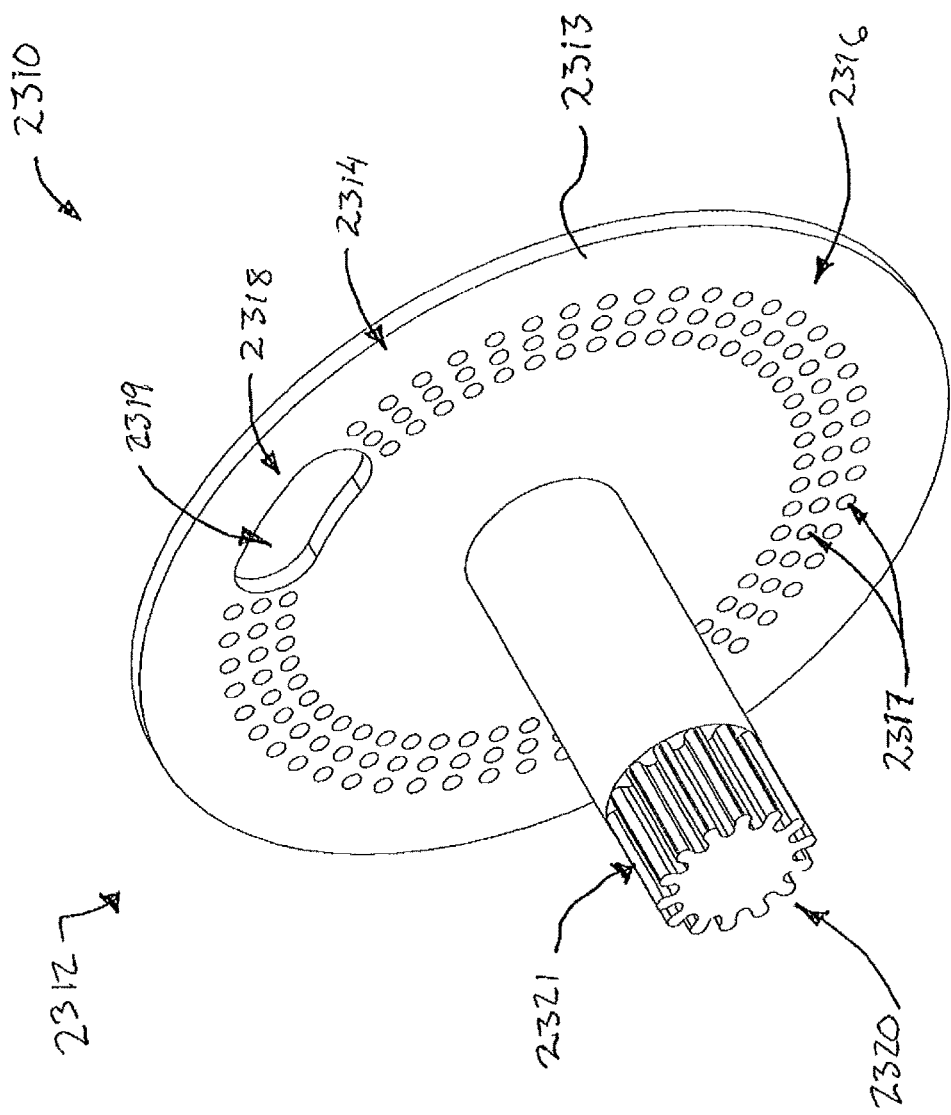
FIG. 15 depicts a perspective view of a sample management assembly for use with the tissue sample holder of FIG. 12.

Sample management assembly (2310) is shown in FIG. 15. As can be seen, sample management assembly (2310) comprises a rotatable member (2312). Rotatable member (2312) comprises a generally coin-shaped body (2313) with a rotation member (2320) extending distally from body (2313). Body (2313) defines a tissue manipulation ring (2314). Tissue manipulation ring (2314) includes a filter portion (2316) and a transport portion (2318). Filter portion (2316) comprises a plurality of vacuum holes (2317) arranged in a ring-shaped pattern axially around body (2313). Vacuum holes (2317) together are configured to receive vacuum and fluid therethrough, yet prevent the passage of tissue. By contrast, transport portion (2318) comprises a single opening (2319) that is sized to receive tissue samples therethrough. Transport portion (2318) is positioned along the same circular path as vacuum holes (2317) such that transport portion (2318) interrupts at least a portion of filter portion (2316).

Both filter portion (2316) and transport portion (2318) are positioned a distance from the center of body (2313) such that filter portion (2316) or transport portion (2318) can align with cutter passage (2308) of tissue analysis assembly (2305). However, whether filter portion (2316) or transport portion (2318) is indexed with cutter passage (2308) of tissue analysis assembly (2305) depends on the rotational orientation of rotatable member (2312). Thus, it should be understood that body (2313) is generally configured to selectively block or unblock transport of tissue samples to tissue sample chamber (2346) based on rotation of rotatable member (2312).

Additionally, it should be understood that vacuum port (2304) of outer cover (2302) is oriented an equal distance from the center of rotatable member (2312) as cutter passage (2308). Thus, vacuum port (2304) is continuously in communication with tissue sample holder (2300) via either filter portion (2316) or transport portion (2318).

As described above, rotation member (2320) extends distally from body (2313). Rotation member (2320) includes a toothed portion (2321) on the distal end thereof. When sample management assembly (2310) is disposed within outer cover (2302), rotation member (2320) extends through gear opening (2306) of tissue analysis assembly (2305) to permit mechanical communication between toothed portion (2321) and corresponding gears and/or other features of biopsy device. Thus, rotation member (2320) is configured to actuate sample management assembly (2310) via rotation of rotation member (2320).

Figure 16:
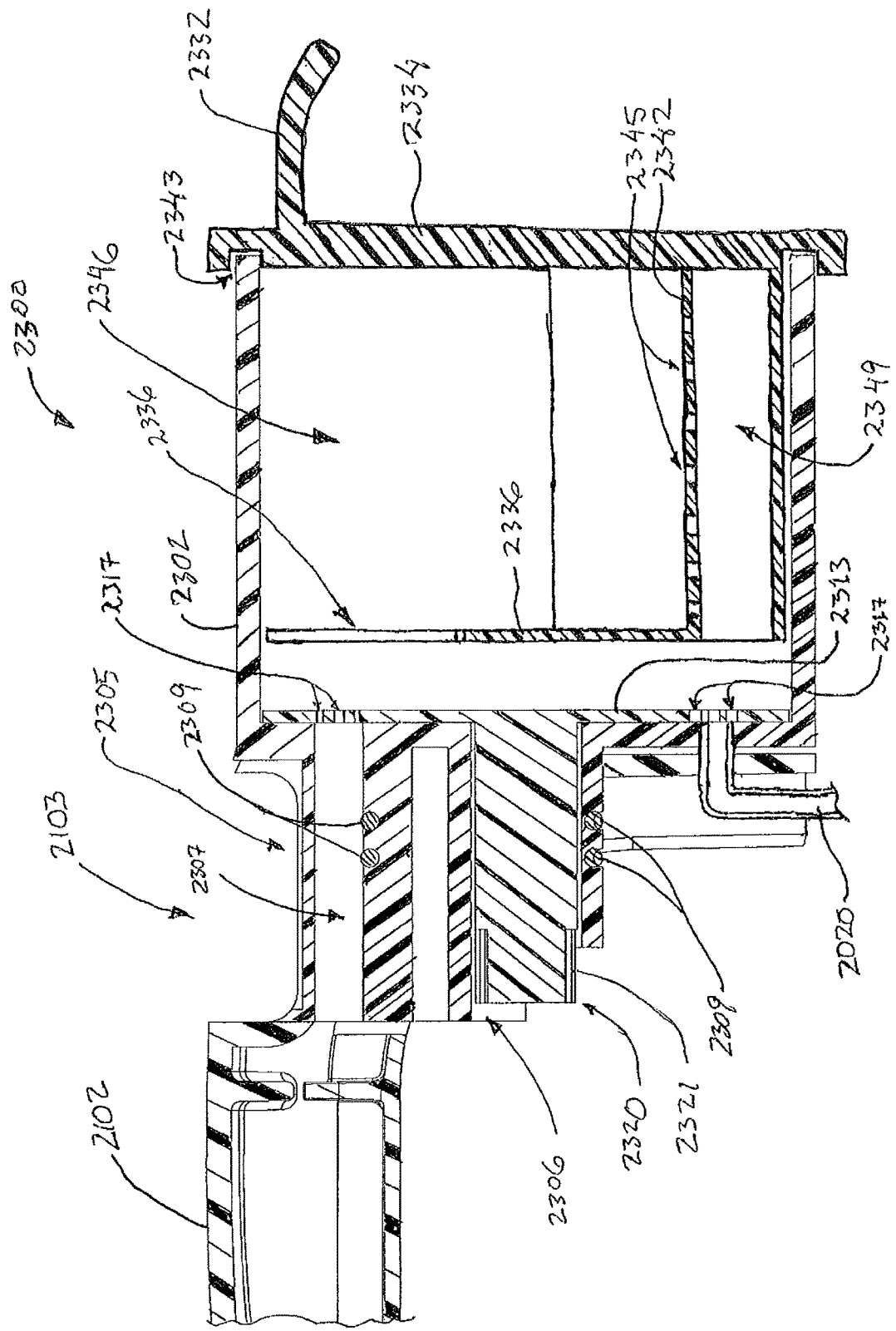
FIG. 16 depicts a side cross-sectional view of the probe of FIG. 11, with the cross-section taken along line 28-28 of FIG. 11 and the sample management assembly in a tissue blocking configuration.
Figure 17:
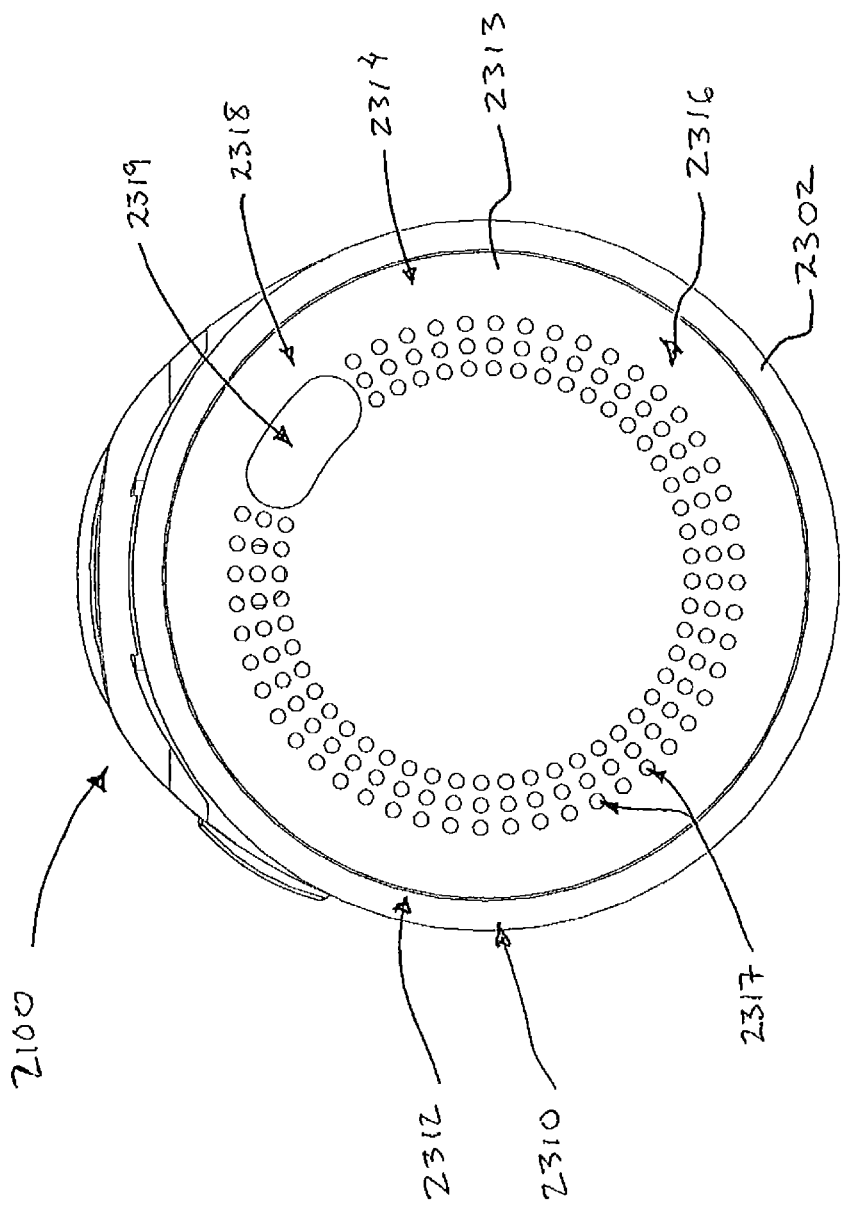
FIG. 17 depicts a front elevational view of the probe of FIG. 11 with the sample basket removed and the sample management assembly in a tissue blocking configuration.

FIGS. 16-19 show an exemplary operation of a sample management assembly to collect tissue samples in tissue sample holder (2300). In particular, as can be seen in FIGS. 16 and 17, sample management assembly (2310) initially begins in a sample blocking state. In the sample blocking state, sample management assembly (2310) is rotated to align filter portion (2316) of rotatable member (2312) with cutter passage (2308) of tissue analysis assembly (2305). Because filter portion (2316) comprises a plurality of vacuum openings (2317), tissue samples are generally blocked from entering tissue sample holder (2300) by filter portion (2316). However, due to the presence and location of vacuum port (2304) of outer cover (2302), vacuum continuously communicates from tube (2020) to tissue sample holder (2300) via vacuum port (2304). Thus, when sample management assembly (2310) is in the sample blocking state, vacuum can communicate to the cutter through vacuum port (2304) by way of vacuum passage (2349) in basket (2330), openings (2345) in intermediate floor (2342), and openings (2317) in filter portion (2316).

When the cutter is used to collect a tissue sample while sample management assembly (2310) is in the blocking state, the tissue sample is transported through cutter to cutter passage (2308) of tissue analysis assembly (2305) using vacuum from tube (2020) via vacuum port (2304). Filter portion (2316) blocks further movement of the tissue sample, thereby maintaining the tissue sample within cutter passage (2308) of tissue analysis assembly (2305). While the tissue sample is blocked from entering tissue sample chamber (2346) of tissue sample holder (2300), the tissue sample may be analyzed using electrodes (2309) that protrude into cutter passage (2308). In the present aspect, impedance related data is collected to detect the presence of cancer and/or other tissue anomalies. Sample management assembly (2310) may remain in the blocked state for the duration of the sample analysis procedure. In aspects where tissue analysis assembly (2305) comprises a transparent material, the tissue sample may additionally be visually analyzed during this time.

Figure 18:
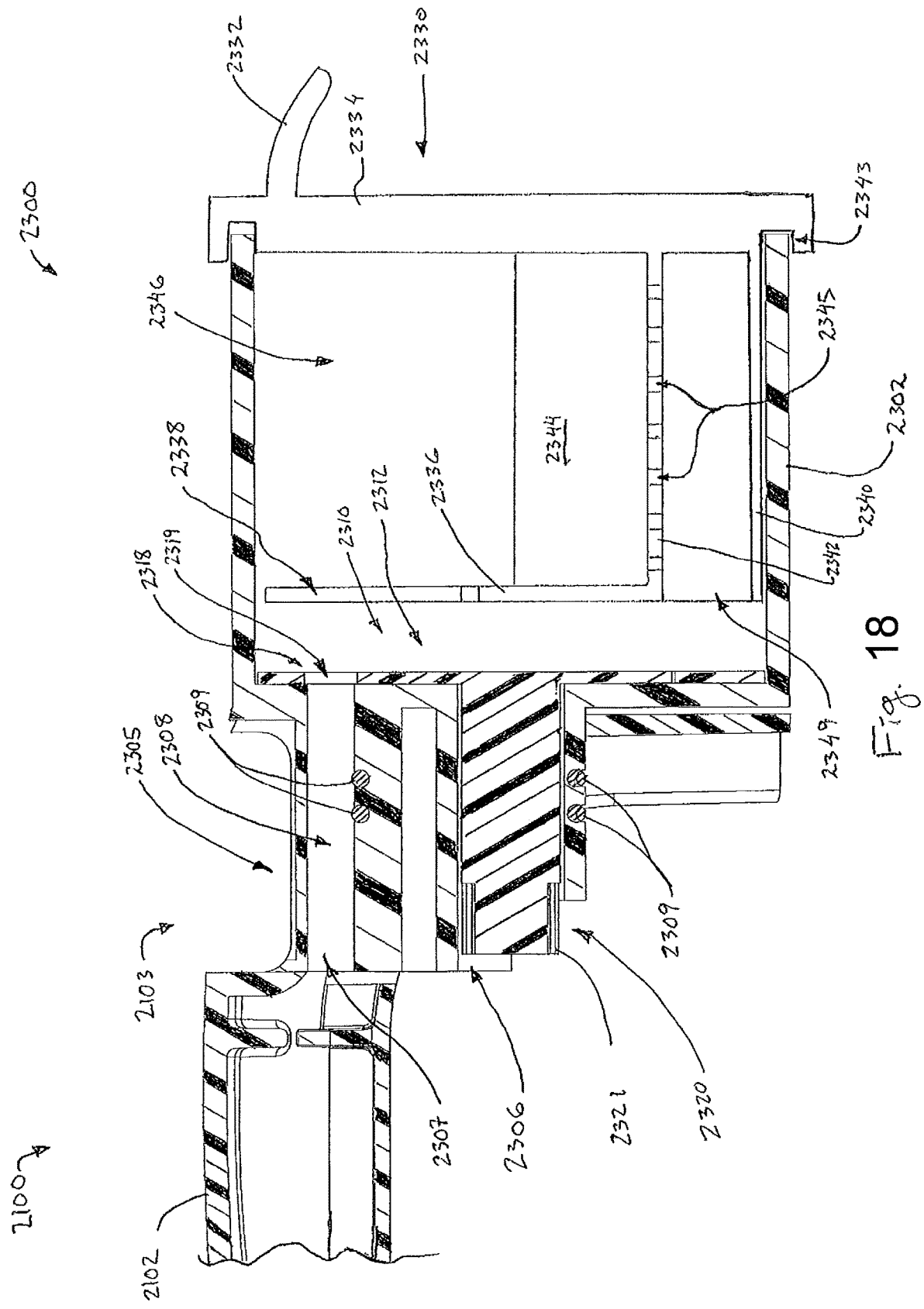
FIG. 18 depicts another side cross-sectional view of the probe of FIG. 11, with the sample management assembly in a tissue transport configuration.
Figure 19:
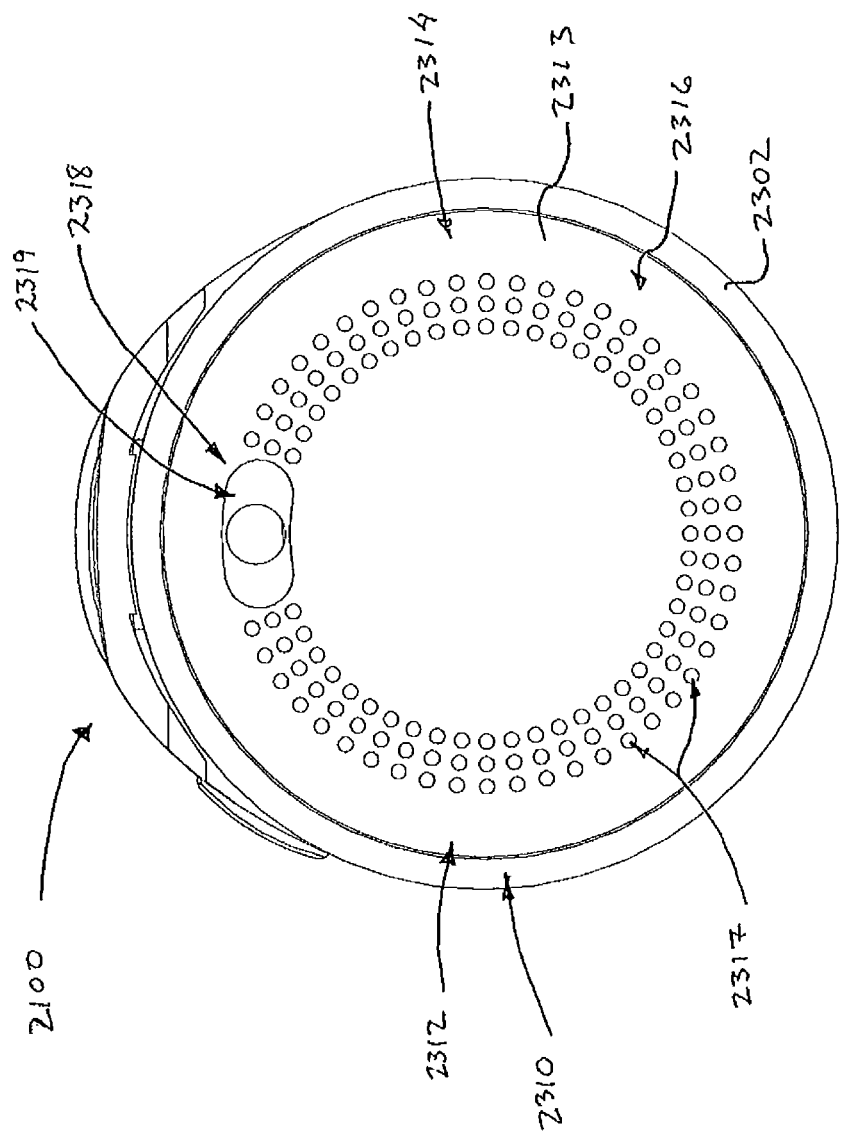
FIG. 19 depicts another front elevational view of the probe of FIG. 11 with the sample basket removed and the sample management assembly in a tissue transport configuration.

To communicate tissue samples to tissue sample holder (2300), sample management assembly (2310) is rotated to a tissue transport position as shown in FIGS. 18 and 19. To transition sample management assembly (2310) to the tissue transport position, rotatable member (2312) is indexed to align transport portion (2318) with cutter passage (2308). In particular, as can be seen in FIG. 19, rotatable member (2112) is rotated to align opening (2319) of transport portion (2318) with cutter passage (2308). With opening (2319) of transport portion (2318) aligned with cutter passage (2308), tissue samples may freely pass through sample management assembly (2310) where they are deposited in tissue sample chamber (2346) under the influence of vacuum communicated from tube (2020) via port (2304) in outer cover (2302)

Once a tissue sample has been collected in tissue sample holder (2300), sample management assembly (2310) may be rotated again to transition back to the tissue blocking position described above. It should be understood that sample management assembly (2310) may be rotated in any direction to transition between the tissue blocking position and the tissue transport position. Additionally, the procedure for collecting a sample, analyzing the sample, and then transporting to tissue sample holder (2300) may be repeated as desired by the operator until the conclusion of the biopsy procedure, or until tissue sample chamber (2346) is filled to capacity with tissue samples. Where tissue sample chamber (2346) is filled to capacity, basket (2330) may be removed from outer cover (2302) and either is emptied and reinserted, or replaced with an entirely new basket (2330). While tissue analysis assembly (2305) is described herein as being usable in connection with sample management assembly (2310), it should be understood that no such limitation is intended. For instance, in some aspects sample analysis assembly (2305) may be readily usable with sample management assembly (1310) described above or any other sample management assembly described herein. Of course, various other methods and/or procedures may be used as will be apparent to those of ordinary skill in the art in view of the teachings herein.

Figure 20:
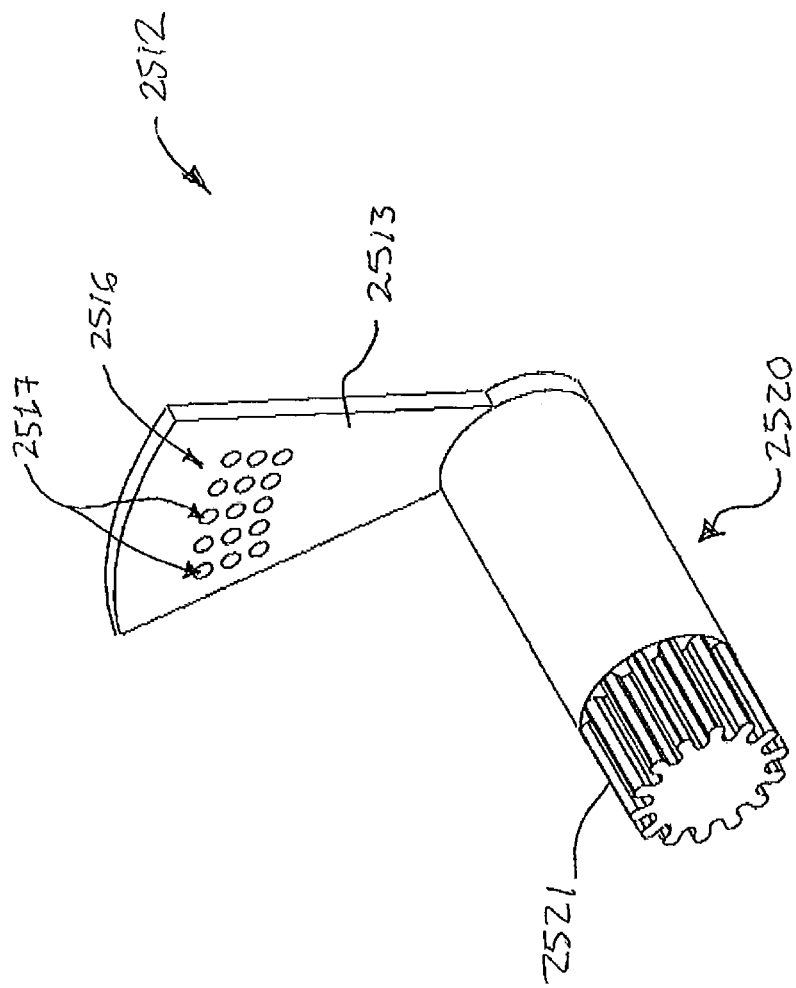
FIG. 20 depicts a perspective view of another aspect of an alternative sample management assembly for incorporation into the tissue sample holder of FIG. 12.

FIG. 20 depicts an alternative rotatable member (2512) that may be readily incorporated into sample management assembly (2310) described in above, or any other sample management assembly described herein. Rotatable member (2512) is substantially the same as rotatable member (2312) described above, except that a pivot screen body (2513) of rotatable member (2512) extends for only a portion of a circle instead of a complete circle. In particular, rotatable member (2512) of the present aspect comprises pivot screen body (2513) and a rotation member (2520) extending distally from pivot screen body (2513). Rotation member (2520) comprises a toothed portion (2521) and is substantially the same as rotation member (2320) described above such that rotation member (2520) will not be described in further detail herein.

Pivot screen body (2513) comprises a generally triangular cross-sectional shape extending radially outwardly from the axial center of rotation ember (2520). Pivot screen body (2513) comprises a filter band (2516) disposed near the outer edge of pivot screen body (2513). Filter band (2516) is substantially similar to filter portion (2316) described above with respect to rotatable member (2312), except filter band (2516) only extends for a fraction of an angular distance relative to filter portion (2316). As with filter portion (2316), filter band (2516) comprises a plurality of openings (2517) that are configured to permit the flow of vacuum and fluid, but prevent the flow of tissue samples. Accordingly, rotatable member (2512) is configured to substantially prevent flow of tissue samples to tissue sample holder (2300) when filter band (2516) is aligned with cutter passage (2308) of sample analysis assembly (2305).

In use, rotatable member (2512) functions as similarly described above with respect to rotatable member (2312). For instance, rotatable member (2512) is rotated via rotation member (2520) to align filter band (2516) with cutter passage (2307) of sample analysis assembly (2305) to place sample management assembly (2310) in a tissue blocking state. However, because rotatable member (2512) omits structures similar to transport portion (2318) of rotatable member (2312), rotatable member (2512) is only rotated out of alignment with cutter passage (2307) to permit transport of tissue samples to tissue sample holder (2300), and thereby transition sample management assembly (2310) to a transport state.

As noted above, in some instances it may be desirable to collect tissue samples in a single bulk chamber. However, when tissue samples are collected in bulk it may still be desirable to perform at least some tissue analysis as each tissue sample is collected. Thus, alternative configurations may be desirable to perform analysis of individual tissue samples in real time during a breast biopsy procedure.

In addition, in some instances tissue samples may exhibit the tendency to stick or adhere to various surfaces of tissue sample holders similar to the tissue sample holder described above and/or in U.S. Pub. No. 2014/0039343. Thus, in some aspects it may be desirable to include features for manipulation of tissue that overcome the tendency of tissue samples to stick and/or adhere to surfaces of the tissue sample holder. Various alternative sample management assemblies are described below. Such alternative sample management assemblies are constructed to include features for bulk storage of tissue samples and individual tissue sample analysis. Additionally, such alternative sample management assemblies are constructed to include features to manipulate tissue samples to overcome issues associated with the tissue properties described above and/or in U.S. Pub. No. 2014/0039343.

It should be understood that the various alternative tissue management assemblies described below may be readily incorporated into biopsy device and any one of the probes described above and/or in U.S. Pub. No. 2014/0039343. It should also be understood that the various components of the probes described above and/or in U.S. Pub. No. 2014/0039343 may be readily incorporated into the alternative sample management assemblies described below. Various suitable ways in which the above and below teachings may be combined will be apparent to those of ordinary skill in the art in view of the teachings herein. It should also be understood that the below teachings may be readily combined with the various teachings of the references that are cited herein.

Figure 21:
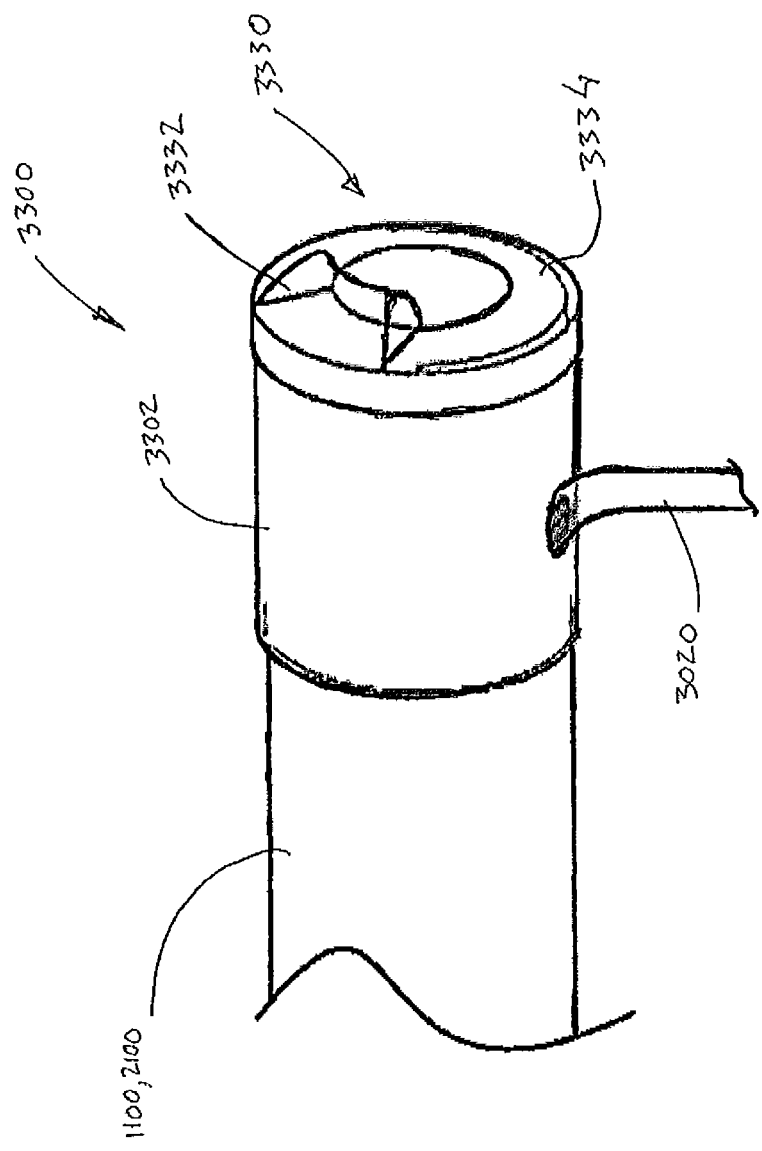
FIG. 21 depicts a perspective view of an alternative tissue sample holder for use with any one of the probes.
Figure 22:
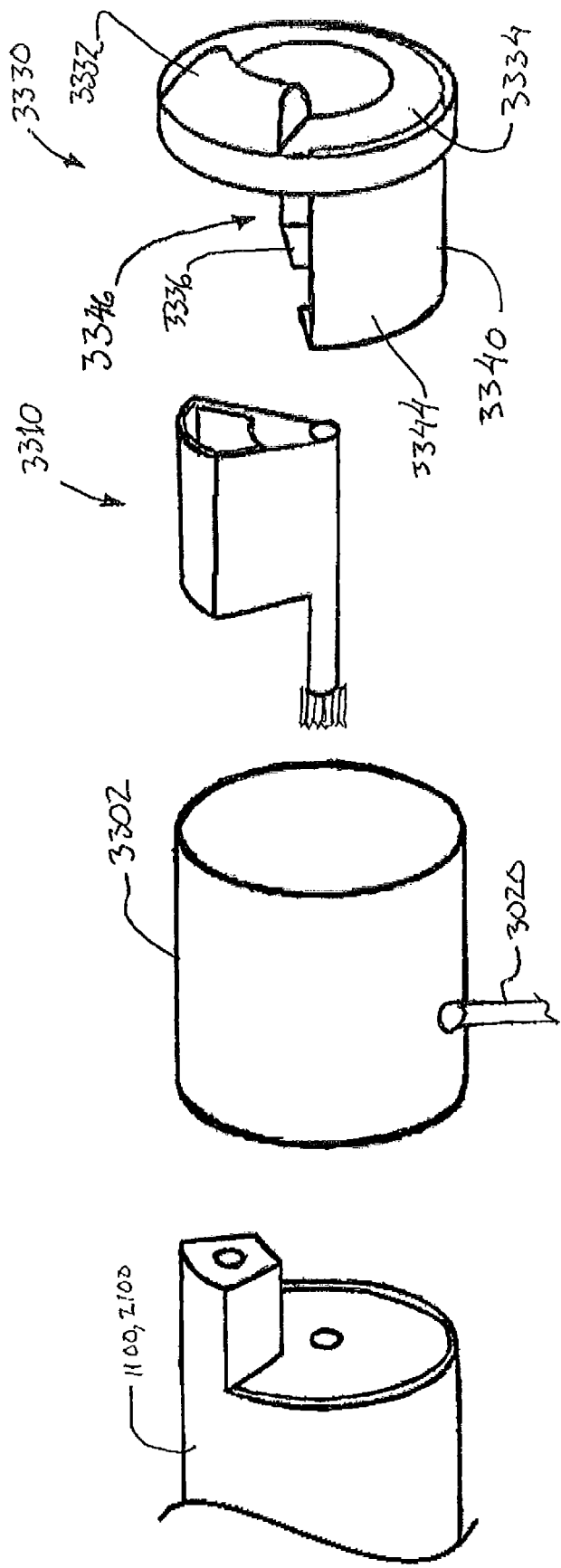
FIG. 22 depicts an exploded perspective view of the tissue sample holder of FIG. 21.

FIGS. 21-22 show an alternative sample management assembly (3310) that may be readily incorporated into any of the probes described above and/or in U.S. Pub. No. 2014/0039343. Sample management assembly (3310) is incorporated into a tissue sample holder (3300) that is substantially similar to tissue sample holders described above and/or in U.S. Pub. No. 2014/0039343. It should be understood that unless otherwise specifically noted herein, tissue sample holder (3300) is identical to tissue sample holders described above and/or in U.S. Pub. No. 2014/0039343. For instance, tissue sample holder (3300) of the present aspect is configured to store tissue samples in a single bulk tissue sample chamber (3346). As is best seen in FIG. 22, tissue sample holder (3300) comprises a sample basket (3330), a sample management assembly (3310), and an outer cover (3302).

Sample basket (3330) is substantially similar to sample baskets (1330, 2330) described above and/or in U.S. Pub. No. 2014/0039343. For instance, basket (3330) is generally configured to hold a plurality of tissue samples in a single tissue sample chamber (3346). As can be seen, basket (3330) comprises a grip (3332) and a proximal wall (3334). Grip (3332) extends proximally from proximal wall (3334) and is configured to be grasped by an operator to manipulate basket (3330). As will be described in greater detail below, grip (3332) of the present aspect is additionally configured to provide a fluid channeling function. Proximal wall (3334) defines a channel (not shown) along the outer edge of the distal side of proximal wall (3334). The channel is configured to receive at least a portion of outer cover (3302) to fluidly seal the proximal end of tissue sample holder (3300) when basket (3330) is disposed in outer cover (3302). Although not shown, it should be understood that the channel can be equipped with gaskets or other sealing elements to further promote sealing between basket (3330) and outer cover (3302).

A pair of sidewalls (3344) and a lower floor (3340) extend distally from proximal wall (3334). In the present aspect, sidewalls (3344) and lower floor (3340) are defined by a single semi-circular shaped member. However, it should be understood that in other aspects sidewalls (3334) and lower floor (3340) are more discretely defined by a square or rectangular cross-section. Although not shown, it should be understood that basket (3330) of the present aspect includes an intermediate floor (not shown) disposed above lower floor (3340) as similarly described above with respect to baskets (1330, 2330).

A distal wall (3336) is disposed at the distal end of basket (3330). Distal wall (3336) of the present aspect defines a semi-circular shape that is configured to receive at least a portion of sample management assembly (3310), as will be described in greater detail below. Distal wall (3336), proximal wall (3334), sidewalls (3344), and the intermediate floor together define a tissue sample chamber (3346). Tissue sample chamber (3346) is generally configured to receive a plurality of tissue samples therein. In the present aspect, tissue sample chamber (3346) is configured to receive anywhere between about 20 to about 50 tissue samples. Of course, in other aspects tissue sample chamber (3346) may be configured to receive any other suitable number of tissue samples.

Outer cover (3302) of the present aspect is substantially similar to outer covers (1302, 2302) described above. For instance, outer cover (3302) of the present aspect comprises a generally hollow cylindrical shape that is configured to receive basket (3330) and sample management assembly (3310). However, unlike outer covers (1302, 2302) described above, outer cover (3302) of the present aspect is connected directly to tube (3020) to supply vacuum directly to outer cover (3302). Although outer cover (3302) of the present aspect is shown as connecting directly to tube (3020), it should be understood that no such limitation is intended. For instance, in some aspects tube (3020) is connected to outer cover (3302) and the rest of tissue sample holder (3300) as similarly described above with respect to tissue sample holders (1300, 2300).

Figure 23:
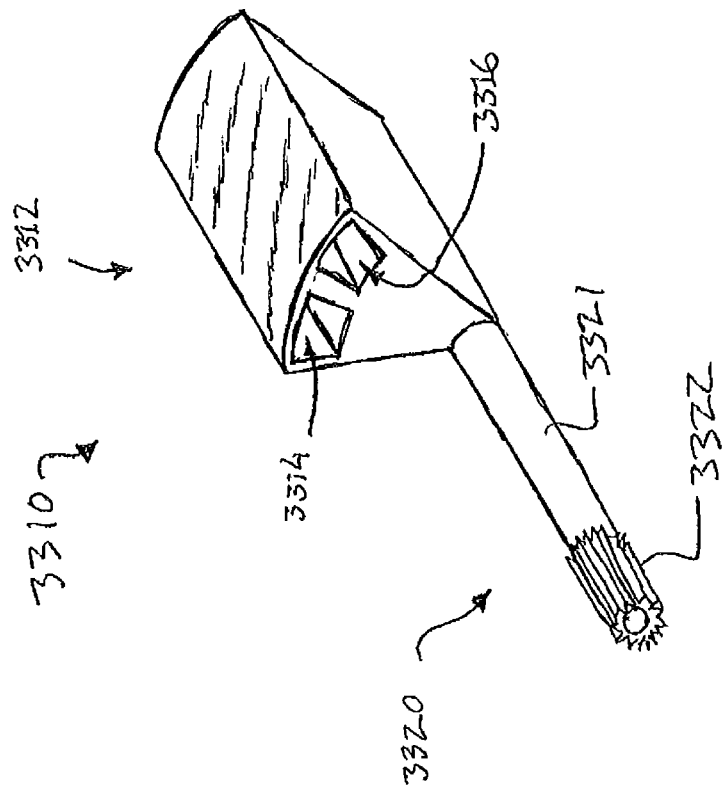
FIG. 23 depicts a perspective view of a sample management assembly for use with the tissue sample holder of FIG. 21.

Sample management assembly (3310) is best seen in FIG. 23. As can be seen, sample management assembly (3310) generally comprises a sample receiving portion (3312) and a drive portion (3320) extending proximally from sample receiving portion (3312). Sample receiving portion (3312) has a shape that is generally characterized by a triangular prism with a rounded top to that corresponds to the cylindrical shape of outer cover (3302). Sample receiving portion (3312) of the present aspect comprises a substantially transparent material. The transparency of sample receiving portion (3312) is generally sufficient to permit visual analysis of tissue samples received therein.

Sample receiving portion (3312) includes two sample chambers (3314, 3316) positioned adjacent to each other. Each sample chamber (3314, 3316) extends longitudinally through sample receiving portion (3312) from end to end such that each sample chamber (3314, 3316) is open on the proximal and distal ends of sample receiving portion (3312). The longitudinal extension of each sample chamber (3314, 3316) is generally along an axis that is parallel to a longitudinal axis of the cutter of any one or more of probes described above and/or in U.S. Pub. No. 2014/0039343. Additionally, the longitudinal extension of each sample chamber (3314, 3316) is generally parallel but offset relative to a rotation axis defined by drive portion (3320).

Each sample chamber (3314, 3316) is generally configured to receive a single tissue sample therein. As will be described in greater detail below, each sample chamber (3314, 3316) is generally positioned to selectively align with the cutter of one or more of probes described above and/or in U.S. Pub. No. 2014/0039343 when sample receiving portion (3312) is rotated via drive portion (3320). When a selected chamber (3314, 3316) is aligned with the cutter of any one or more of previously described probes, the non-aligned chamber (3316, 3314) acts as a vacuum passage such that fluid first passes through the cutter and into the selected chamber (3314, 3316) before passing into the non-aligned chamber (3316, 3314). As will also be described in greater detail below, passage of fluid in this manner is facilitated by fluid channeling features of grip (3332) of sample basket (3330).

Figure 24:
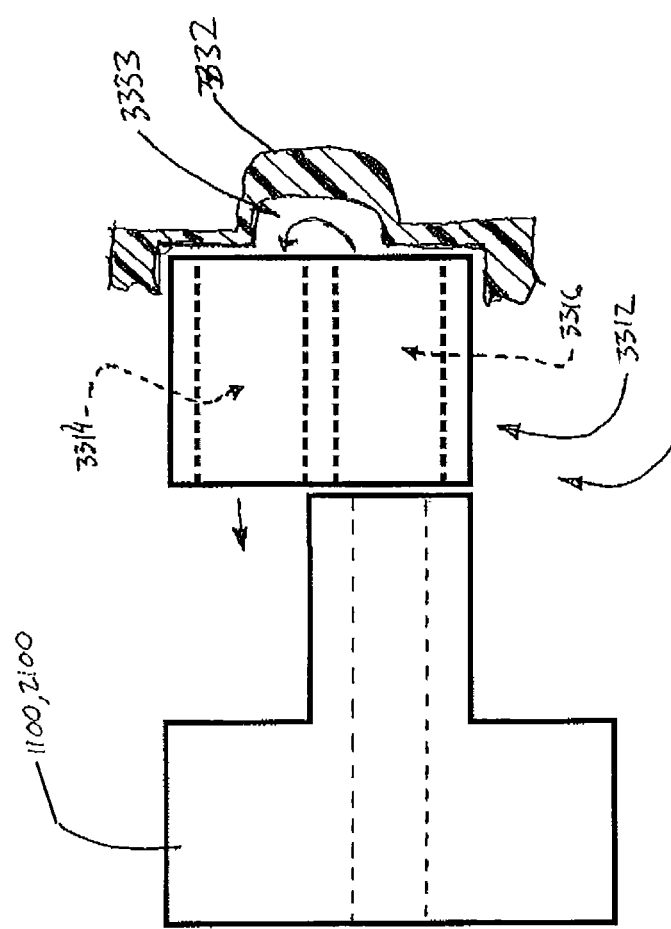
FIG. 24 depicts an partial cut-away side view of the tissue sample holder of FIG. 21, with the sample management assembly in a first sample receiving configuration.

It should be understood that any one of probes used in the present aspect and/or in U.S. Pub. No. 2014/0039343 are capable of being modified for use with sample management assembly (3310). For instance, as can be seen in FIG. 24, sample receiving portion (3312) is generally disposed proximally from the proximal end of any one of probes. To accommodate this positioning while maintaining communication with the cutter of a given probe, the particular probe used includes an extension member, tube, cannula, or device extending proximally from the proximal end of the probe. As will be described in greater detail below, this configuration permits sample receiving portion (3312) to eject a tissue sample distally out of a given sample chamber (3314, 3316).

Drive portion (3320) generally comprises a cylindrical shaft (3321) and a gear portion (3322). Shaft (3321) extends distally from sample receiving portion (3312) and is of integral construction therewith. Gear portion (3322) is disposed on the distal end of shaft (3321). Gear portion (3322) is generally configured to interact with corresponding components of biopsy device to permit selective rotation of sample management assembly (3310) about a rotation axis defied by the distal extension of cylindrical shaft (3321). As will be described in greater detail below, this selective rotation of sample management assembly (3310) permits each chamber (3314, 3316) of sample receiving portion (3312) to be indexed into communication of the cutter of any one or more of probes described above and/or in U.S. Pub. No. 2014/0039343.

Figure 25:
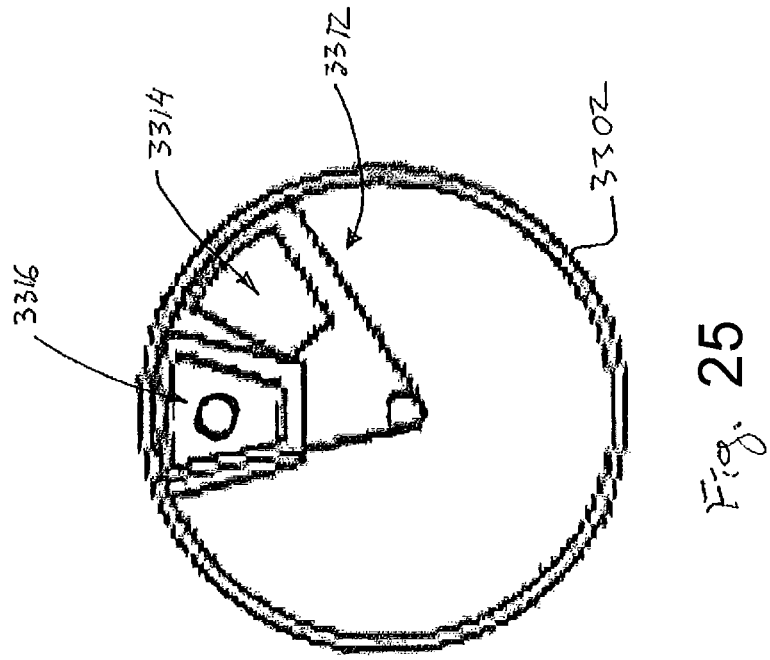
FIG. 25 depicts a front elevational view of the tissue sample holder of FIG. 21, with a sample basket removed and the sample management assembly in the second sample receiving configuration.

FIGS. 24-27 show an exemplary operation of sample management assembly (3310) to deposit a plurality of tissue samples into sample basket (3330). In particular, as can be seen in FIGS. 24 and 25, sample management assembly (3310) is initially rotated into position relative to any one or more of probes to align sample chamber (3316) with the cutter. As described above and/or in U.S. Pub. No. 2014/0039343, rotation of sample management assembly (3310) is achieved via drive portion (3320), which is actuated by certain drive components of biopsy device.

One sample chamber (3316) is aligned as shown in FIG. 24, sample management assembly (3310) is configured to receive a first tissue sample. In particular, to receive the first tissue sample, the first tissue sample is severed using the cutter of any one or more of probes as described above and/or in U.S. Pub. No. 2014/0039343. Vacuum is applied to tube (3020) to initiate transport of the first tissue sample through the cutter and into sample chamber (3316). During this process, vacuum passes through tube (3020) and into sample basket (3330). Once in sample basket (3330), vacuum passes into chamber (3314). Vacuum is then communicated from chamber (3314) to chamber (3316) via a fluid passage (3333) defined by grip (3332) of sample basket (3330). Finally, vacuum passes through sample chamber (3316) to the cutter. Thus, it should be understood that sample chambers (3314, 3316) and fluid passage (3333) collectively define a fluid passage from tube (3020) to the cutter as illustrated with arrows in FIG. 24.

Once the first tissue sample is received in sample chamber (3316), the operator can analyze the first tissue sample by visually inspecting the sample through the transparency of sample receiving portion (3312) and the transparency of outer cup (3302). Additionally, it should be understood that in some aspects sample chambers (3314, 3316) are equipped with sensors such as bioimpedance sensors similar to those described above with respect to probe (2100). In still other aspects, sample chambers (3314, 3316) are equipped with any other suitable sample analysis feature as will be apparent to those of ordinary skill in the art in view of the teachings herein.

Once an operator has sufficiently analyzed the first tissue sample received in sample chamber (3316), sample management assembly (3310) may be next reconfigured to receive a second tissue sample. As is best seen in FIGS. 26 and 27, sample management assembly (3310) is reconfigured to receive the second tissue sample by rotating sample management assembly (3310) via drive portion (3320). This rotation aligns sample chamber (3314) with the cutter of any one or more of the probes described above. Thus, sample receiving portion (3312) is positioned such that the second tissue sample may be received in sample chamber (3314).

To receive the second tissue sample, vacuum is again applied to tube (3020) to transport the second tissue sample through the cutter and into sample chamber (3314). This involves a pneumatic circuit that is substantially similar to the pneumatic circuit described above with respect to FIG. 24. However, unlike the pneumatic circuit described above, in the present configuration, vacuum travels along an opposite path. In particular, once vacuum is applied to sample basket (3330), vacuum passes into chamber (3316). Vacuum is then communicated from chamber (3316) to chamber (3314) via fluid passage (3333) defined by grip (3332) of sample basket (3330). Finally, vacuum passes through sample chamber (3314) to the cutter. Because sample chamber (3316) is already occupied by a tissue sample, it should be understood that the present pneumatic circuit has a dual purpose of both receiving the second tissue sample in sample chamber (3314) and ejecting the first tissue sample from sample chamber (3314) (as illustrated by arrow B in FIG. 26). Thus, when sample chamber (3314) receives the second tissue sample, the first tissue sample is substantially simultaneously ejected from sample chamber (3316). It should be understood that when the first tissue sample is ejected from sample chamber (3316), the first tissue sample is deposited in sample basket (3330) for storage until competition of the biopsy procedure or until sample basket (3330) is emptied.

One the second tissue sample is received in sample chamber (3314), the second tissue sample may be analyzed as similarly discussed above with respect to the first tissue sample. At the conclusion of tissue analysis, a subsequent tissue sample may be collected by returning sample management assembly (3310) to the configuration shown in FIGS. 24 and 25. Further tissue samples may then be acquired and analyzed by repeating the procedure described above. Thus, a plurality of tissue samples are acquired and analyzed by alternating sample management assembly (3310) between the configurations shown in FIGS. 24 and 25, and FIGS. 26 and 27. This process may be used by an operator until a desired number of tissue samples are acquired and analyzed.

In some instances challenges with manipulating tissue sample may be encountered. For aspect, generally moist tissue samples may sometimes exhibit an attraction to relatively dry surfaces within components of biopsy device or other components described herein. In other words, tissue samples may sometimes be sticky or tacky. Accordingly, in some devices it may be desirable to include mechanisms that are suitable for manipulating tissue while overcoming the attraction that is sometimes encountered with tissue samples.

Figure 29:
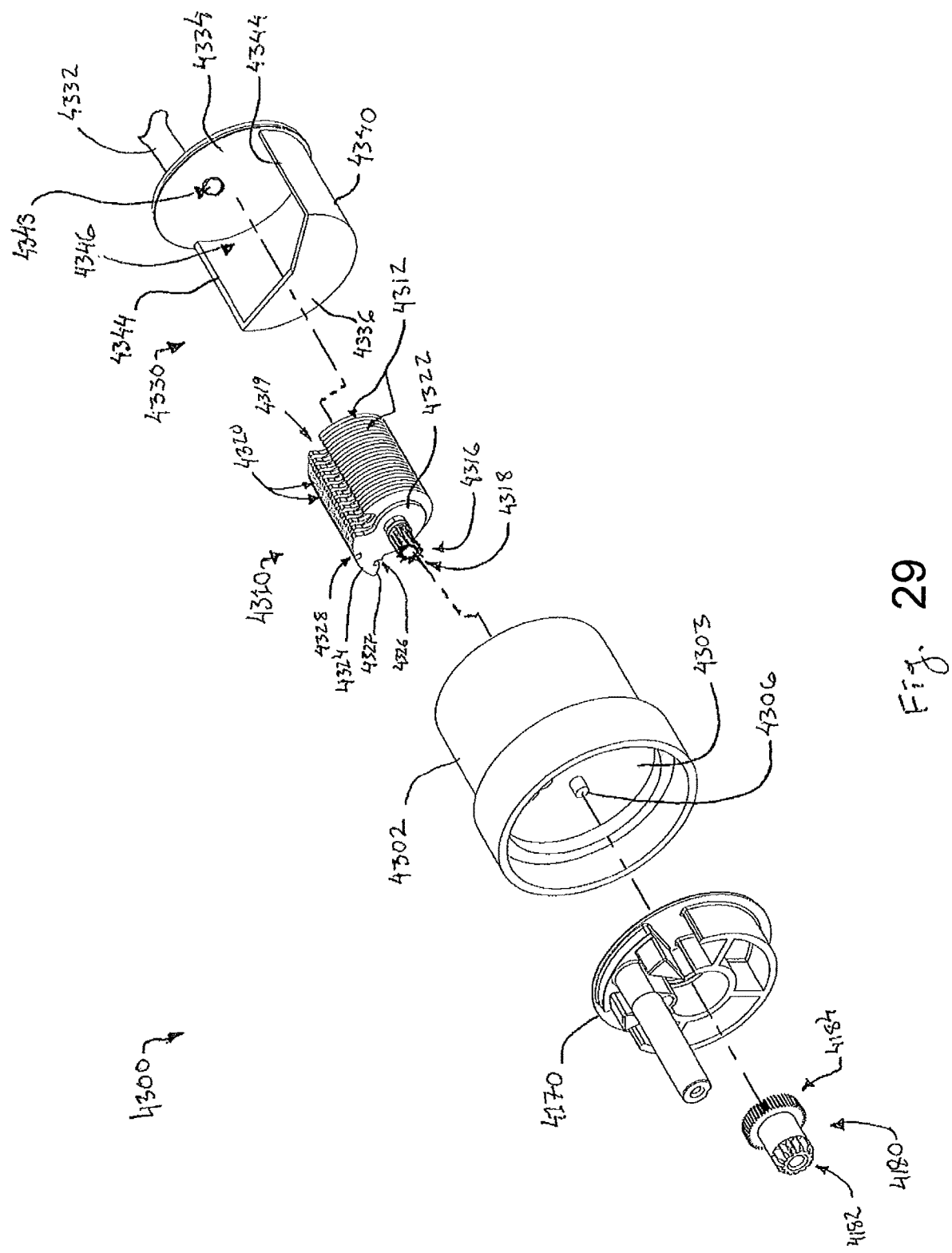
FIG. 29 depicts a perspective exploded view of the tissue sample holder of FIG. 28.
Figure 30:
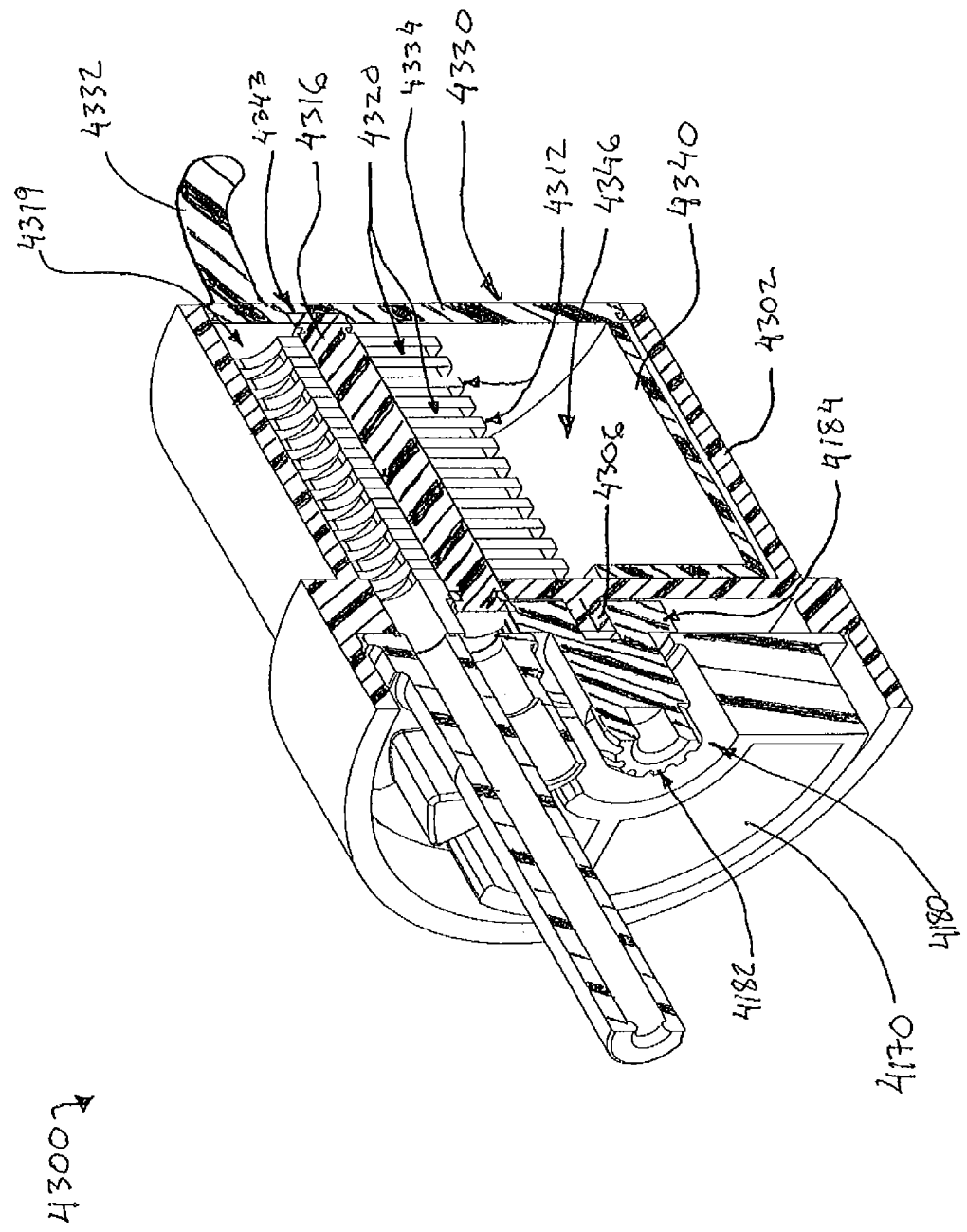
FIG. 30 depicts a perspective cross-sectional view of the tissue sample holder of FIG. 28, with the cross-section taken along line 42-42 of FIG. 28.
Figure 31:
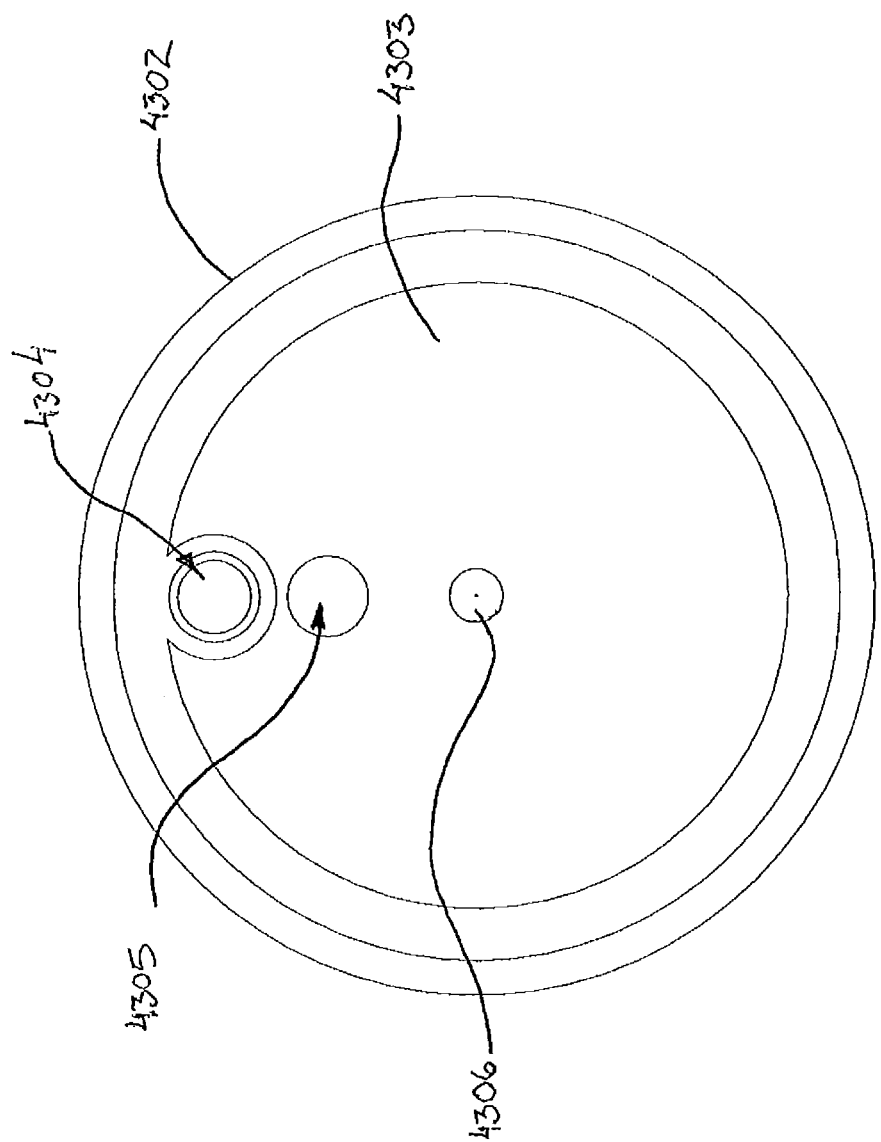
FIG. 31 depicts a front elevational view of an outer cover of the tissue sample holder of FIG. 28.

FIGS. 16-18 show an exemplary alternative tissue sample holder (4300) that may be readily incorporated into any of the probes described above. Tissue sample holder (4300) includes a sample management assembly (4310) that is generally configured to provide individual tissue sample analysis while overcoming certain difficulties associated with manipulating tissue samples that have the tendency to stick to surfaces within tissue sample holder (4300). It should be understood that unless otherwise specifically noted herein, tissue sample holder (4300) is identical to tissue sample holders (1300, 2300, 3300) described above. For instance, tissue sample holder (4300) of the present aspect is configured to store tissue samples in a single bulk sample chamber (4346). As is best seen in FIG. 29, tissue sample holder (4300) comprises a rotation member (4180), a sealing member (4170), a sample basket (4330), a sample management assembly (4310), and an outer cover (4302). Rotation member (4180) is substantially the same as rotation member described in U.S. Pub. No. 2014/0039343 except rotation member (4180) of the present aspect includes a second gear (4184) in the place of grasping feature (184) described in U.S. Pub. No. 2014/0039343. As will be described in greater detail below, second gear (4184) is generally configured to drive various components of sample management assembly (4310) when a first gear (4182) of rotation member (4170) is acted upon by biopsy device. Sealing member (4170) of the present aspect is substantially the same as sealing members described in U.S. Pub. No. 2014/0039343, such that further details of sealing member (4170) will not be described herein.

Sample basket (4330) is substantially similar to sample baskets (1330, 2330, 3330) described above. For instance, basket (4330) is generally configured to hold a plurality of tissue samples in a single sample chamber (4346). As can be seen, basket (4330) comprises a grip (4332) and a proximal wall (4334). Grip (4332) extends proximally from proximal wall (4334) and is configured to be grasped by an operator to manipulate basket (4330). Proximal wall (4334) is configured to seal with the inner diameter of outer cover (4302) along the outer edge of proximal wall (4334). Thus, it should be understood that in some aspects the outer edge of proximal wall (4334) may include certain sealing features such as gaskets, sealing members, channels, and/or etc. Proximal wall (4334) further includes a shaft opening (4343) extending through at least a portion of proximal wall (4334). Shaft opening (4343) of the present aspect comprises a counterbore extending through only a portion of proximal wall (4334). It should be understood that in other aspects, shaft opening (4343) alternatively extends through the entire thickness of proximal wall (4334). As will be described in greater detail below, shaft opening (4343) is generally positioned and configured to support various components of sample management assembly (4310).

A pair of sidewalls (4344) and a lower floor (4340) extend distally from proximal wall (4334). In the present aspect, sidewalls (4344) and lower floor (4340) are defined by a single semi-circular shaped member. However, it should be understood that in other aspects sidewalls (4334) and lower floor (4340) are more discretely defined by a square or rectangular cross-section. Although not shown, it should be understood that in some aspects basket (4330) additionally includes an intermediate floor (not shown) or other vacuum control features disposed above lower floor (4340) as similarly described above and/or in U.S. Pub. No. 2014/0039343 with respect to baskets (1330, 2330). Where such an intermediate floor is incorporated into basket (4330), it should be understood that such aspects may include vent openings or other features to direct the flow of fluid through basket (4330).

A distal wall (4336) is disposed at the distal end of basket (4330). Distal wall (3336) of the present aspect defines a semi-circular shape that is configured to receive at least a portion of sample management assembly (4310), as will be described in greater detail below. Distal wall (4336), proximal wall (4334), sidewalls (4344), and the intermediate floor together define a tissue sample chamber (4346). Tissue sample chamber (4346) is generally configured to receive a plurality of tissue samples therein.

In one aspect, tissue sample chamber (4346) is configured to receive anywhere from about 1 to about 50 tissue samples. In another aspect, tissue sample chamber (4346) is configured to receive anywhere from about 10 to about 50 tissue samples. In one aspect, tissue sample chamber (4346) is configured to receive anywhere from about 20 to about 50 tissue samples. In one aspect, tissue sample chamber (4346) is configured to receive anywhere from about 25 to about 50 tissue samples.

Outer cover (4302) of the present aspect is substantially similar to the outer covers described above. For instance, outer cover (4302) of the present aspect comprises a generally hollow cylindrical shape that is configured to receive basket (4330) and sample management assembly (4310). However, unlike outer covers (1302, 2302, 3302) described above, outer cover (4302) of the present aspect includes certain features that are configured to engage or support the operation of sample management assembly (4310). For instance, as can best be seen in FIGS. 32 and 33, outer cover (4302) includes a distal wall (4303) that is disposed proximally of the distal end of outer cover (4302). Distal wall (4303) includes a cutter bore (4304), a shaft opening (4305), and a shaft pin (4306). Cutter bore (4304) is configured to communicate with the cutter of any one of probes described above and/or in U.S. Pub. No. 2014/0039343 via sealing member (4170). Thus, cutter bore (4304) provides an opening that permits tissue samples to pass through distal wall (4303) for manipulation via sample management assembly (4310). Although not shown, it should be understood that in some aspects cutter bore (4304) includes features that are configured to promote sealing between cutter bore (4304) and sealing member (4170).

Shaft opening (4305) extends entirely through distal wall (4303). Shaft opening (4305) is generally comprises a circular shape that is configured to provide an opening for at least a portion of certain drive components of sample management assembly (4310) to pass through distal wall (4303). As will be described in greater detail below, this feature of distal wall (4303) permits rotational force to be communicated through distal wall (4303) to drive various components of sample management assembly (4310).

Shaft pin (4306) generally comprises a cylindrical protrusion extending distally from distal wall (4303). Like with shaft opening (4305) described above, shaft pin (4306) is generally associated with certain drive components of sample management assembly (4310). As will be described in greater detail below, shaft pin (4306) provides a mechanical ground for certain drive components of sample management assembly (4310) to rotatably attach to. Shaft opening (4305) and shaft pin (4306) are generally spaced from each other to support such an arrangement.

Figure 32:
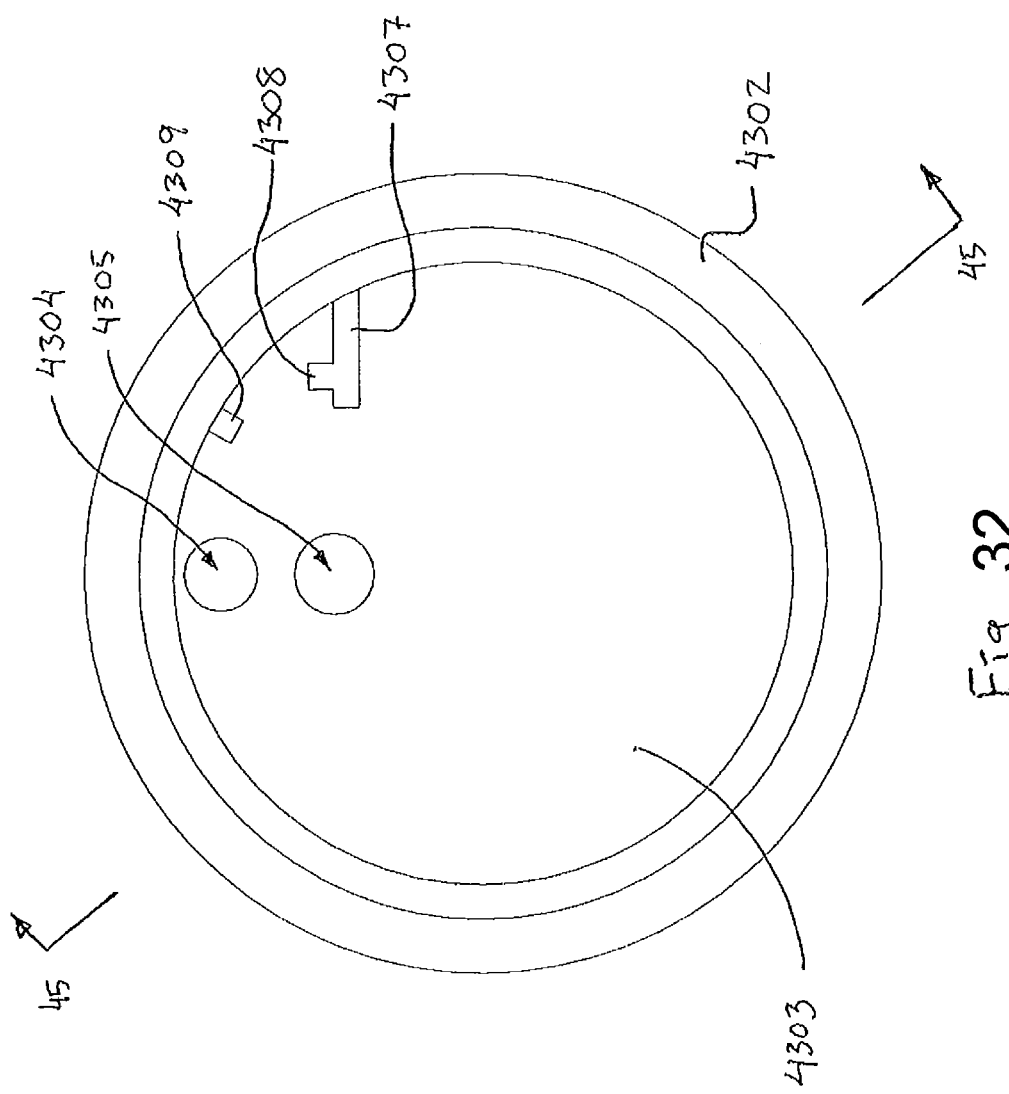
FIG. 32 depicts a rear elevational view of the outer cover of FIG. 31.
Figure 33:
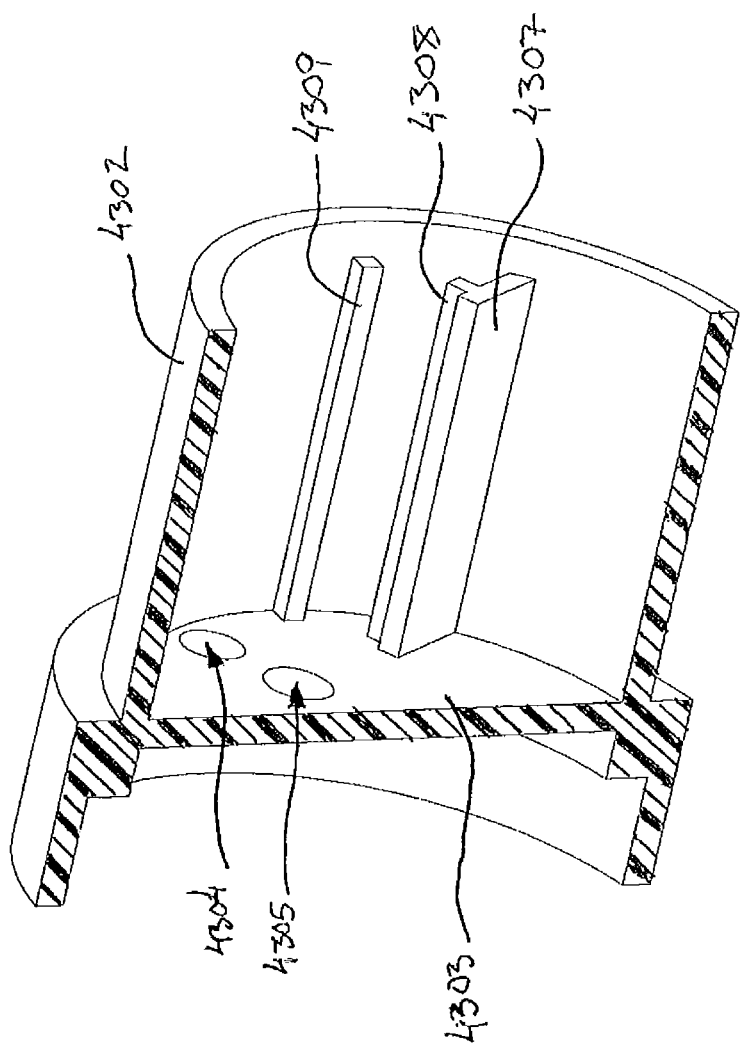
FIG. 33 depicts a perspective cross-sectional view of the outer cover of FIG. 31, the cross-section taken along line 45-45 of FIG. 32.

FIGS. 32 and 33 show the interior of outer cover (4302). As can be seen, the interior of outer cover (4302) includes a first rotation lock (4307) and a second rotation lock (4309). Each rotation lock (4307, 4309) is generally configured to engage a portion of sample management assembly (4310). As will be described in greater detail below, such engagement prevents rotation of certain components of sample management assembly (4310) so that sample management assembly (4310) can manipulate tissue samples. In accordance with this purpose, first rotation lock (4307) includes a protrusion (4308) that is generally configured to correspond certain geometric features of sample management assembly (4310) as will be described in greater detail below.

As can best be seen in FIG. 33, each rotation lock (4307, 4309) extends proximally from distal wall (4303) through almost the entire length of outer cover (4302) with each rotation lock (4307, 4309) terminating just distally of the proximal end of outer cover (4302). Additionally, each rotation lock (4307, 4309) extends inwardly from the inner diameter of outer cover (4302). As will be described in greater detail below, this proximal and inward extension of each rotation lock (4307, 4309) is configured to permit each rotation lock (4307, 4309) to engage certain geometric features of sample management assembly (4310).

Figure 34:
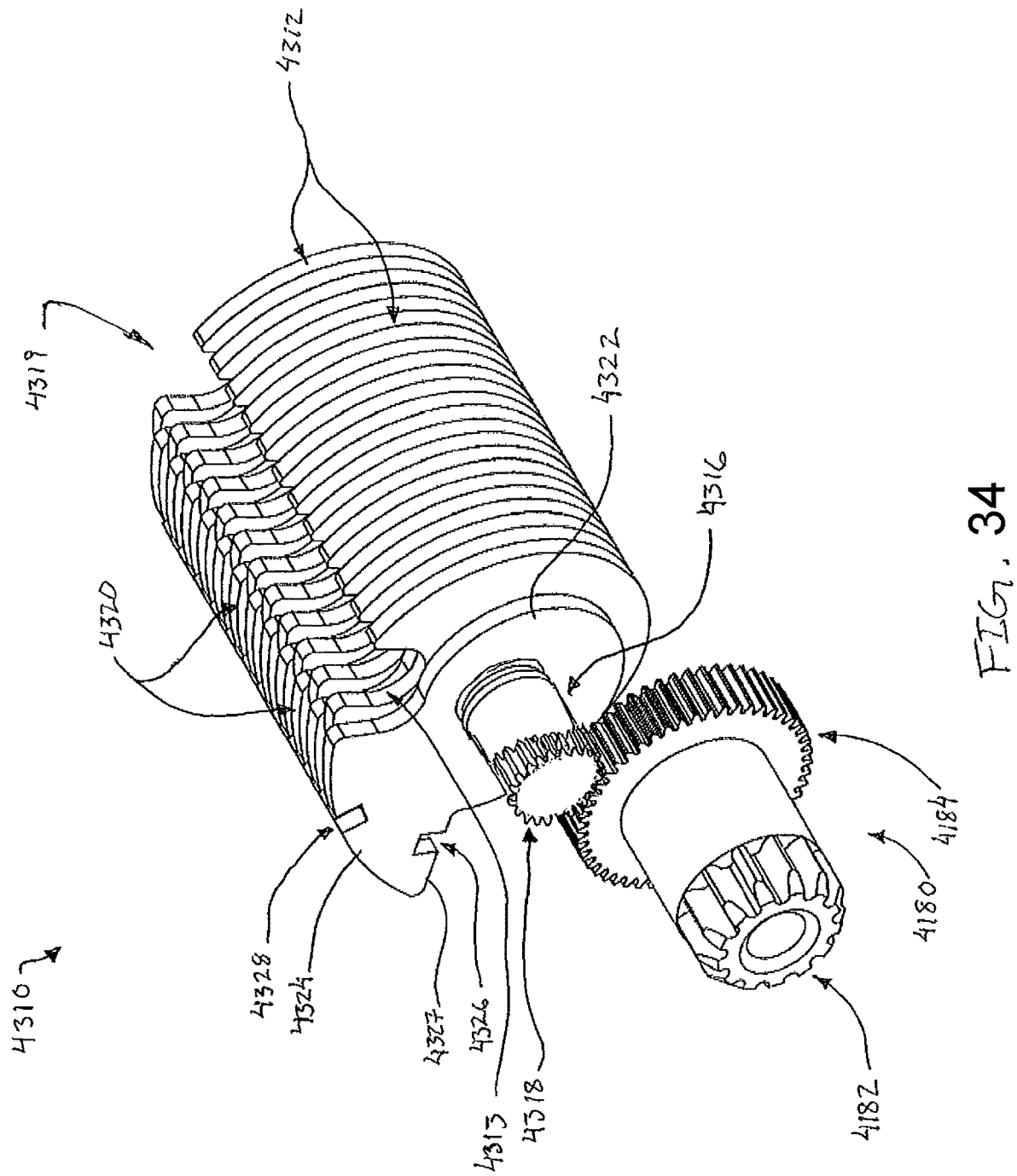
FIG. 34 depicts a perspective view of a sample management assembly for use with the tissue sample holder of FIG. 40.

Sample management assembly (4310) is best seen in FIG. 34. As can be seen, sample management assembly (4310) includes a series of alternating cam plates (4312, 4320). Generally, sample management assembly (4310) comprises a plurality of rotational cam plates (4312), and a plurality of stationary cam plates (4320). In the present aspect, each cam plate (4312, 4320) of a given type is generally identical to the other cam plates (4312, 4320) of the same type. Thus, sample management assembly (4310) of the present aspect is comprised of two distinct cam plates (4312, 4320) that repeat in an alternating fashion. Although only two distinct cam plates (4312, 4320) are used in the present aspect, it should be understood that in other aspects a number of different cam plates (4312, 4320) are incorporated into sample management assembly (4310) without departing from the functionality described below. All of the cam plates (4312, 4320) are connected axially via a drive shaft (4316). As will be described in greater detail below, drive shaft (4316) is generally configured to rotate rotational cam plates (4312) while stationary cam plates (4320) remain fixed within outer cover (4302).

Figure 35:
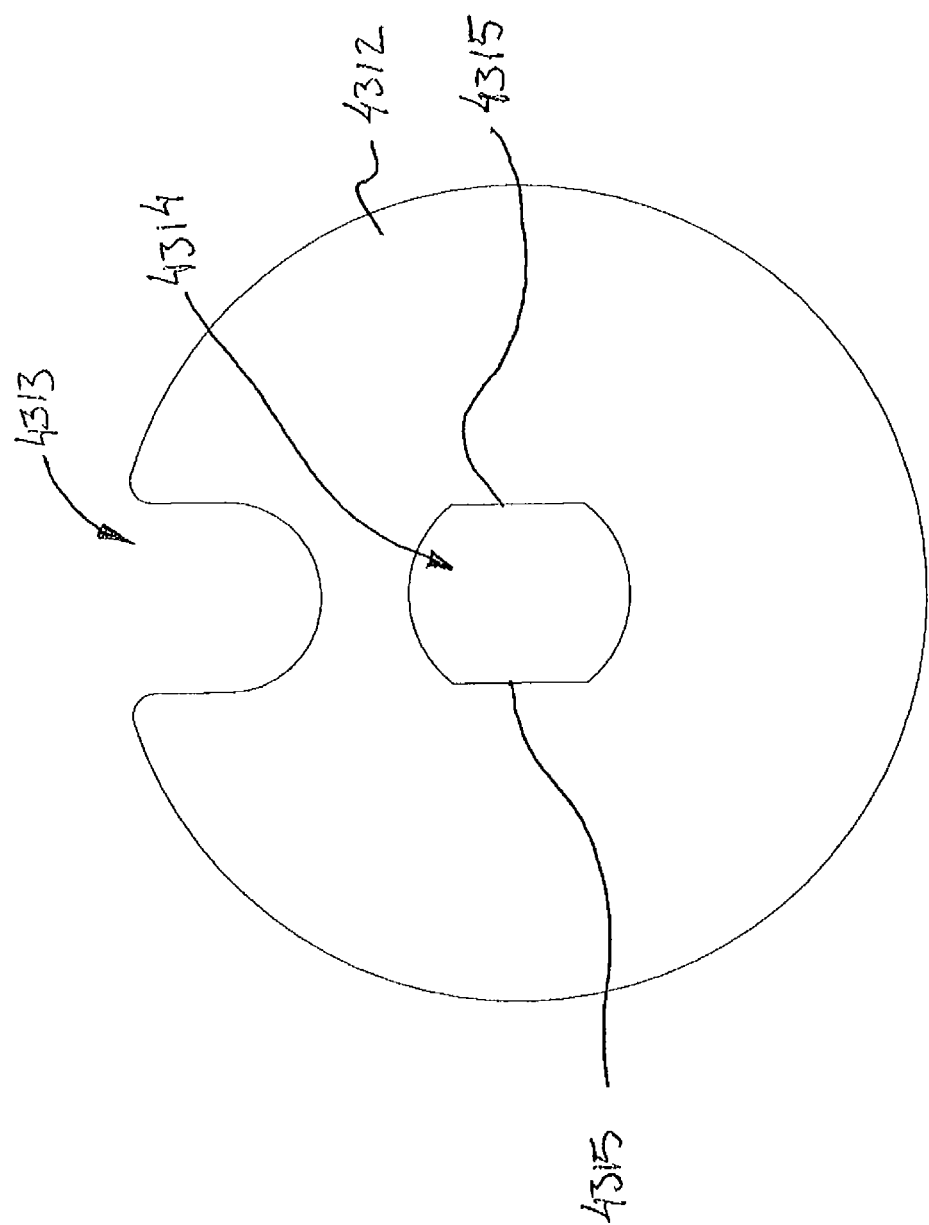
FIG. 35 depicts a front elevational view of a rotational cam plate of the sample management assembly of FIG. 34.

A single rotational cam plate (4312) is shown in FIG. 35. As can be seen, rotational cam plate (4312) generally comprises a cylindrical or coin-shaped configuration. Rotational cam plate (4312) includes a tissue opening (4313) and a shaft opening (4314). Tissue opening (4313) comprises a U-shaped opening. As will be described in greater detail below, each tissue opening (4313) of each rotational cam plate (4312) aligns to collectively define a tissue manipulation feature (4319). Thus, each tissue opening (4313) is generally sized to receive a single tissue sample. Alternatively, in other aspects, each tissue opening (4313) is sized to receive multiple tissue samples while still retaining the same functionality described in greater detail below.

Shaft opening (4314) comprises a generally circular shape with flats (4315) on adjacent sides of shaft opening (4314). As will be described in greater detail below, shaft opening (4314) is configured to correspond to the shape of the outer diameter of drive shaft (4316). Accordingly, it should be understood that shaft opening (4314) is configured to mate with drive shaft (4316). Additionally, because of the presence of flats (4315), shaft opening (4314) is configured to engage drive shaft (4316) such that rotation of drive shaft (4316) results in rotation of rotational cam plate (4312). It should be understood that while shaft opening (4314) is shown as having a specific geometry, any other suitable irregular geometry may be used. For instance, in some aspects shaft opening (4314) is configured with a starburst pattern that is configured to engage corresponding splines on the exterior of drive shaft (4316). Similarly, in other aspects shaft opening (4314) is configured with a keyway that is configured to engage a corresponding key protruding from the exterior of drive shaft (4316). Of course, any other suitable geometry of shaft opening (4314) may be used as will be apparent to those of ordinary skill in the art in view of the teachings herein.

Figure 36:
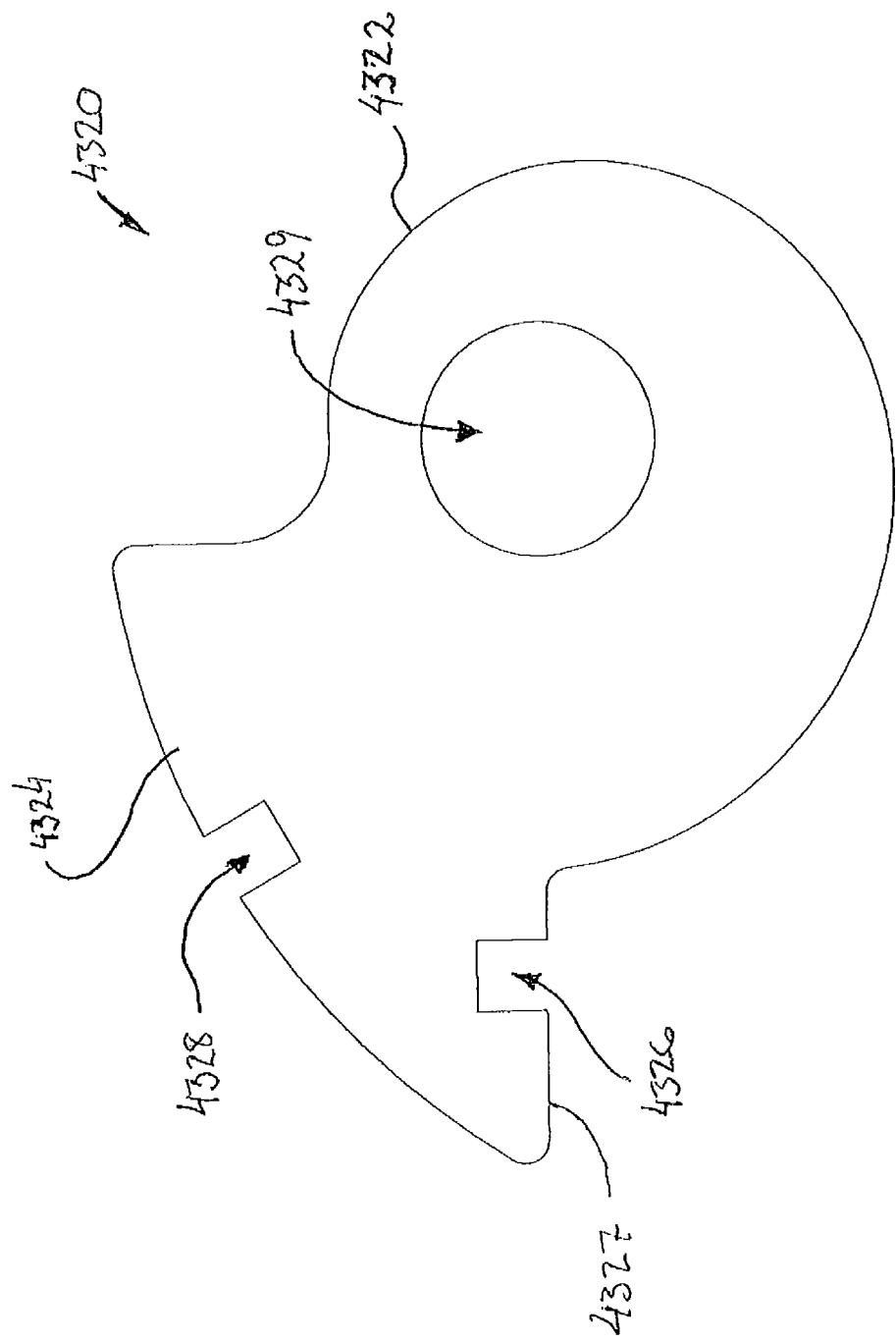
FIG. 36 depicts a front elevational view of a stationary cam plate of the sample management assembly of FIG. 34.

Stationary cam plate (4320) is best seen in FIG. 36. As can be seen, stationary cam plate (4320) comprises a camming portion (4322), a locking portion (4324), and a shaft opening (4329). Camming portion (4322) extends about 275° around the outer circumference of cam plate (4320) before transitioning to locking portion (4324). In other aspects, the particular amount of the outer circumference of cam plate (4320) through which camming portion (4322) extends may be anywhere between about 270° to about 330°. Camming portion (4322) progressively extends outwardly as camming portion (4322) extends around the outer circumference of cam plate (4320). In other words, as camming portion (4322) extends in a clockwise direction around the outer circumference of cam plate (4320) the radius of cam plate (4320) increases. As will be described in greater detail below, camming portion (4322) causes the effective size of tissue opening (4313) of rotational cam plate (4312) to decrease as each rotational cam plate (4312) is rotated relative to each stationary cam plate (4320). At the largest radius of camming portion (4322), stationary cam plate (4320) has a radius that is substantially equivalent to the radius of tissue opening (4313) of rotational cam plate (4312) such that the effective size of tissue opening (4313) will be substantially zero when aligned with the largest radius of camming portion (4322).

Locking portion (4324) extends outwardly from the center of rotational cam plate (4320) to a radius that is approximately equivalent to the inner radius of outer cover (4302). Locking portion (4324) of the present aspect includes a first lock opening (4326) and a second lock opening (4328). Lock openings (4326, 4328) are generally configured to receive rotation locks (4307, 4309) of outer cover. In particular, first lock opening (4326) is configured to receive protrusion (4308) of first rotation lock (4307). Additionally, first lock opening (4326) extends inwardly from a flat portion (4327) of locking portion (4324) such that flat portion (4327) abuts first rotation lock (4307). Similarly, second lock opening (4328) is configured to receive second rotational lock (4309) of outer cover (4302). Engagement between lock openings (4326, 4328) and rotation locks (4307, 4309) maintains locking portion (4324) in a stationary position. As will be described in greater detail below, this feature permits rotational cam plate (4312) to rotate relative to stationary cam plate (4320) to manipulate a tissue sample.

Shaft opening (4329) of stationary cam plate (4320) is generally circular in shape. Like shaft opening (4314) described above with respect to rotational cam plate (4312), shaft opening (4329) of stationary cam plate (4320) is configured to receive drive shaft (4316). However, because shaft opening (4329) of stationary cam plate (4320) is circular in shape and omits features similar to flats (4315), drive shaft (4316) freely rotates relative to shaft opening (4329). Because each stationary cam plate (4320) is generally fixed relative to outer cover (4302), it should be understood that each stationary cam plate (4320) generally acts to stabilize drive shaft (4316) as drive shaft is rotated within shaft opening (4329) thereby maintaining the axial position of drive shaft (4316).

Figure 37:
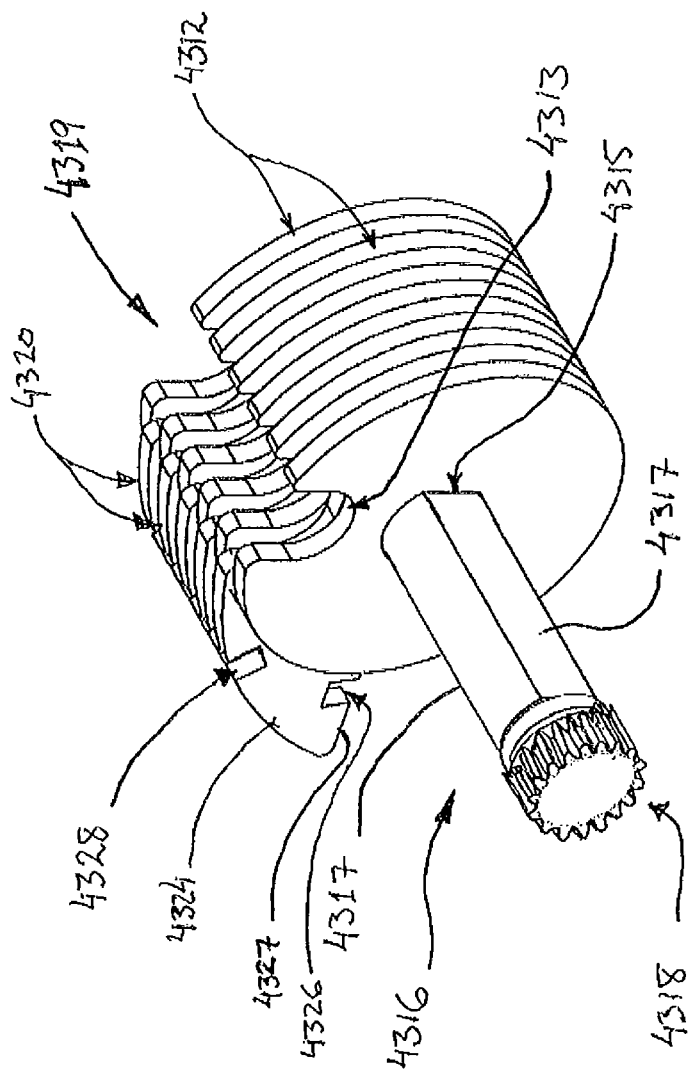
FIG. 37 depicts a perspective view of the sample management assembly of FIG. 34, with at least some cam plates removed.

FIG. 37 shows a partial view of drive shaft (4316) with some cam plates (4312, 4320) attached to drive shaft (4316) and some cam plates (4312, 4320) removed from drive shaft (4316). As can be seen, drive shaft (4316) comprises a generally cylindrical structure that extends through a length greater than the combined length of the combination of cam plates (4312, 4320). The generally cylindrical shape of drive shaft (4316) is circumscribed on two sides of drive shaft (4316) by a pair of flats (4317). Flats (4317) are generally configured to key with corresponding flats (4315) of shaft openings (4314) of each rotational cam plate (4312). Thus, drive shaft (4316) is configured to communicate torque to each rotational cam plate (4312) to thereby rotate each rotational cam plate (4312).

Figure 38:
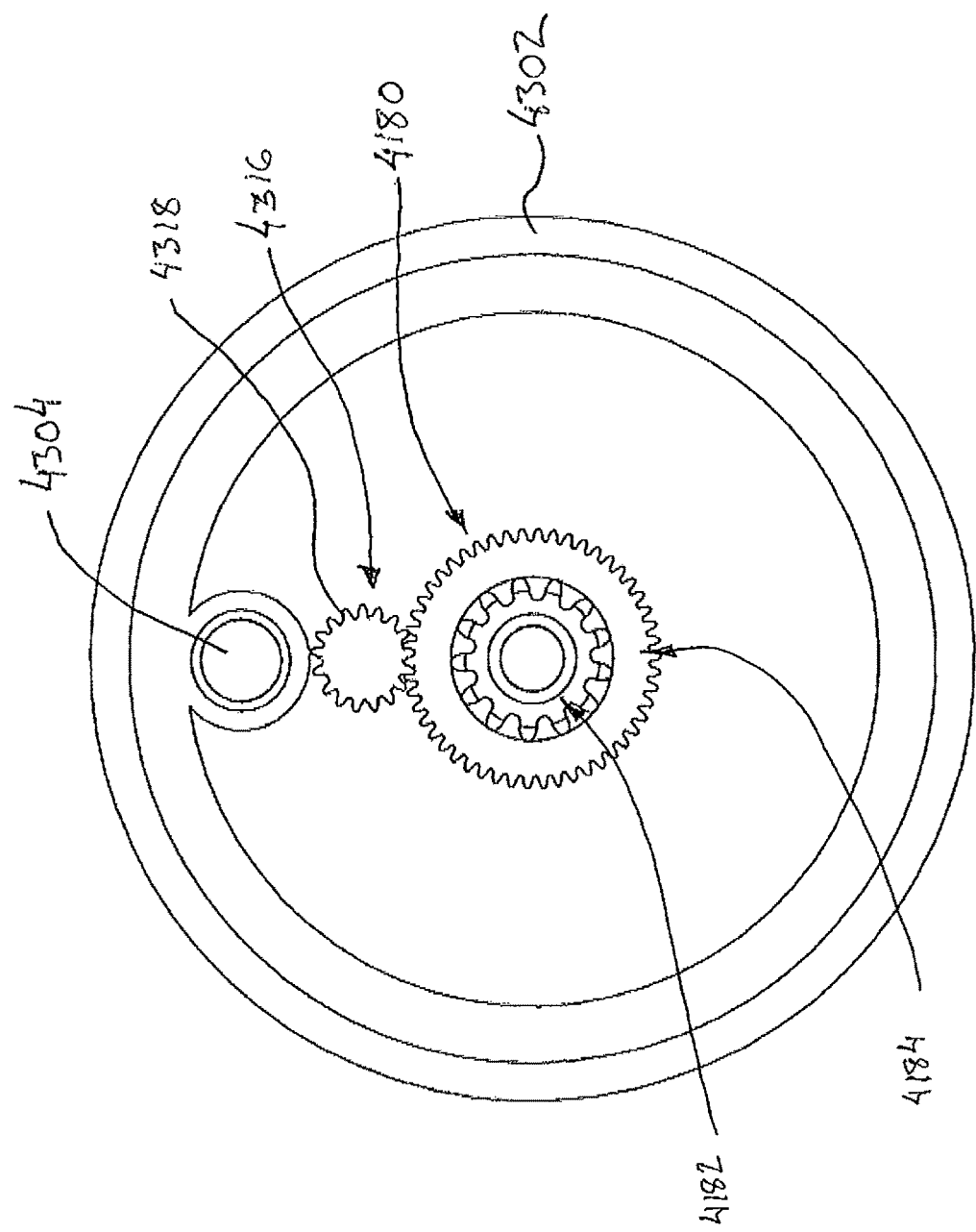
FIG. 38 depicts a front elevational view of the tissue sample holder of FIG. 28.

Drive shaft (4316) further includes a gear (4318) integrally formed in the distal end of drive shaft (4316). Gear (4318) is configured to engage with rotation member (4180) to transfer rotational force from biopsy device to drive shaft (4316). As can be seen in FIG. 38, when sample management assembly (4310) is fully assembled within outer cover (4302), drive shaft (4316) protrudes distally through shaft opening (4305) of distal wall (4303) of outer cover (4302). Rotation member (4180) is correspondingly rotationally mounted on pin (4306) of outer cover (4302) such that rotation member (4180) is rotatable relative to outer cover (4302). Rotation member (4180) is thereby positioned to engage gear (4318) of drive shaft (4316) to rotate drive shaft (4316) relative to outer cover (4302).

Figure 39:
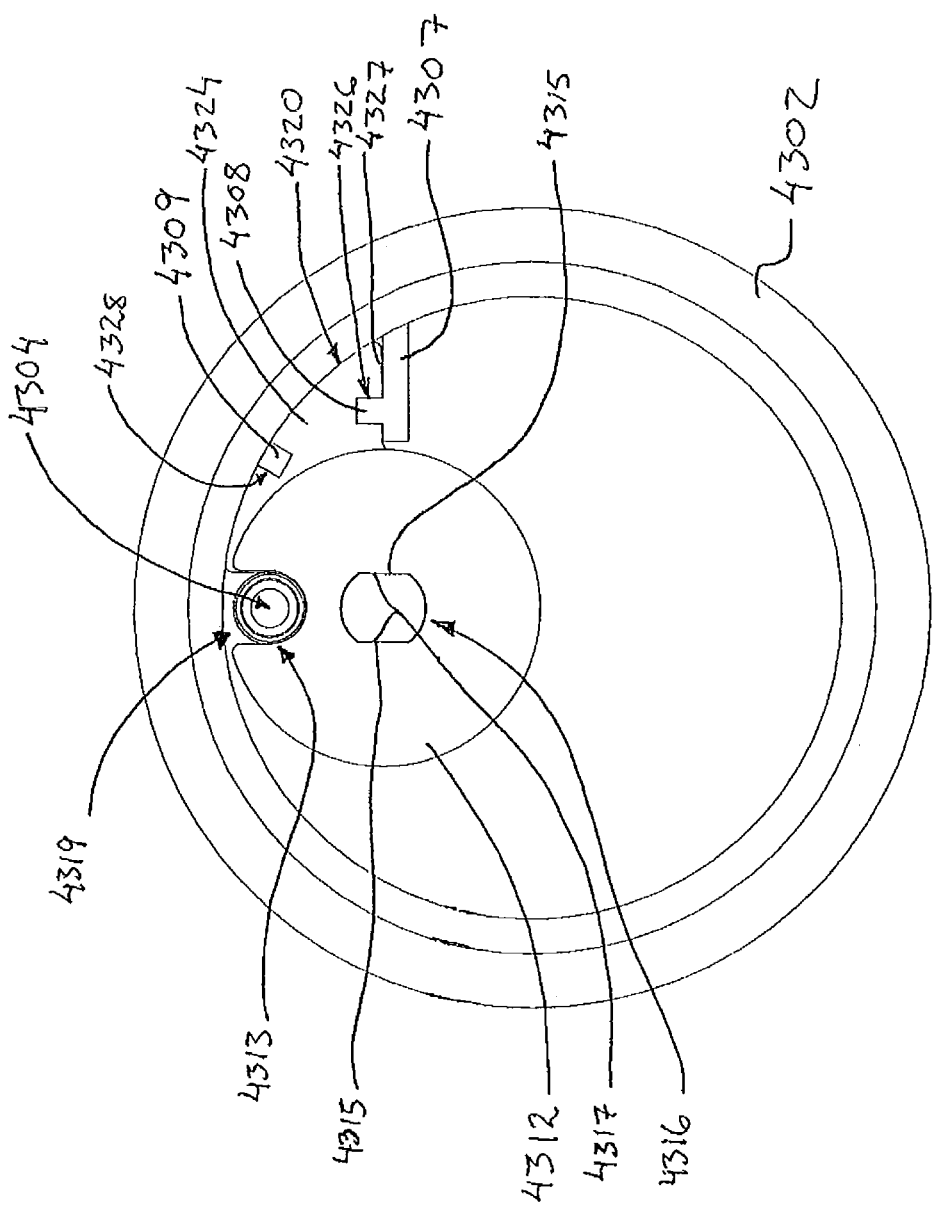
FIG. 39 depicts a rear elevational view of the tissue sample holder of FIG. 28, with a sample basket removed.

FIG. 39 shows sample management assembly (4310) fully assembled in outer cover (4302) from an opposite direction relative to the view shown in FIG. 38. As can be seen, when sample management assembly (4310) is disposed within outer cover (4302), each stationary cam plate (4320) is held in position by rotation locks (4307, 4309) of outer cover (4302). Stationary cam plates (4320) correspondingly maintain the axial position of drive shaft (4316) such that drive shaft (4316) is aligned with shaft opening (4305) of outer cover (4302). Rotational cam plates (4312) are correspondingly held in position by drive shaft (4316) such that each tissue opening (4313) is configured to align with cutter bore (4304) of outer cover (4302) (provided that rotational cam plates (4312) are rotated into the position shown in FIG. 39).

Figure 40:
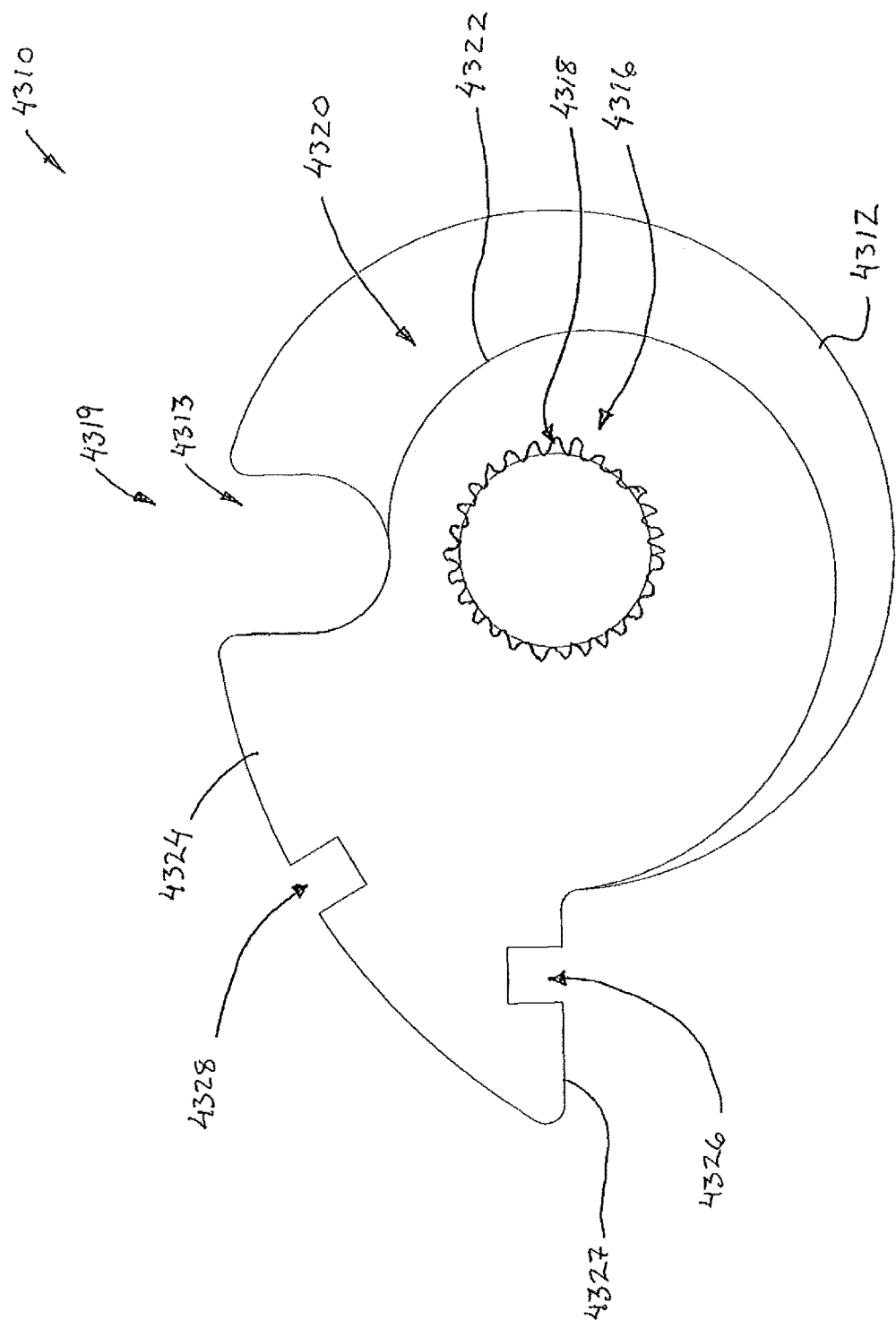
FIG. 40 depicts a front elevational view of the sample management assembly of FIG. 34, with the sample management assembly in a tissue receiving position.

FIGS. 40-43 show an exemplary mode of operation of sample management assembly (4310). As can be seen in FIG. 40, sample management assembly (4310) initially begins with each tissue opening (4313) positioned into alignment with a 12 o'clock position. Although not shown, it should be understood that in this position, each tissue opening (4313) of rotational cam plates (4312) is aligned with cutter bore (4304) of outer cover (4302). Accordingly, tissue manipulation feature (4319) of the combination of all of the rotational cam plates (4312) is aligned with cutter bore (4304) such that sample management assembly (4310) is in a configuration to receive a tissue sample.

Tissue management assembly (4310) may be transitioned to the 12 o'clock position shown in FIG. 40 by rotating drive shaft (4316) to thereby rotate rotational cam plates (4312). Once positioned, a tissue sample may be acquired using biopsy device equipped with any one of probes described above and/or in U.S. Pub. No. 2014/0039343. The tissue sample may then be communicated through the cutter, through the distal wall (4303) of outer cover (4302) and into tissue manipulation feature (4319) as defined by rotational cam plates (4312). Once a tissue sample is disposed therein, an operator may inspect the tissue sample by visual inspection. It should be understood that outer cover (4302) is transparent as the outer cover is similarly described above. Additionally, in other aspects, sample management assembly (4310) is optionally equipped with various other tissue analysis features described herein.

Figure 41:
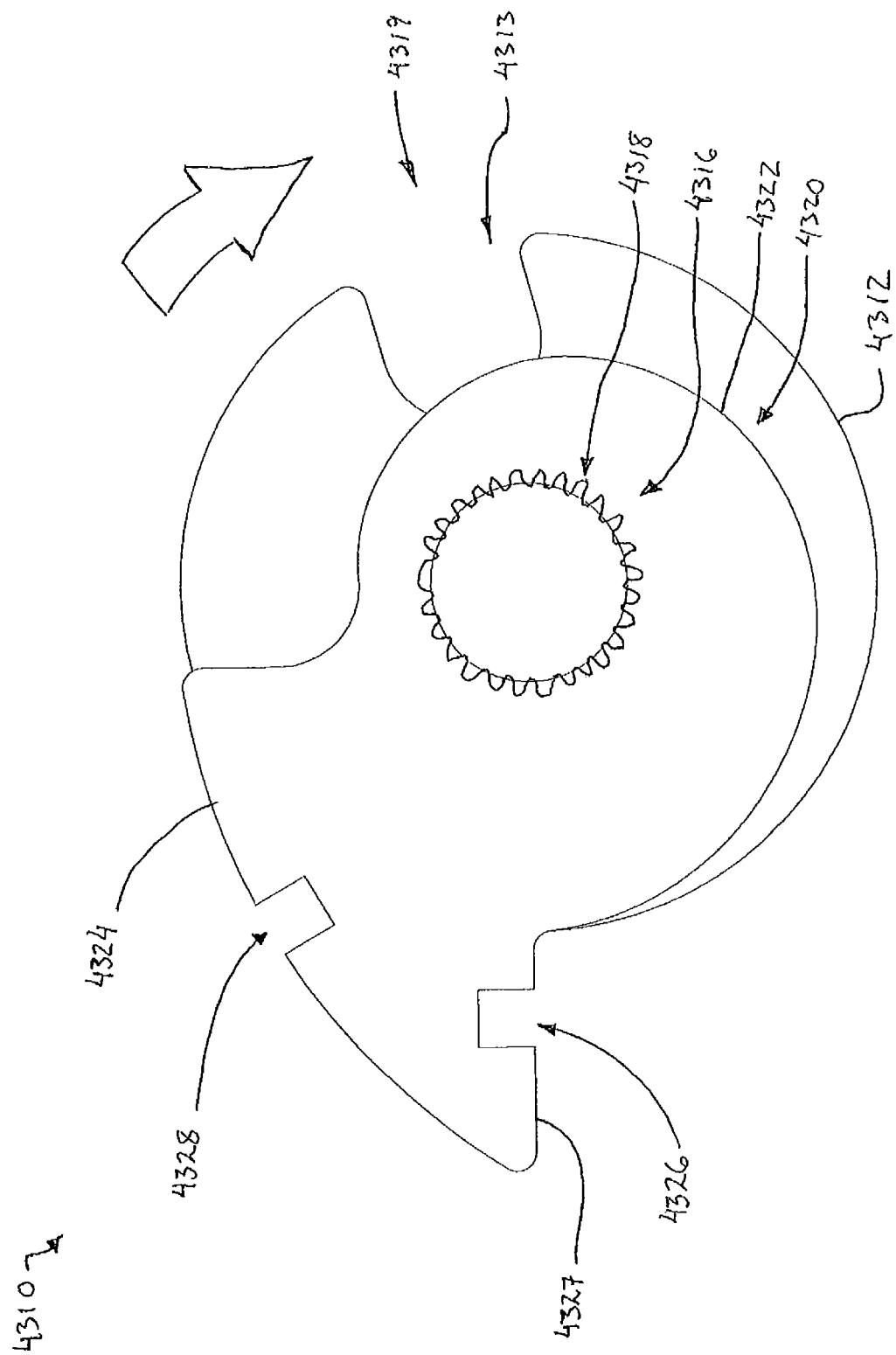
FIG. 41 depicts another front elevational view of the sample management assembly of FIG. 34, with the sample management assembly in an intermediate position.
Figure 42:
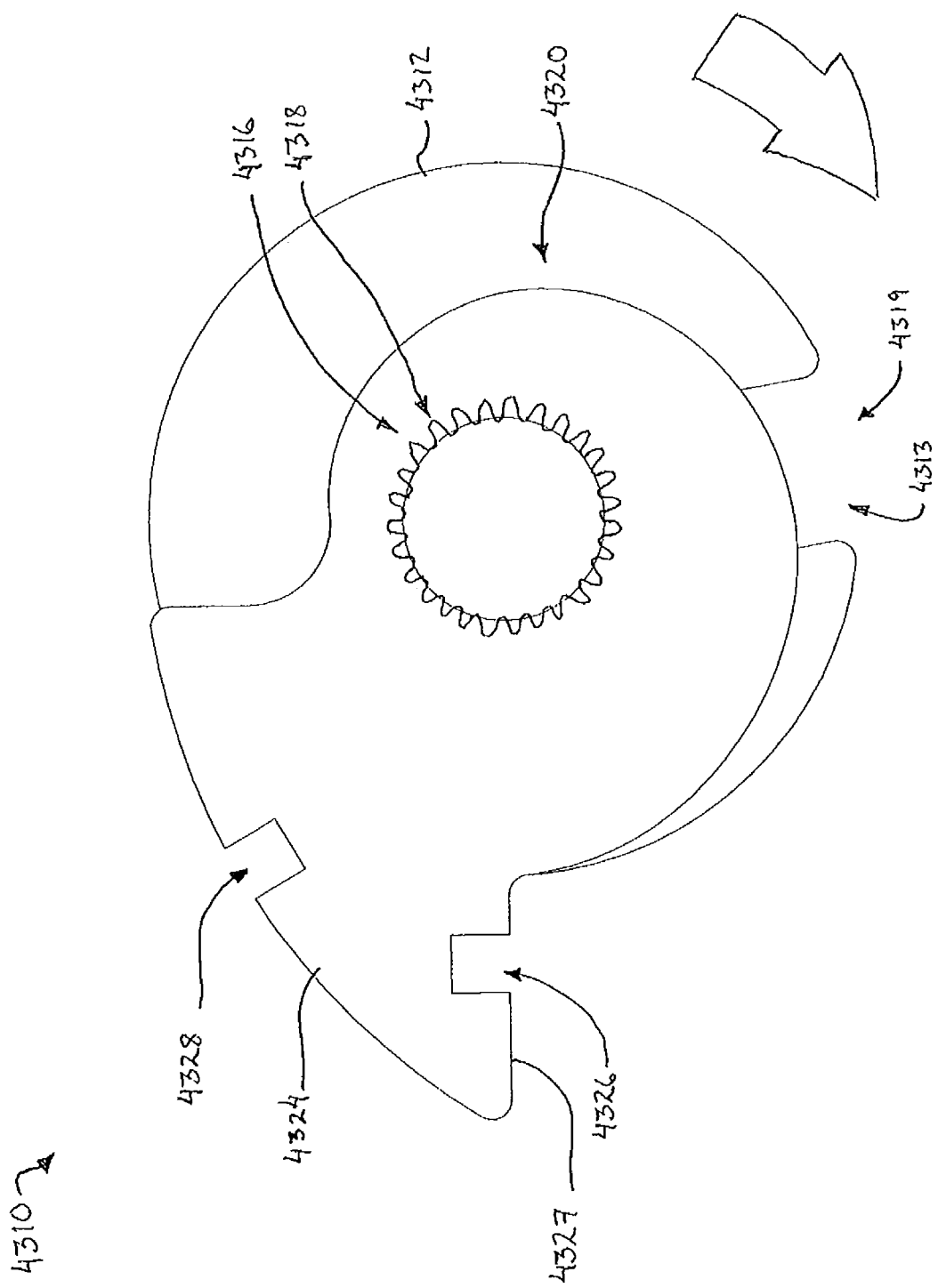
FIG. 42 depicts still another front elevational view of the sample management assembly of FIG. 34, with the sample management assembly in a first tissue ejection position.
Figure 43:
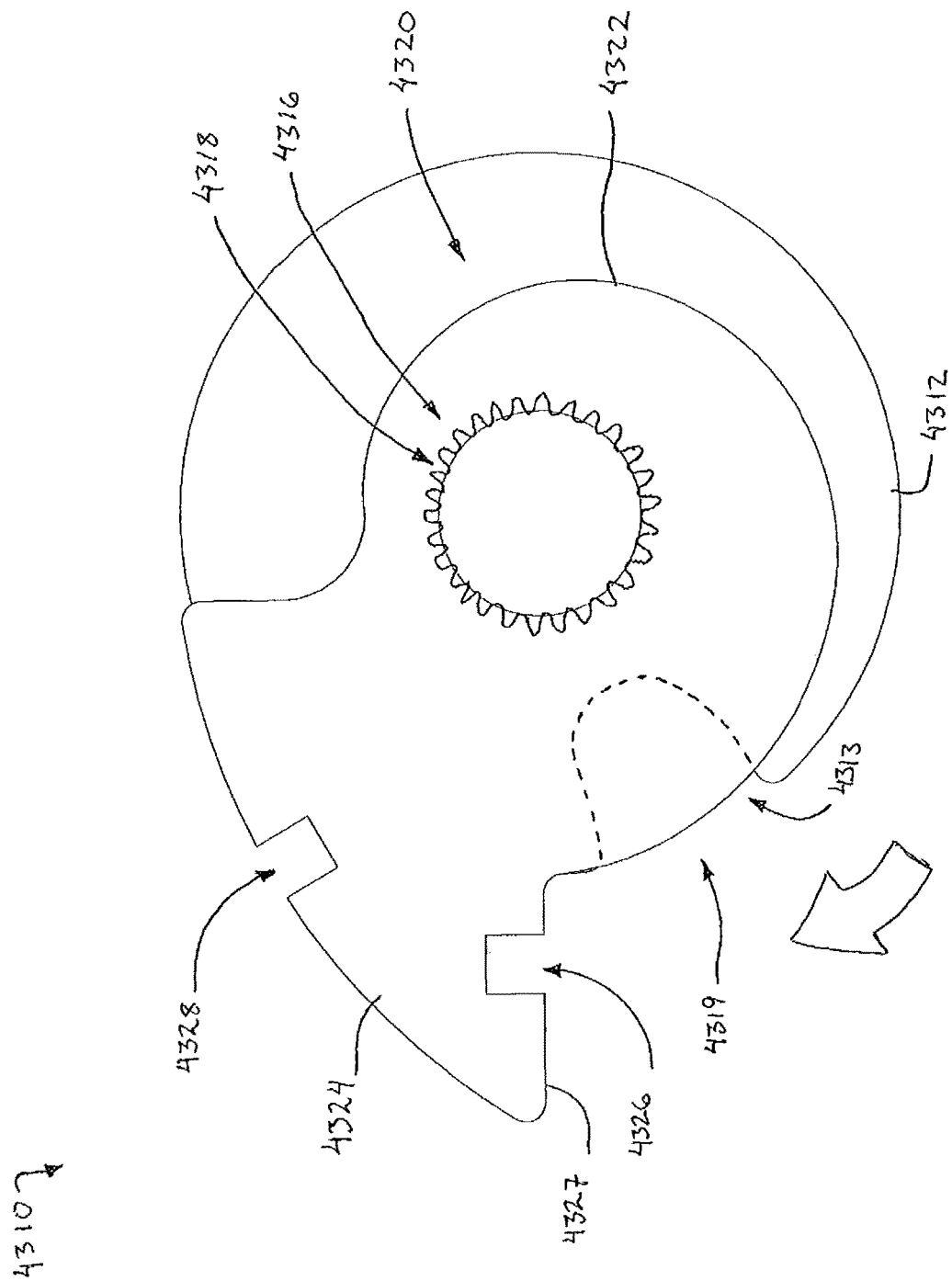
FIG. 43 depicts yet another front elevational view of the sample management assembly of FIG. 34, with the sample management assembly in a second tissue ejection position.
Figure 44:
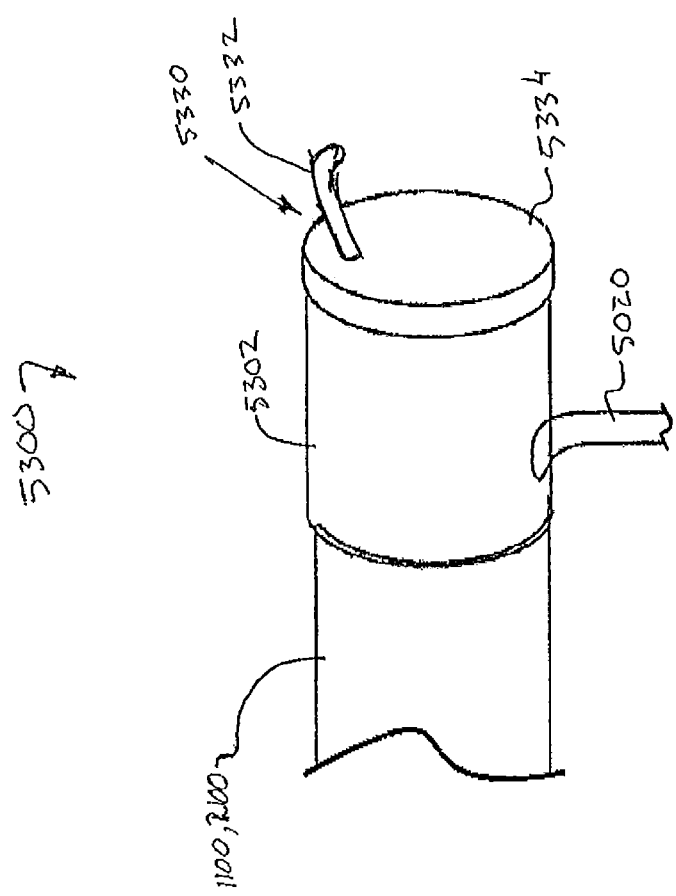
FIG. 44 depicts a perspective view of still another exemplary alternative tissue sample holder for use with any one of the probes.

Once an operator has competed analysis, it may be desirable to deposit the tissue sample into sample basket (4330) and thereby prepare sample management assembly (4310) for receipt of another tissue sample. To transport the tissue sample into sample basket (4330), rotational cam plates (4312) are rotated via drive shaft (4316). In particular, as can be seen in FIGS. 41-43, drive shaft (4316) is rotated in a counter clockwise direction via rotation member (4180) to drive each rotational cam plate (4312) in a rotary motion relative to each stationary cam plate (4320). As each rotational cam plate (4312) is rotated relative to each stationary cam plate (4320), the effective size of tissue manipulation feature (4319) progressively decreases due to the progressively increasing radius of each stationary cam plate (4320).

Once each rotational cam plate (4312) is rotated into the position shown in FIG. 42, the tissue sample may fall into sample basket (4330) under the force of gravity. However, depending on the particular characteristics of the tissue sample, in some instances the tissue sample may be susceptible to light adhesion such that the force of gravity is insufficient to release the tissue sample into sample basket (4330). Additionally, in some uses tissue sample holder (4300) may be oriented such that the force of gravity is applied in a direction up the page of FIG. 42. In such circumstances, the tissue sample gravity will not force the tissue sample into sample basket (4330) regardless of the properties of the tissue sample. In such instances, rotation of rotational cam plates (4312) may continue relative to stationary cam plates (4320) to the position shown in FIG. 43.

Once rotational cam plates (4312) have been rotated to the position shown in FIG. 43, the effective size of tissue manipulation feature (4319) is reduced to nearly zero such that each tissue opening (4313) of each rotational cam plate (4312) is disposed substantially within stationary cam plates (4320). Thus, as each rotational cam plate (4312) rotates toward the position shown in FIG. 43, each stationary cam plate (4320) will begin to engage the tissue sample and thereby mechanically force the tissue sample away from rotational cam plates (4312). Once the tissue sample is separated from rotational cam plates (4312), the tissue sample will drop into sample basket (4330) or remain lightly adhered to stationary cam plates (4312). Rotational cam plates (4312) can then continue to rotate back to the position shown in FIG. 40 with sample manipulation feature (4319) cleared of the tissue sample and prepared for receipt of another tissue sample.

Once sample manipulation feature (4319) has been cleared by rotation of rotational cam plates (4312) through the sequence described above, another tissue sample may be collected and deposited in sample basket (4330) by following the same sequence described above. The sequence may then be repeated until sample basket (4330) is full, or until an operator has completed the biopsy procedure.

Figure 45:
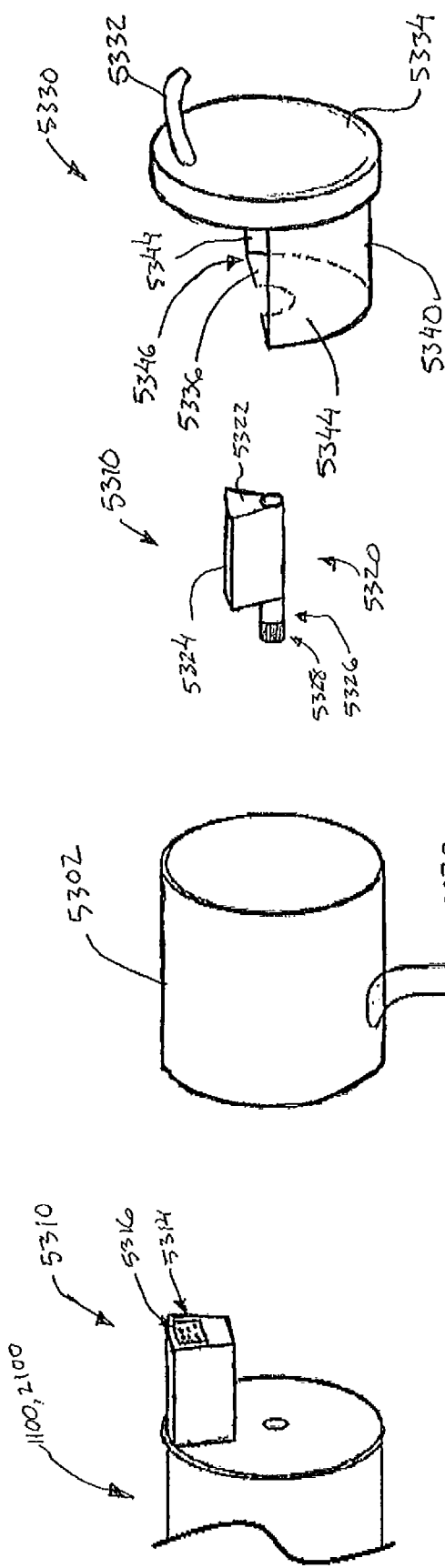
FIG. 45 depicts an exploded perspective view of the tissue sample holder of FIG. 44.
Figure 46:
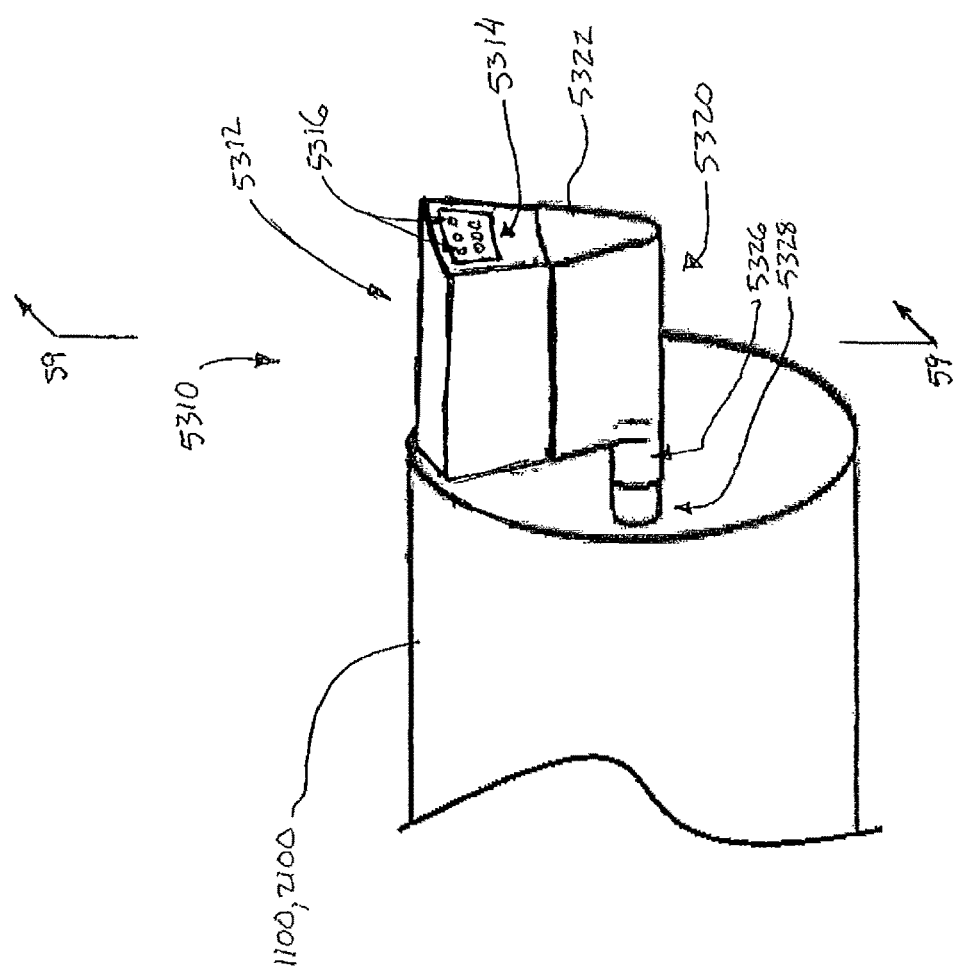
FIG. 46 depicts a perspective view of a sample management assembly for use with the tissue sample holder of FIG. 44.

FIGS. 45-46 show an alternative sample management assembly (5310) that may be readily incorporated into any one of the probes described above and/or in U.S. Pub. No. 2014/0039343. Sample management assembly (5310) is incorporated into a tissue sample holder (5300) that is substantially similar to tissue sample holders (1300, 2300) described above. It should be understood that unless otherwise specifically noted herein, tissue sample holder (5300) is identical to tissue sample holders (1300, 2300) described above. For instance, tissue sample holder (5300) of the present aspect is configured to store tissue samples in a single bulk tissue sample chamber (5346). As is best seen in FIG. 45, tissue sample holder (5300) comprises a sample basket (5330), a sample management assembly (5310), and an outer cover (5302). Sample basket (5330) is substantially similar to sample baskets (1330, 2330) described above. For instance, basket (5330) is generally configured to hold a plurality of tissue samples in a single tissue sample chamber (5346). As can be seen, basket (5330) comprises a grip (5332) and a proximal wall (5334). Grip (5332) extends proximally from proximal wall (5334) and is configured to be grasped by an operator to manipulate basket (5330). As will be described in greater detail below, grip (5332) of the present aspect is additionally configured to provide a fluid channeling function. Proximal wall (5334) defines a channel (not shown) along the outer edge of the distal side of proximal wall (5334). The channel is configured to receive at least a portion of outer cover (5302) to fluidly seal the proximal end of tissue sample holder (5300) when basket (5330) is disposed in outer cover (5302). Although not shown, it should be understood that the channel can be equipped with gaskets or other sealing elements to further promote sealing between basket (5330) and outer cover (5302).

A pair of sidewalls (5344) and a lower floor (5340) extend distally from proximal wall (5334). In the present aspect, sidewalls (5344) and lower floor (5340) are defined by a single semi-circular shaped member. However, it should be understood that in other aspects sidewalls (5334) and lower floor (5340) are more discretely defined by a square or rectangular cross-section. Although not shown, it should be understood that in some aspects basket (5330) includes an intermediate floor (not shown) disposed above lower floor (5340) as similarly described above with respect to baskets (1330, 2330).

A distal wall (5336) is disposed at the distal end of basket (5330). Distal wall (5336) of the present aspect defines a semi-circular shape that is configured to receive at least a portion of sample management assembly (5310), as will be described in greater detail below. Distal wall (5336), proximal wall (5334), sidewalls (5344), and the intermediate floor together define a tissue sample chamber (5346). Tissue sample chamber (5346) is generally configured to receive a plurality of tissue samples therein. In the present aspect, tissue sample chamber (5346) is configured to receive anywhere between about 20 to about 50 tissue samples. Of course, in other aspects tissue sample chamber (5346) may be configured to receive any other suitable number of tissue samples.

Outer cover (5302) of the present aspect is substantially similar to outer covers (1302, 2302) described above. For instance, outer cover (5302) of the present aspect comprises a generally hollow cylindrical shape that is configured to receive basket (5330) and sample management assembly (5310). Additionally, outer cover (5302) of the present aspect is substantially transparent to permit analysis of tissue samples through outer cover (5302). However, unlike outer covers (1302, 2302) described above, outer cover (5302) of the present aspect is connected directly to tube (5020) to supply vacuum directly to outer cover (5302). Although outer cover (5302) of the present aspect is shown as connecting directly to tube (5020), it should be understood that no such limitation is intended. For instance, in some aspect tube (5020) is connected to outer cover (5302) and the rest of tissue sample holder (5300) as similarly described above with respect to tissue sample holders (1300, 2300).

Sample management assembly (5310) is generally configured to selectively deposit tissue samples into sample basket (5330) while overcoming difficulties associated with the tendency of tissue samples to lightly adhere or stick to surfaces. As can best be seen in FIGS. 45-47, sample management assembly (5310) generally comprises a sample receiving member (5312) and a release member (5320). Sample receiving member (5312) of the present aspect extends proximally from any one of probes described above and/or in U.S. Pub. No. 2014/0039343. To permit analysis of any tissue samples received in sample receiving member (5312), it should be understood that sample receiving member (5312) is generally transparent. Thus, an operator may visually analyze tissue samples as they are collected in sample receiving member (5312).

Figure 47:
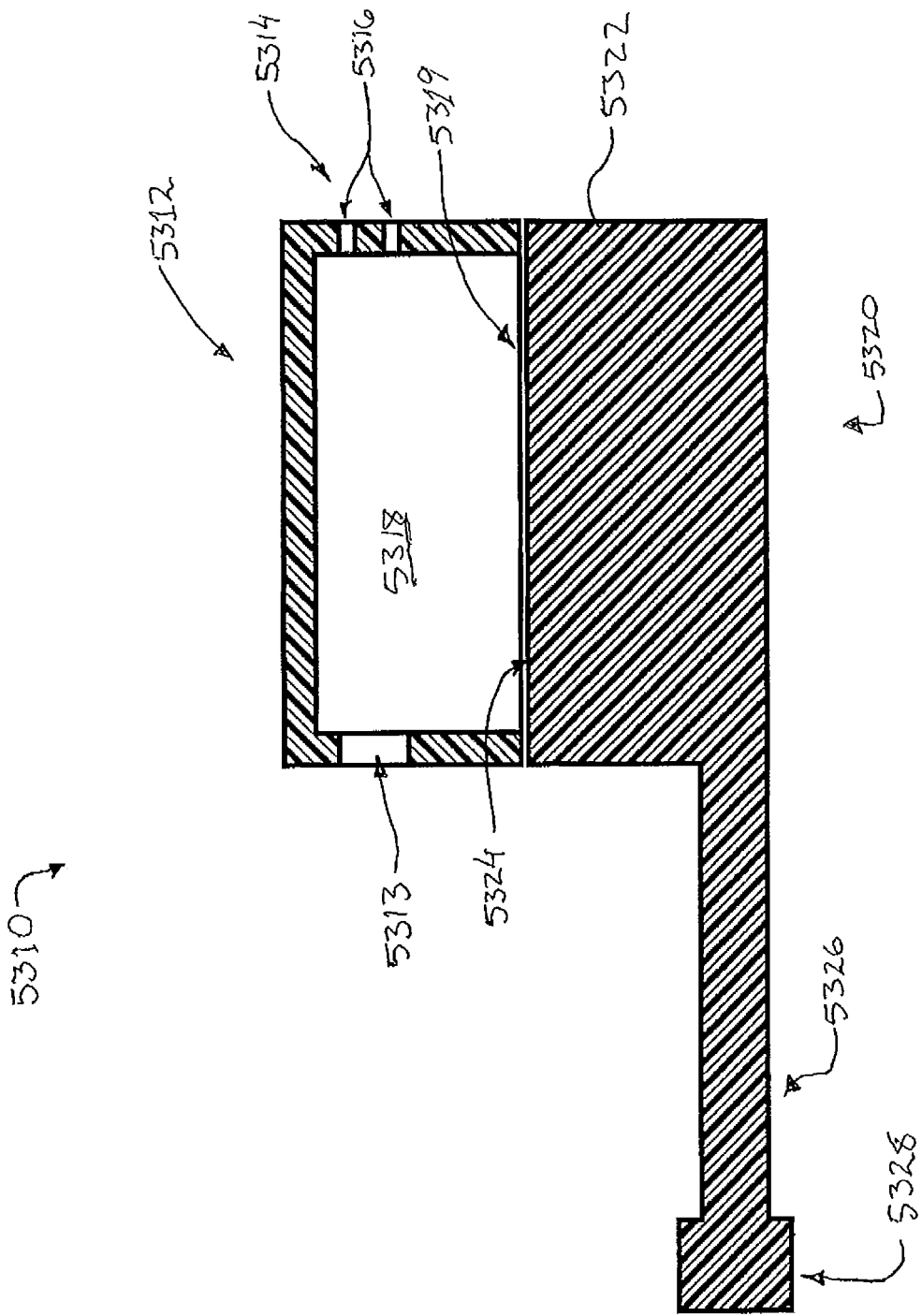
FIG. 47 depicts a side cross-sectional view of the sample management assembly of FIG. 46, the cross-section taken along line 59-59 of FIG. 46.

Sample receiving member (5312) of the present aspect is in direct communication with the cutter of any one of probes described above and/or in U.S. Pub. No. 2014/0039343. In particular, as can be seen in FIG. 47, the distal end of sample receiving member (5312) includes a sample passage (5313) that is configured to communicate tissue samples into an interior chamber (5318) defined by tissue receiving member (5312). In order to receive tissue samples, sample receiving member (5312) generally comprises a hollow box or container with a generally trapezoidal cross-sectional shape. In the present aspect, interior chamber (5318) is generally sized to receive at least one tissue sample. In other aspects, interior chamber (5318) is sized to receive any suitable number of tissue samples. Alternatively, in other aspects interior chamber (5318) is sized to closely approximate the size of a single tissue sample such that interior chamber (5318) is sized to receive only a single tissue sample.

To complete the vacuum circuit between the cutter and tube (5020), sample receiving member (5312) includes a fluid filter (5314) disposed on the distal end of sample receiving member (5312). Fluid filter (5314) comprises a plurality of openings (5316) extending through the proximal end of sample receiving member (5312). Openings (5216) are generally sized to permit the flow of fluid or tissue particles therethrough but block tissue samples.

The underside of sample receiving member (5312) includes an open bottom (5319). As will be described in greater detail below, open bottom (5319) is generally closed by release member (5320). However, in operation of sample management assembly (5310), release member (5320) can move relative to sample receiving member (5312) to expose open bottom (5319). Thus, it should be understood that open bottom (5319) is generally selectively transitionable between an open and closed configuration to permit receiving and releasing of tissue samples.

Release member (5320) comprises a blocking portion (5322) and an actuation portion (5326). Blocking portion (5322) comprises a solid block with a generally triangular lateral cross-sectional shape. Blocking portion (5322) defines an upper surface (5324) that is configured to correspond to the size and shape of open bottom (5319) in sample receiving member (5312). Although not shown, it should be understood that in some aspects upper surface (5324) includes certain sealing features such as gaskets, wiper seals, and the like that are configured to seal open bottom (5319) relative to the interior of outer cover (5302). Various sealing features that may be incorporated into upper surface (5324) will be apparent to those of ordinary skill in the art in view of the teachings herein.

Actuation portion (5326) of release member (5320) extends distally from blocking portion (5322). Actuation portion (5326) is generally configured to transmit torque to blocking portion (5322) to thereby rotate blocking portion (5322). In particular, the distal end of actuation portion (5326) is equipped with a gear (5328). Gear (5328) is configured to be driven by various components of biopsy device such that biopsy device can drive gear (5328) to rotate blocking portion (5322) via actuation portion (5326). As will be described in greater detail below, this permits biopsy device to selectively block and unblock open bottom (5319) of sample receiving member (5312) using release member (5320).

Figure 48:
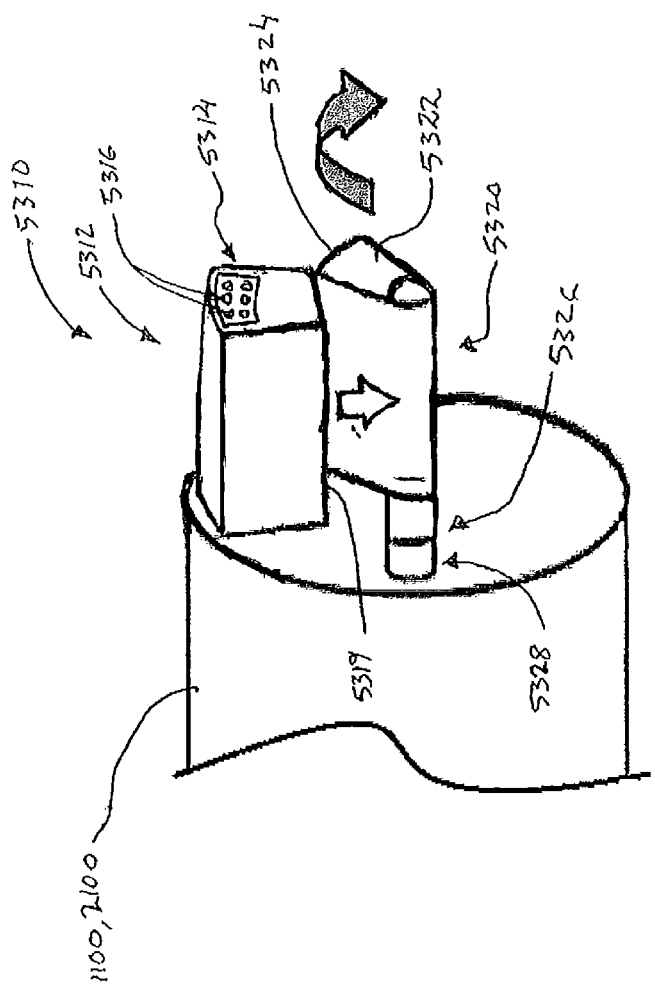
FIG. 48 depicts another perspective view of the sample management assembly of FIG. 46, with the sample management assembly in a tissue releasing configuration.

An exemplary mode of operation of sample management assembly (5310) can be seen by comparing FIGS. 46-48. As can be seen in FIG. 46, tissue management assembly (5310) initially begins in a tissue receiving state. In the tissue receiving state, release member (5320) is positioned such that blocking portion (5322) is positioned directly under open bottom (5319) of sample receiving member (5312) to substantially seal open bottom (5319).

When sample management assembly (5310) is in the tissue receiving state, one or more tissue samples may be communicated from the cutter and into interior chamber (5318) of sample receiving member (5312). In particular, vacuum may be applied to tube (5020) and travel into outer cover (5302). Vacuum may then pass through openings (5316) of fluid filter (5314) and into interior chamber (5318). Because interior chamber (5318) is in direct communication with the cutter through sample passage (5313), vacuum will pass through interior chamber (5318) and into the cutter to transport one or more tissue samples into interior chamber (5318).

Once one or more tissue samples are received within interior chamber (5318), an operator may visually analyze the one or more tissue samples. It should be understood that in some aspects sample receiving member (5312) is also equipped with various other sample analysis features described herein (e.g., bioimpedance). Thus, during this stage, the one or more tissue samples can also be analyzed using any other sample analysis feature.

At the conclusion of sample analysis, an operator may desire to empty the contents of interior chamber (5318) into sample basket (5330). To empty interior chamber (5318) an operator can selectively transition sample management assembly (5310) into a sample release configuration shown in FIG. 48. In the sample release configuration, release member (5320) is rotated relative to sample receiving member (5312) via gear (5328) to expose open bottom (5319) of sample receiving member (5312). This will permit the one or more tissue samples to drop into sample basket (5330). Additionally, if any tissue samples stick or otherwise adhere to upper surface (5324) of blocking portion (5322) such samples will be removed as blocking portion (5322) is rotated relative to sample receiving member (5312). In particular, because upper surface (5324) is closely associated with open bottom (5319), sample receiving member (5312) will push any tissue sample off of upper surface (5324) as upper surface (5324) is moved relative to open bottom (5319).

Once the one or more tissue samples have been deposited in sample basket (5330), sample management assembly (5310) may be returned to the tissue receiving state shown in FIG. 46. Once back in the sample receiving state, additional tissue samples may be acquired by repeating the process described above. This process may be repeated by an operator several times until sample basket (5330) is full or until the conclusion of the biopsy procedure.

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A biopsy device, comprising: (a) a body; (b) a needle extending distally from the body; (c) a cutter movable relative to the needle and in communication with the needle for transporting tissue samples; and (d) an analysis area disposed proximally of the cutter and in communication with the needle to receive a tissue sample cut by the cutter for analysis by a user; (e) a valve disposed proximally of the analysis area and configured to alternate between an open configuration and a closed configuration; and (f) a tissue sample holder disposed proximally of the valve and fixedly attached to the body, wherein the valve is configured to permit analysis of the sample disposed in the analysis area when the valve is in the closed configuration and to permit the tissue sample to be passed into the tissue sample holder when the valve is in the open configuration.

Example 2

The biopsy device of Example 1, wherein at least a portion of the tissue sample holder is releasably attached to the body.

Example 3

The biopsy device of Example 2, wherein the valve incudes a movable filter, wherein the analysis area defines a single tissue sample chamber, wherein the single tissue sample chamber is in selective communication with the tissue sample holder via selective movement of the filter.

Example 4

The biopsy device of any one or more of Example 1, wherein the valve includes a first disk, wherein the first disk includes a plurality of outer filter portions and a plurality of openings, wherein each outer filter portion is positioned adjacent to a corresponding opening such that the plurality of outer filter portions and the plurality of openings form an alternating arrangement.

Example 5

The biopsy device of Example 4, wherein the first disk is configured to rotate relative to the cutter to successively and alternatingly align an outer filter portion or opening with the cutter.

Example 6

The biopsy device of Example 5, wherein the valve is configured to provide the closed configuration when an outer filter portion of the first disk is aligned with the cutter, wherein the valve is configured to provide the open configuration when an opening of the first disk is aligned with the cutter.

Example 7

The biopsy device of Example 6, wherein the valve further includes a second disk, wherein the second disk includes a plurality of vacuum chambers and a plurality of openings.

Example 8

The biopsy device of Example 7, wherein the first disk is fixedly secured to the second disk.

Example 9

The biopsy device of Example 7, wherein each vacuum chamber of the second disk is configured to correspond to a respective outer filter portion of the first disk, wherein each opening of the second disk is configured to correspond to a respective opening of the second disk.

Example 10

The biopsy device of Example 9, wherein the first disk further includes a filter ring, wherein the filter ring is defined by a plurality of vacuum openings extending through the first disk, wherein each vacuum chamber of the second disk is configured to redirect vacuum flowing through the filter ring of the first disk to a respective filter portion of the first disk.

Example 11

The biopsy device of anyone or more of Examples 1 through 10, wherein the analysis area includes a sample window, wherein the sample window is configured to permit visual analysis of tissue samples.

Example 12

The biopsy device of any one or more of examples Example 1 through 11, wherein the analysis area includes one or more electrodes, wherein the one or more electrodes are configured to detect impedance of tissue samples.

Example 13

The biopsy device of Example 1, wherein the tissue sample holder includes an outer cup and a bulk tissue sample basket removably disposed within the outer cup.

Example 14

The biopsy device of any one or more of Examples 13, wherein the outer cup is releasably attached to the body.

Example 15

The biopsy device of any one or more of Examples 13, wherein the bulk tissue sample basket defines a sample collection area, wherein the sample collection area is sized to receive from about 10 to about 50 tissue samples.

Example 16

A biopsy system, comprising: (a) a biopsy device, wherein the biopsy device includes: (i) a body, (ii) a needle, (iii) a cutter, wherein the needle extends from the body to collect tissue samples using the cutter, (iv) a sample analyzer, wherein the sample analyzer includes a gate, wherein the gate is configured to selectively arrest movement of a tissue sample within the sample analyzer for analysis, (v) a tissue sample holder, wherein the tissue sample holder is in communication with the sample analyzer, wherein the tissue sample holder is configured to receive tissue samples after analysis by the sample analyzer; and (b) a control module, wherein the control module is in communication with the biopsy device.

Example 17

The biopsy system of Example 16, wherein the gate is configured to transition between an open and closed position to selectively arrest a tissue sample before transport to the tissue sample holder.

Example 18

The tissue sample holder of Example 16, wherein the analyzer further includes a sample lumen and a first detector in communication with the control module, wherein the first detector protrudes into the first lumen, wherein the first lumen is in communication with the cutter to receive a tissue sample therein.

Example 19

The tissue sample holder of Example 16, wherein the sample analyzer includes a tissue window, wherein the tissue window is disposed within the body of the biopsy device and is sealed relative to an exterior of the biopsy device.

Example 20

A biopsy device, comprising: (a) a body; (b) a needle; (c) a cutter; and (d) a tissue handling assembly in communication with the cutter, wherein the tissue handling assembly includes: (i) a sample viewer integrated into the body, wherein the sample viewer is configured to permit analysis of tissue samples as they are received by the tissue handling assembly from the cutter, (ii) a bulk collection tray, wherein the bulk collection tray is configured to receive a plurality of tissue samples, and (iii) a tissue gate, wherein the tissue gate is positioned between the tissue analysis feature and the bulk collection tray, wherein the tissue gate is configured to selectively control transport of tissue samples between the sample viewer and the bulk collection tray.

Example 21

A tissue sample holder, comprising: (a) an outer cover; (b) a tissue receiving member; and (c) a sample management assembly, wherein the sample management assembly comprises first plurality of plates and a second plurality plates, wherein each plate of the first plurality of plates is alternatingly disposed between each plate of the second plurality of plates, wherein the first plurality of plates are configured to move rotationally relative to the second plurality of plates to manipulate a tissue sample into the tissue receiving member.

Example 22

The tissue sample holder of claim 21, wherein each plate of the first plurality of plates comprises a tissue groove, wherein the tissue groove of each plate is configured to align with the tissue grooves of the other first plurality of plates to define a tissue manipulation chamber.

Example 23

The tissue sample holder of Example 22, wherein the tissue manipulation chamber is configured to receive a single tissue sample.

Example 24

The tissue sample holder of any one or more of Examples 21 or 22, wherein the tissue manipulation chamber is configured to move relative to the second plurality of plates in response to movement of the first plurality of plates.

Example 25

The tissue sample holder of Example 24, wherein each tissue groove of each plate of the first plurality of plates is configured to progressively retract relative to the second plurality of plates as the first plurality of plates move relative to the second plurality of plates.

Example 26

The tissue sample holder of Example 25, wherein retraction of each tissue groove of each plate of the first plurality of plates is configured to progressively decrease the effective size of the tissue manipulation chamber.

Example 27

The tissue sample holder of any one of Examples 21 through 26, the outer cup comprises a first member and a second member, wherein each of the first member and second member is configured to engage each plate of the second plurality of plates.

Example 28

The tissue sample holder of Example 27, wherein the first member and second member are configured to maintain each plate of the second plurality of plates in a single position relative to the first plurality of plates.

Example 29

The tissue sample holder of any one or more of Examples 21 through 28, wherein the sample management assembly further comprises a drive shaft, wherein the drive shaft connects the first plurality of plates and the second plurality of plates.

Example 30

The tissue sample holder of Example 29, wherein the drive shaft is keyed to the first plurality of plates such that the drive shaft is configured to transfer rotational motion to the first plurality of plates.

Example 31

The tissue sample holder of Example 30, wherein the drive shaft is configured to rotate relative to the second plurality of plates.

Example 32

The tissue sample holder of any one or more of Examples 21 through 30, further comprising a sample analysis assembly, wherein the sample analysis assembly is associated with the sample management assembly.

Example 33

The tissue sample holder of Example 32, wherein the sample analysis assembly is configured to permit visual analysis of tissue samples.

Example 34

The tissue sample holder of any one or more of Examples 32 or 33, wherein the sample analysis assembly is configured to permit bio impedance analysis of tissue samples.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

By way of aspect only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide or steam.

Embodiments of the devices disclosed herein can be reconditioned for reuse after at least one use. Reconditioning may include any combination of the steps of disassembly of the device, followed by cleaning or replacement of particular pieces, and subsequent reassembly. In particular, embodiments of the devices disclosed herein may be disassembled, and any number of the particular pieces or parts of the devices may be selectively replaced or removed in any combination. Upon cleaning and/or replacement of particular parts, embodiments of the devices may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the aspects, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A biopsy device, comprising:
   (a) a body;
   (b) a needle extending distally from the body;
   (c) a cutter movable relative to the needle; and
   (d) a tissue management assembly in communication with the cutter, the tissue management assembly including:
      (i) a sample viewer integrated into the body, the sample viewer being configured to permit analysis of each tissue sample of a plurality of tissue samples as each tissue sample is received by the tissue management assembly from the cutter,
      (ii) a sample basket defining a bulk sample chamber configured to receive the plurality of tissue samples, and
      (iii) a tissue gate, the tissue gate being positioned between the sample viewer and the sample basket, the tissue gate being configured to selectively control transport of each tissue sample of the plurality of tissue samples from the sample viewer to the sample basket.

2. The biopsy device of claim 1, the sample viewer being integrated into a distal portion of the body such that the sample viewer is distal of the sample basket.

3. The biopsy device of claim 1, the sample viewer including one or more sensors incorporated into a portion of the sample viewer.

4. The biopsy device of claim 3, the one or more sensors including a bioimpedance sensor configured to identify one or more physical characteristics of each tissue sample of the plurality of tissue samples.

5. The biopsy device of claim 1, the tissue gate including a movable filter, the sample viewer defining a single tissue sample chamber, the single tissue sample chamber being in selective communication with the sample basket via selective movement of the filter.

6. The biopsy device of claim 5, the movable filter including a first disk, the first disk including a plurality of outer filter portions and a plurality of openings, each outer filter portion being positioned adjacent to a corresponding opening such that the plurality of outer filter portions and the plurality of openings form an alternating arrangement.

7. The biopsy device of claim 6, the first disk being configured to rotate relative to the cutter to successively alternatingly align an outer filter portion or opening with the cutter.

8. The biopsy device of claim 7, the tissue gate being configured to provide a closed configuration when an outer filter portion of the first disk is aligned with the cutter, the tissue gate being further configured to provide an open configuration when an opening of the first disk is aligned with the cutter.

9. The biopsy device of claim 8, the movable filter further including a second disk, the second disk including a plurality of vacuum chambers and a plurality of openings.

10. The biopsy device of claim 9, the first disk being fixedly secured to the second disk.

11. The biopsy device of claim 1, the sample basket including a floor, a pair of sidewalls, and a distal wall, the floor, the pair of sidewalls, and the distal wall defining the bulk sample chamber, the distal wall including a single tissue opening for receiving each tissue sample of the plurality of tissue samples.

12. The biopsy device of claim 11, the floor of the sample basket including a plurality of vacuum openings, the distal wall further including a vacuum passage, the vacuum passage being configured to receive a vacuum to communicate the vacuum from the vacuum passage and into the bulk sample chamber through the plurality of vacuum openings of the floor.

13. The biopsy device of claim 1, the tissue management assembly further including a transport tube, the transport tube being in communication with the cutter to communicate each tissue sample from the cutter and into the sample basket.

14. The biopsy device of claim 13, the transport tube extending from the sample viewer to the cutter.

15. The biopsy device of claim 14, the transport tube having a cutter seal, the cutter seal being configured to sealingly engage the cutter.

16. A biopsy device, comprising:
(a) a body;
(b) a needle extending distally from the body and defining a longitudinal axis;
(c) a cutter; and
(d) a tissue handling assembly in communication with the cutter, the tissue handling assembly including a tissue gate, the tissue gate including a movable filter configured to transition between a tissue transport configuration and a tissue stopping configuration, the tissue gate being positioned along the longitudinal axis of the needle between a sample window and a bulk collection tray, the tissue gate being configured to selectively stop each tissue sample of the plurality of tissue samples when the movable filter is in the tissue stopping configuration to permit visual inspection of each tissue sample using the sample window before the tissue sample reaches the bulk collection tray, the tissue handling assembly further including the sample window and a tissue sample holder having the bulk collection tray.

17. The biopsy device of claim 16, the sample window, the tissue sample holder, and the tissue gate all being aligned with the longitudinal axis defined by the needle.

18. The biopsy device of claim 16, the movable filter being configured to transition between the tissue transport configuration and the tissue stopping configuration based on movement of the cutter.

19. The biopsy device of claim 16, the movable filter including one or more vent openings, the vent openings being configured to permit a flow of vacuum through the tissue gate and into the cutter when the movable filter is in the sample stopping configuration.

* * * * *